(12) United States Patent
Fagan et al.

(10) Patent No.: US 7,563,767 B2
(45) Date of Patent: Jul. 21, 2009

(54) BETA DEFENSIN PROTEINS

(76) Inventors: Richard Joseph Fagan, 60 Charlotte Street, London, W1T 2NU (GB); David Michalovich, 60 Charlotte Street, London, W1T 2NU (GB); Simon John White, 60 Charlotte Street, London, W1T 2NU (GB); Christine Power, Rue des Jonquilles, 10, F-01710 Thoiry (FR); Melanie Yorke, 20a Chemin de Vuillonnex, CH-1232 Confignon (CH)

( * ) Notice: Subject to any disclaimer, the term of this patent is extended or adjusted under 35 U.S.C. 154(b) by 543 days.

(21) Appl. No.: 10/539,656

(22) PCT Filed: Jan. 13, 2004

(86) PCT No.: PCT/GB2004/000101

§ 371 (c)(1),
(2), (4) Date: Feb. 27, 2006

(87) PCT Pub. No.: WO2004/063219

PCT Pub. Date: Jul. 29, 2004

(65) Prior Publication Data

US 2009/0042775 A1 Feb. 12, 2009

(30) Foreign Application Priority Data

Jan. 13, 2003 (GB) .................................. 0300718.4

(51) Int. Cl.
*A61K 38/17* (2006.01)
*C07K 14/435* (2006.01)
*C12P 21/02* (2006.01)

(52) U.S. Cl. ..................... 514/12; 530/324; 435/69.1

(58) Field of Classification Search ............... 514/12; 530/324; 435/69.1
See application file for complete search history.

(56) References Cited

FOREIGN PATENT DOCUMENTS

| WO | WO 02/04487 A2 | 2/2002 |
| WO | WO 03/024992 A2 | 3/2003 |

OTHER PUBLICATIONS

Result 1, search of protein sequence database from issued patents, alignment of SEQ ID No. 14 with SEQ ID No. 46 from US Pat. No. 7,338,936, search performed Feb. 9, 2009.*
Cole, A.M., et al. "Retrocyclin: A primate peptide that protects cells from infection by T- and M-tropic strains of HIV-1", *PNAS*, Feb. 19, 2002, pp. 1813-1818, vol. 99, No. 4.
Nizet, V., et al. "Innate antimicrobial peptide protects the skin from invasive bacterial infection", *Nature*, Nov. 2001, pp. 454-457, vol. 414.
Fellermann, K. and Stange, E. "Defensins—innate immunity at the epithelial frontier" *Eur J Gastroenterol Hepatol*, 2001, 13:771-776.
Harder, J. "A peptide antibiotic from human skin" *Nature*, 1997, 387:861.
Schutte, B.C. et al. "Discovery of five conserved beta-defensin gene clusters using a computational search strategy" *Proc. Natl. Acad. Sci. USA*, 2002, 99:2129-2133.

* cited by examiner

*Primary Examiner*—Delia M. Ramirez
*Assistant Examiner*—Rosanne Kosson
(74) *Attorney, Agent, or Firm*—Saliwanchik, Lloyd & Saliwanchik

(57) ABSTRACT

This invention relates to novel proteins, termed INSP 108 and INSP 109, herein identified as members of the defensin family of proteins and to the use of these proteins and nucleic acid sequences from the encoding genes in the diagnosis, prevention and treatment of disease.

10 Claims, 22 Drawing Sheets

Figure 1: BLAST result against NCBI non-redundant database using SEQ ID NO: 6 (the INSP108 polypeptide).

```
BLASTP 2.2.2 [Jan-08-2002]

Reference: Altschul, Stephen F., Thomas L. Madden, Alejandro A. Schaffer,
Jinghui Zhang, Zheng Zhang, Webb Miller, and David J. Lipman (1997),
"Gapped BLAST and PSI-BLAST: a new generation of protein database search
programs", Nucleic Acids Res. 25:3389-3402.

Query= INSP108.pp
        (77 letters)

Database: All non-redundant GenBank CDS
translations+PDB+SwissProt+PIR+PRF
           1,267,376 sequences; 405,046,914 total letters Searching..................................................done Score     E
Sequences producing significant alignments:                       (bits)  Value ref|NP_697019.1| defensin, beta 123; defensin, beta 23 [Homo sap...   51   4e-06
ref|XP_141520.1| similar to defensin, beta 123; defensin, beta 2...   46   1e-04
gb|AAM93917.1| defensin beta 124 [Homo sapiens]                       39   0.012
emb|CAB72350.2| dJ1018D12.3 (a putative novel protein) [Homo sap...   39   0.016
ref|NP_473453.1| epididymus specific clone 42; chromosome 20 ope...   39   0.016
ref|NP_660139.1| defensin beta 119; testis-specific beta-defensi...   39   0.021
sp|Q95LI0|D118_MACMU Beta-defensin 118 precursor (Epididymal sec...   37   0.079
ref|NP_631968.1| defensin beta 15 [Mus musculus] >gi|19171622|em...   37   0.079
ref|NP_689464.1| defensin, beta 106; defensin, beta 6 [Homo sapi...   35   0.18
gb|AAN33114.1| beta-defensin 106 [Homo sapiens]                       35   0.18
```

Figure 2: Alignment between INSP108 polypeptide sequence (SEQ ID NO:6) and defensin beta 123 (*Homo sapiens*).

```
>ref|NP_697019.1| defensin, beta 123; defensin, beta 23 [Homo sapiens]
 sp|Q8N688|D123_HUMAN Beta-defensin 123 precursor (Beta-defensin 23) (DEFB-23)
 gb|AAM93916.1| defensin beta 123 [Homo sapiens]
          Length = 67

Score = 50.8 bits (120), Expect = 4e-06
 Identities = 26/67 (38%), Positives = 33/67 (48%), Gaps = 10/67 (14%)

Query: 6   VLLALVVLNLLFYVPPGRSGPNVYIQKIFASCWRLQGTCRPKCLKNEQYRILCDTIHLCC 65
           +LL L VL LL  + PG +          CW L G CR +C K E+  + C    +CC
Sbjct: 4   LLLTLTVLLLLSQLTPGGT----------QRCWNLYGKCRYRCSKKERVYVYCINNKMCC 53

Query: 66  VNPKYLP 72
           V PKY P
Sbjct: 54  VKPKYQP 60
```

Figure 3: Sig P cleavage site prediction for INSP108.
>INSP108.pp
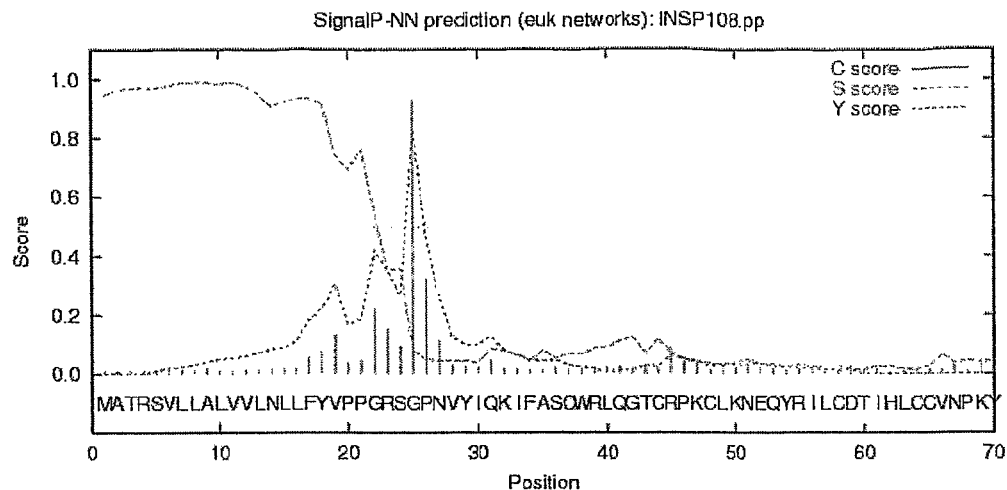
```
>INSP108.pp              length = 70
# Measure   Position   Value   Cutoff   signal peptide?
   max. C      25      0.933    0.33        YES
   max. Y      25      0.828    0.32        YES
   max. S       9      0.991    0.82        YES
   mean S     1-24     0.864    0.47        YES
# Most likely cleavage site between pos. 24 and 25: GRS-GP
```
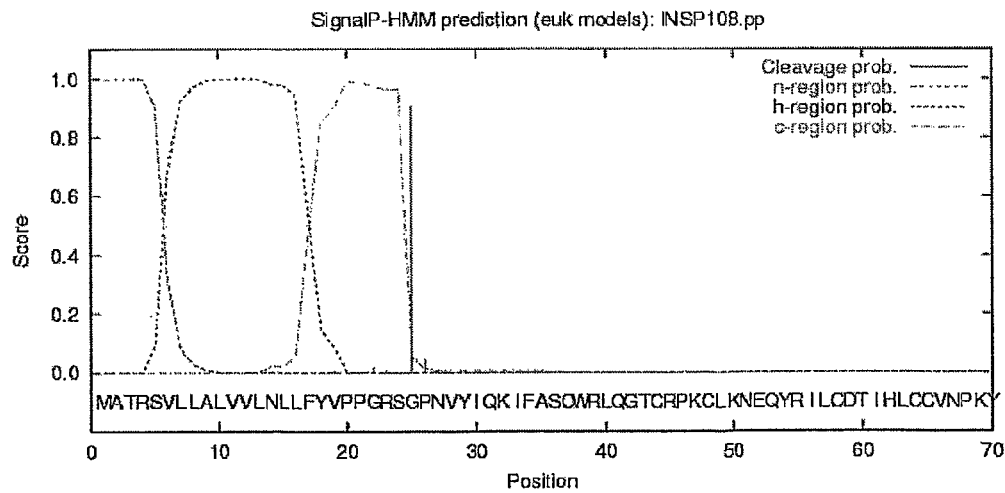
```
>INSP108.pp
Prediction: Signal peptide
Signal peptide probability: 1.000
Signal anchor probability: 0.000
Max cleavage site probability: 0.906 between pos. 24 and 25
```

Figure 4: BLAST result against NCBI non-redundant database using SEQ ID NO: 14 (the INSP109 polypeptide).

```
BLASTP 2.2.2 [Jan-08-2002]

Reference: Altschul, Stephen F., Thomas L. Madden, Alejandro A. Schaffer,
Jinghui Zhang, Zheng Zhang, Webb Miller, and David J. Lipman (1997),
"Gapped BLAST and PSI-BLAST: a new generation of protein database search
programs",  Nucleic Acids Res. 25:3389-3402.

Query= INSP109.pp
        (78 letters)

Database: All non-redundant GenBank CDS
translations+PDB+SwissProt+PIR+PRF
           1,267,376 sequences; 405,046,914 total letters Searching..................................................done Score     E
Sequences producing significant alignments:                      (bits)  Value dbj|BAC37510.1| unnamed protein product [Mus musculus]             88    3e-17
ref|NP_062702.1| defensin beta 4; beta defensin-4 [Mus musculus]... 33    1.1
emb|CAA08905.1| beta defensin-2 [Capra hircus]                     31    3.3
ref|NP_348802.1| Uncharacterized protein, homolog HI1244 from Ha... 31    4.3
gb|AAG10514.1|AF288371_1 beta-defensin 4 variant [Mus musculus]    31    4.3
emb|CAD23115.1| blue cone opsin [Cottus kesslerii]                 30    7.4
ref|NP_689464.1| defensin, beta 106; defensin, beta 6 [Homo sapi... 30    9.6
gb|AAN33114.1| beta-defensin 106 [Homo sapiens]                    30    9.6
ref|XP_163302.1| hypothetical protein XP_163302 [Mus musculus]     30    9.6
```

Figure 5: Alignment between INSP109 polypeptide sequence (SEQ ID NO:14) and defensin beta 4 (*Mus musculus*).

```
>ref|NP_062702.1| defensin beta 4; beta defensin-4 [Mus musculus]
 sp|P82019|BD04_MOUSE Beta-defensin 4 precursor (BD-4) (mBD-4)
 gb|AAD38852.1|AF155882_1 beta defensin-4 [Mus musculus]
 gb|AAG02197.1|AF287475_1 beta-defensin 4 precursor [Mus musculus]
 dbj|BAB26051.1| unnamed protein product [Mus musculus]
 dbj|BAB26207.1| unnamed protein product [Mus musculus]
          Length = 63

Score = 32.7 bits (73), Expect = 1.1
 Identities = 19/56 (33%), Positives = 27/56 (47%), Gaps = 1/56 (1%)

Query: 8   LLFFLVILLPSGKGMFGNDGVKVRTCTSQKAVCFFGCPPGYRWIAFC-HNILSCCK 62
           LLF  +++L S    F         TC + A+C+ CP +R I  C H  + CCK
Sbjct: 6   LLFTFLLVLLSPLAAFTQIINNPITCMTNGAICWGPCPTAFRQIGNCGHFKVRCCK 61
```

Figure 6: Sig P cleavage site prediction for INSP109.
>INSP109.pp
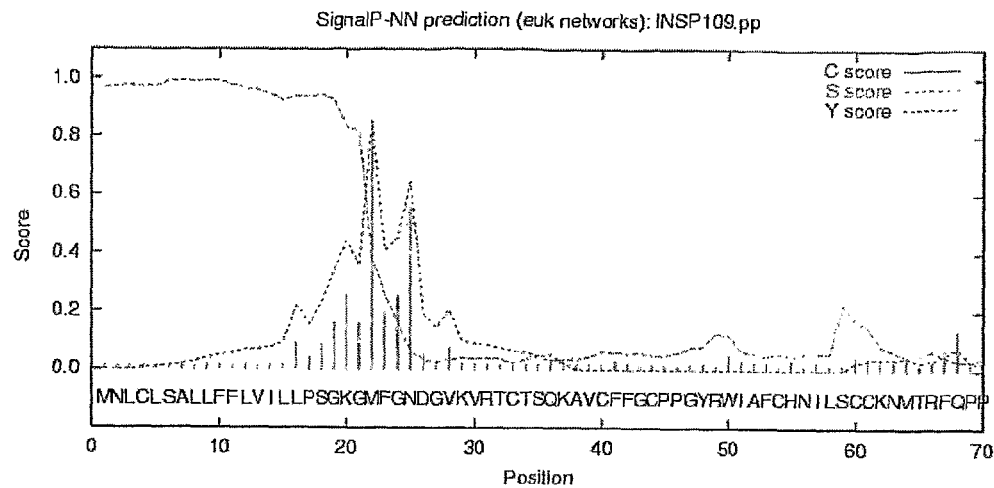
```
>INSP109.pp            length = 70
# Measure   Position   Value   Cutoff   signal peptide?
   max. C     22       0.849    0.33     YES
   max. Y     22       0.854    0.32     YES
   max. S      7       0.994    0.82     YES
   mean S    1-21      0.953    0.47     YES
# Most likely cleavage site between pos. 21 and 22: GKG-MF
```
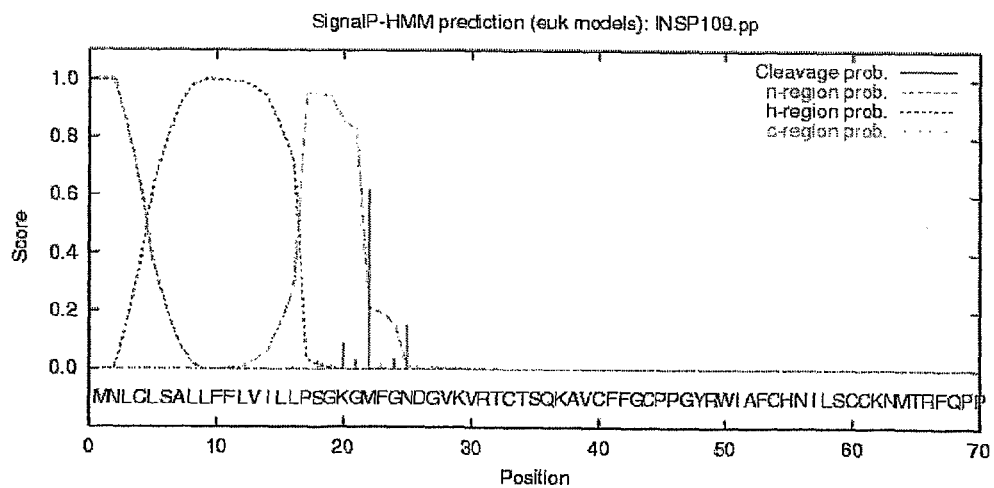
>INSP109.pp
Prediction: Signal peptide
Signal peptide probability: 0.999
Signal anchor probability: 0.001
Max cleavage site probability: 0.619 between pos. 21 and 22

Figure 7: Predicted nucleotide sequence of INSP108 with translation

```
  1  ttgttccaaa aggttcacta gccatgcagc tccccgtctc ttcaaagctg cggagagagt
 61  gactctccga tgagtcacag ctgcttcttt gctgattggt atggccacaa ggagcgtcct
                                                   m  a  t   r  s  v
```

```
121  cttggccctc gtggtcctta acttactctt ctatgttcca ccaggtagaa gtggacccaa
      l  l  a  l  v  v  l  n  l  l  f  y  v  p  p  g  r  s  g  p 181  tgtctacata caaaaaatct ttgcttcatg ttggcgactg caaggtactt gccggccaaa
      n  v  y  i  q  k  i  f  a  s  c  w  r  l  q  g  t  c  r  p 241  atgtctaaaa aacgaacaat atcgtatttt gtgtgatact atacatttgt gctgtgtaaa
      k  c  l  k  n  e  q  y  r  i  l  c  d  t  i  h  l  c  c  v 301  cccaaaatat ttacctatac tgactgggaa atagttgtga gtacctgaaa gctgttgctg
      n  p  k  y  l  p  i  l  t  g  k
                            INSP108-R1

361  atttcctctg ggaacccaga tccctctcag ttgcaccatt cgattaaaac aatggcttta
421  gcctatcagt gttc
```

Position and sense of PCR primers ⟶
Underlined: signal sequence

Figure 8: Nucleotide sequence with translation of INSP108 PCR product cloned using primers INSP108-CP1 and INSP108-CP2.

```
  1  attggtatgg ccacaaggag cgtcctcttg gccctcgtgg tccttaactt actcttctat
           m    a  t  r   s  v  l  l   a  l  v  v   l  n  l  l   f  y
        ─────────────▶
         INSP108-F1

61  gttccaccag gtagaagtgg acccaatgtc tacatacaaa aaatctttgc ttcatgttgg
      v  p  p   g  r  s   g  p  n  v   y  i  q   k  i  f   a  s  c  w 121  cgactgcaag gtacttgccg gccaaaatgt ctaaaaaacg aacaatatcg tattttgtgt
      r  l  q   g  t  c   r  p  k  c   l  k  n   e  q  y   r  i  l  c 181  gatactatac atttgtgctg tgtaaaccca aaatatttac ctatactgac tgggaaatag
      d  t  i   h  l  c   c  v  n  p   k  y  l   p  i  l   t  g  k
                                                  ◀─────────────
                                                   INSP108-R1

241  ttgtg
```

Position and sense of PCR primers ─────▶

Figure 9: Map of pCR4-TOPO-INSP108

```
Molecule:       pCR4-TOPO-INSP108,  4202 bps DNA Circular
Type      Start      End    Name       Description MARKER    205              M13R       M13 rev priming site
MARKER    243              T3         T3 priming site
MARKER    295              CP2        INSP108-CP2
GENE      533       303  C cds        INSP108 cds
MARKER    539            C CP1        INSP108-CP1
REGION    539       295  C Insert     INSP108-F1R1 PCR product
MARKER    592            C T7         T7 priming site
MARKER    600            C M13F       M13 for priming site
GENE      1404      2198   Kan        Kanamycin resistance gene ORF
GENE      2402      3262   Amp        Ampicillin resistance gene ORF
MARKER    3407             pUC ori    pUC origin
```

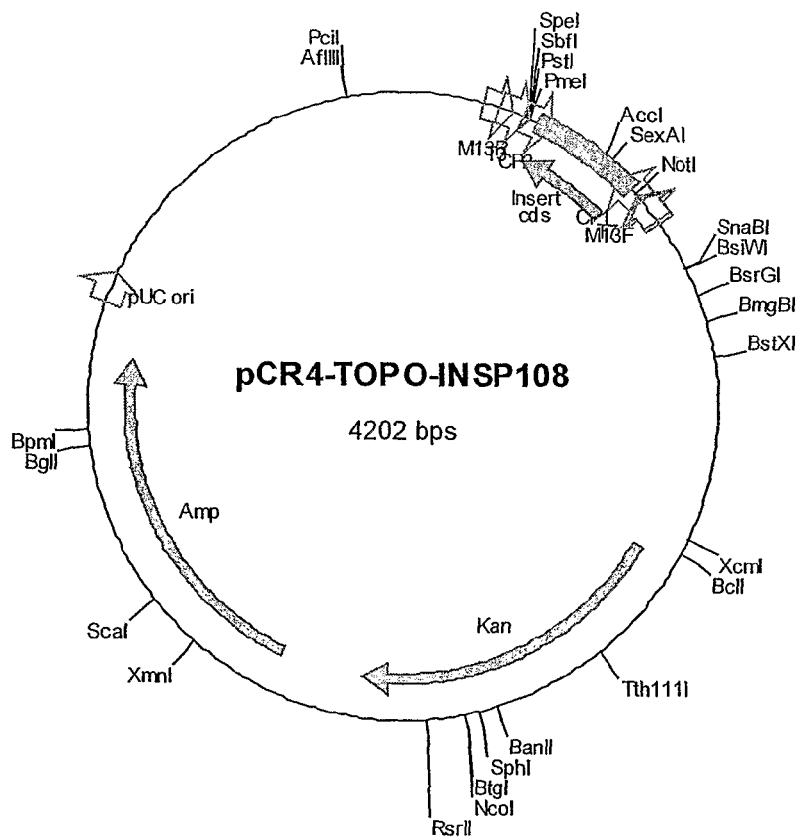

Figure 10: Map of pDONR 221

```
Molecule:      pDONR221,  4759 bps DNA Circular
File Name:     pDONR221.cm5

Description:

Type       Start      End        Name       Description

REGION     295        268    C   rrnB T2    transcription termination sequence
REGION     470        427    C   rrnB T1    transcription termination sequence
REGION     536        553        21M13      M13 Forward primer
REGION     570        801        attP1
GENE       1197       1502       ccdB
GENE       1844       2503       Cm r       Chloramphenicol resistance gene
REGION     2751       2982       attP2
REGION     3040       3023   C   M13 Rev    M13 Reverse primer
GENE       3153       3962       Kan r
REGION     4083       4756       pUC ori
```

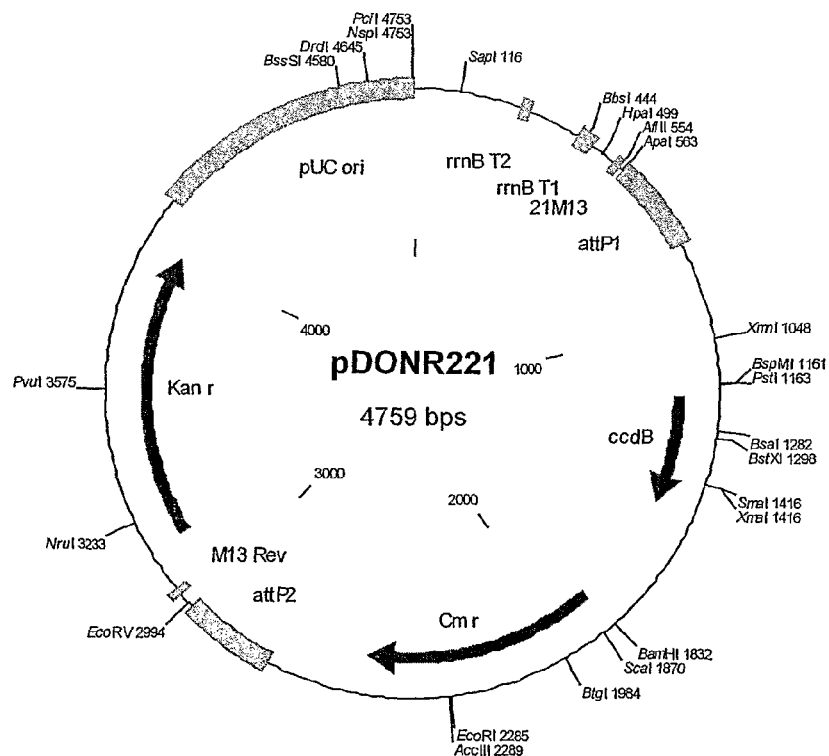

Figure 11: Map of expression vector pEAK12d

```
Molecule:       pEAK12 d,  8760 bps DNA Circular
File Name:      pEAK12DEST.cm5

Description:    Mammalian cell expression vector (plasmid ID 11345)

Molecule Features:

Type       Start     End     Name       Description

REGION        2      595                pmb-ori
GENE        596     1519     Amp
REGION     1690     2795     EF-1alpha
REGION     2703     2722                position of pEAK12F primer
REGION     2796     2845                MCS
MARKER     2855              attR1
GENE       3256     3915     CmR
GENE       4257     4562     ccdB
MARKER     4603           C  attR2
REGION     4733     4733                MCS
REGION     4734     5162                poly A/splice
REGION     4819     4848  C             position of pEAK12R primer
GENE       5781     5163  C  PUR        PUROMYCIN
REGION     6005     5782  C  tK         tK promoter
REGION     6500     6006  C  Ori P
GENE       8552     6500  C  EBNA-1
REGION     8553     8752     sv40
```

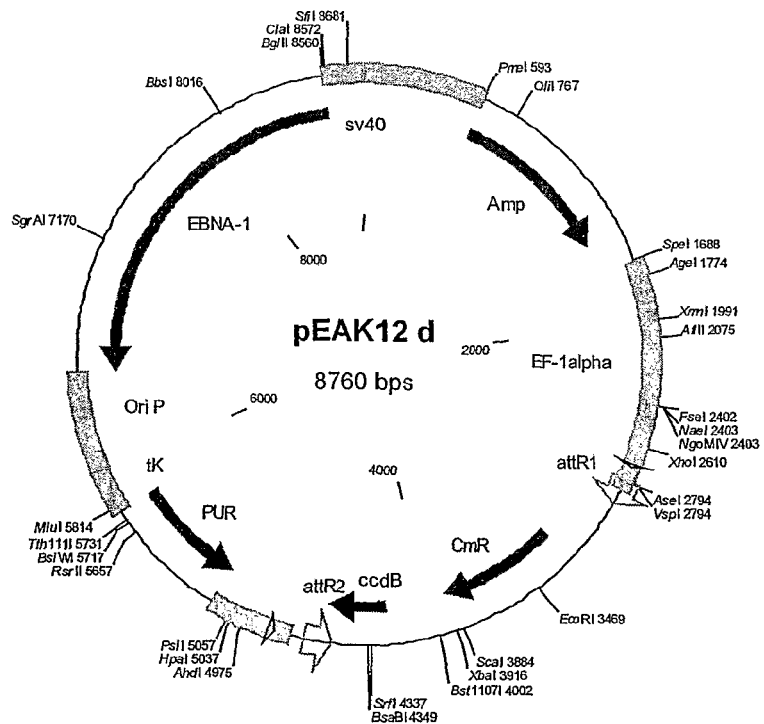

Figure 12: Map of expression vector pDEST12.2

```
Molecule:      pDEST 12.2,  7278 bps DNA Circular
File Name:     pDEST12-2.cm5

Description:   Eukaryoric expression vector
```

| Type | Start | End | Name | Description |
|---|---|---|---|---|
| REGION | 15 | 608 | CMV | CMV promoter |
| MARKER | 648 | | M13R | M13R primer |
| REGION | 687 | 706 | SP6 | SP6 promoter |
| REGION | 730 | 854 | attR1 | |
| GENE | 963 | 1622 | Cm | |
| GENE | 1964 | 2269 | ccdB | |
| REGION | 2310 | 2434 | attR2 | |
| GENE | 2484 | 2464 C | T7 | T7 promoter |
| MARKER | 2512 | | C 21M13 | 21M13 primer |
| REGION | 2784 | 3050 | pA | SV40 polyadenylation signal |
| REGION | 3176 | 3631 | f1 | f1 intergenic region |
| REGION | 3791 | 4099 | P SV40 | SV40 ori & early promoter |
| GENE | 4158 | 4952 | Neo | |
| REGION | 5016 | 5064 | pA | synthetic poly adenylation signal |
| GENE | 5475 | 6335 | Amp | |
| REGION | 6480 | 7153 | ori | pUC ori |

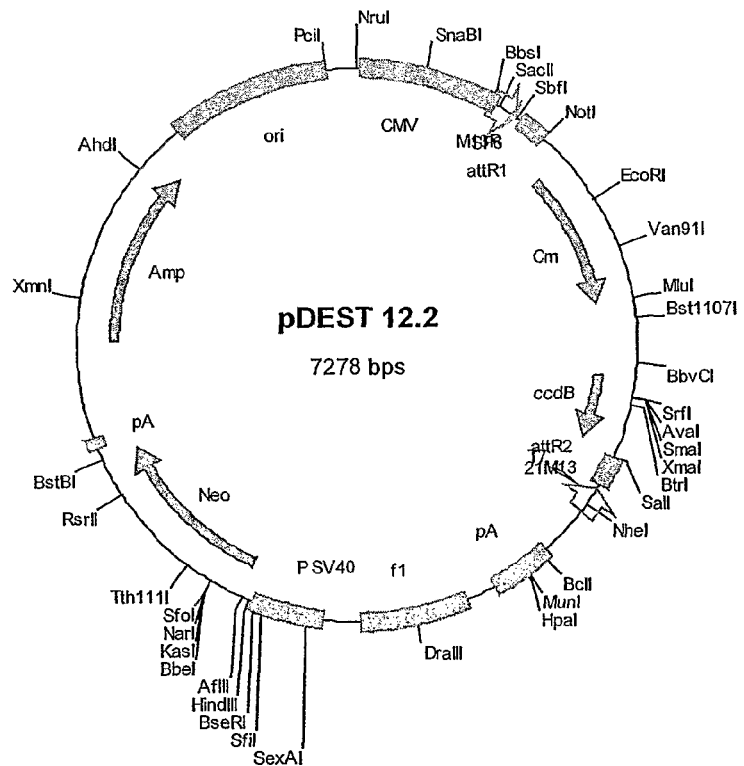

Figure 13: Map of pDONR221-INSP108-6HIS
```
Molecule:      pDONR221-INSP108-6HIS,  2805 bps DNA Circular
Type      Start    End    Name              Description
REGION    295      268  C rrnB T2           transcription termination sequence
REGION    470      427  C rrnB T1           transcription termination sequence
REGION    536      553    21M13             21M13 primer
REGION    570      651    attL1
GENE      677      925    INSP108-6HIS-V1   INSP108-6HIS ORF
REGION    940      1028   attL2
REGION    1086     1070 C M13 R             M13R primer
GENE      1199     2008   Kan r
GENE      2129     2802   pUC ori
```
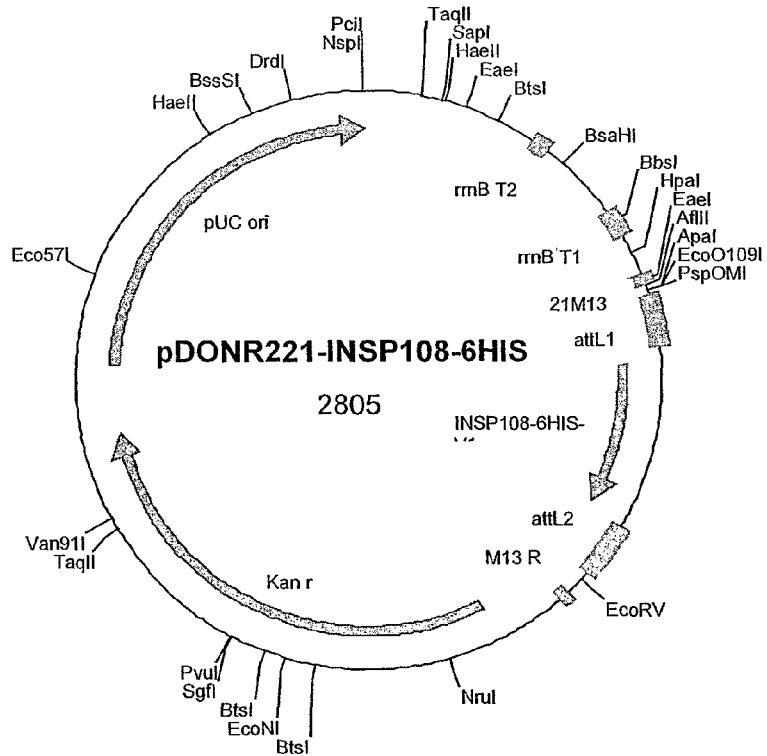

Figure 14: Map of pEAK12d-INSP108-6HIS
```
Molecule:    pEAK12d-INSP108,  7198 bps DNA Circular
Type      Start      End    Name          Description
REGION        2      595    pmb-ori
GENE        596     1519    Amp
REGION     1690     2795    EF-1alpha
REGION     2796     2845    MCS''
REGION     2855     2874    attB1
GENE       2888     3139    INSP108
REGION     3144     3165    attB2
REGION     3171     3171    'MCS
REGION     3172     3600    'A            poly A/splice
GENE       4219     3601  C PUR           PUROMYCIN
REGION     4443     4220  C tK            tK promoter
REGION     4938     4444  C Ori P
GENE       6990     4938  C EBNA-1
REGION     6991     7190    sv40
```
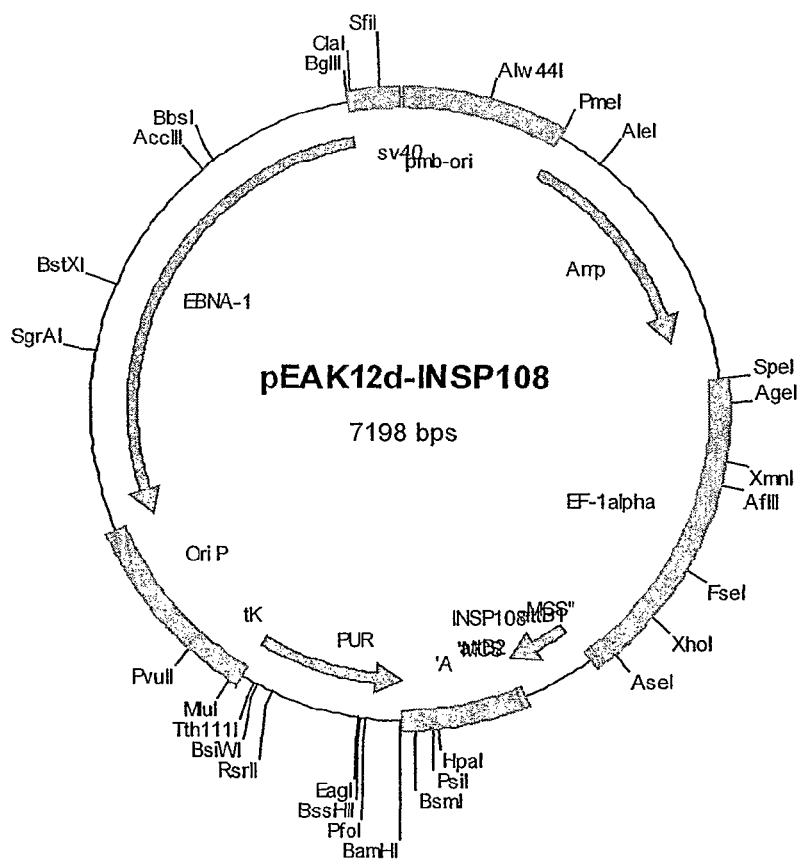

Figure 15: Map of pDEST12.2-INSP108-6HIS

```
Molecule:        pDEST12.2-INSP108-6HIS,   5884 bps DNA Circular

Type     Start    End    Name            Description

GENE       15     537    CMV promoter
REGION    648     665    M13rev          M13R primer
REGION    687     704    SP6             SP6 primer
REGION    730     762    attB1
GENE      763    1011    INSP108-6HIS
REGION   1015    1040    attB2
REGION   1090    1070  C T7              T7 promoter
REGION   1119    1101  C 21M13           21M13 primer
GENE     1225    1587    pA              SV40 polyadenylation signal
GENE     1781    2237    f1              f1 intergenic region
GENE     2301    2719    P SV40          SV40 ori & early promoter
GENE     2764    3558    Neo
GENE     3622    3670    pA              poly adenylation signal
GENE     4081    4941    Amp
GENE     5090    5729    ori             pUC ori
```

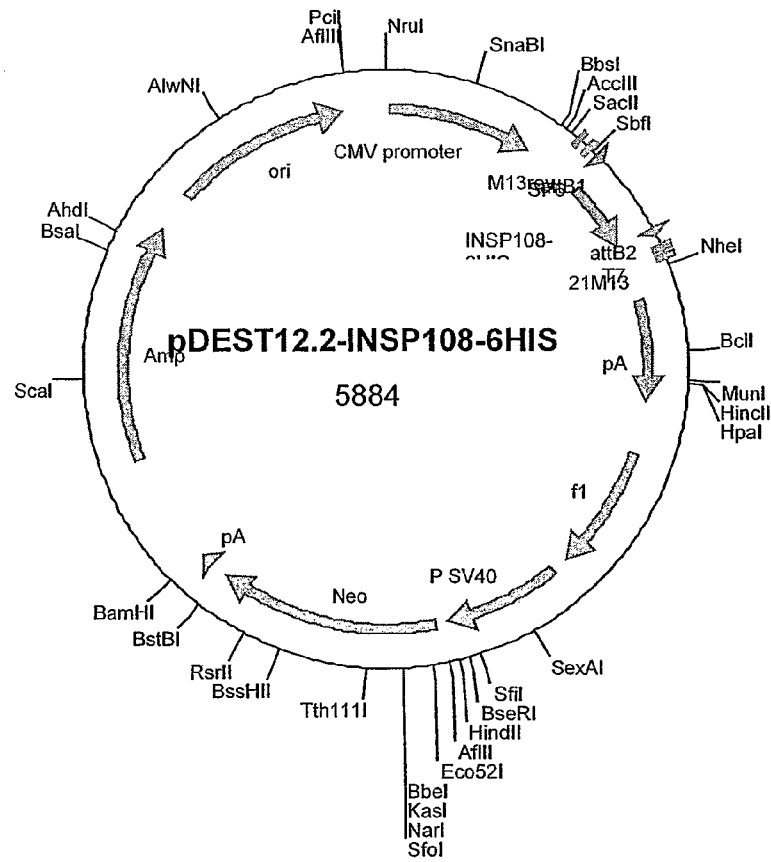

Figure 16: Predicted nucleotide sequence of INSP109 with translation

```
  1   atgaacctct gtctttctgc attactcttc ttcctggtga tcttactgcc ttcaggaaaa
        m  n  l   c  l  s   a  l  l  f   f  l  v   i  l  l   p  s  g  k 61   ggtatgtttg ggaatgatgg agtcaaagtt cgcacctgca ctagccagaa agccgtatgt
        g  m  f   g  n  d   g  v  k  v   r  t  c   t  s  q   k  a  v  c 121   ttcttcgggt gtccgccagg atacaggtgg attgcgttct gccacaatat tctgtcttgc
        f  f  g   c  p  p   g  y  r  w   i  a  f   c  h  n   i  l  s  c 181   tgtaaaaata tgacacgttt tcaaccccccg caagccaaag atccatgggt tcat
        c  k  n   m  t  r   f  q  p  p   q  a  k   d  p  w   v  h
```

Underlined= signal peptide

Figure 17: INSP109 coding exon organization in genomic DNA and position of PCR primers
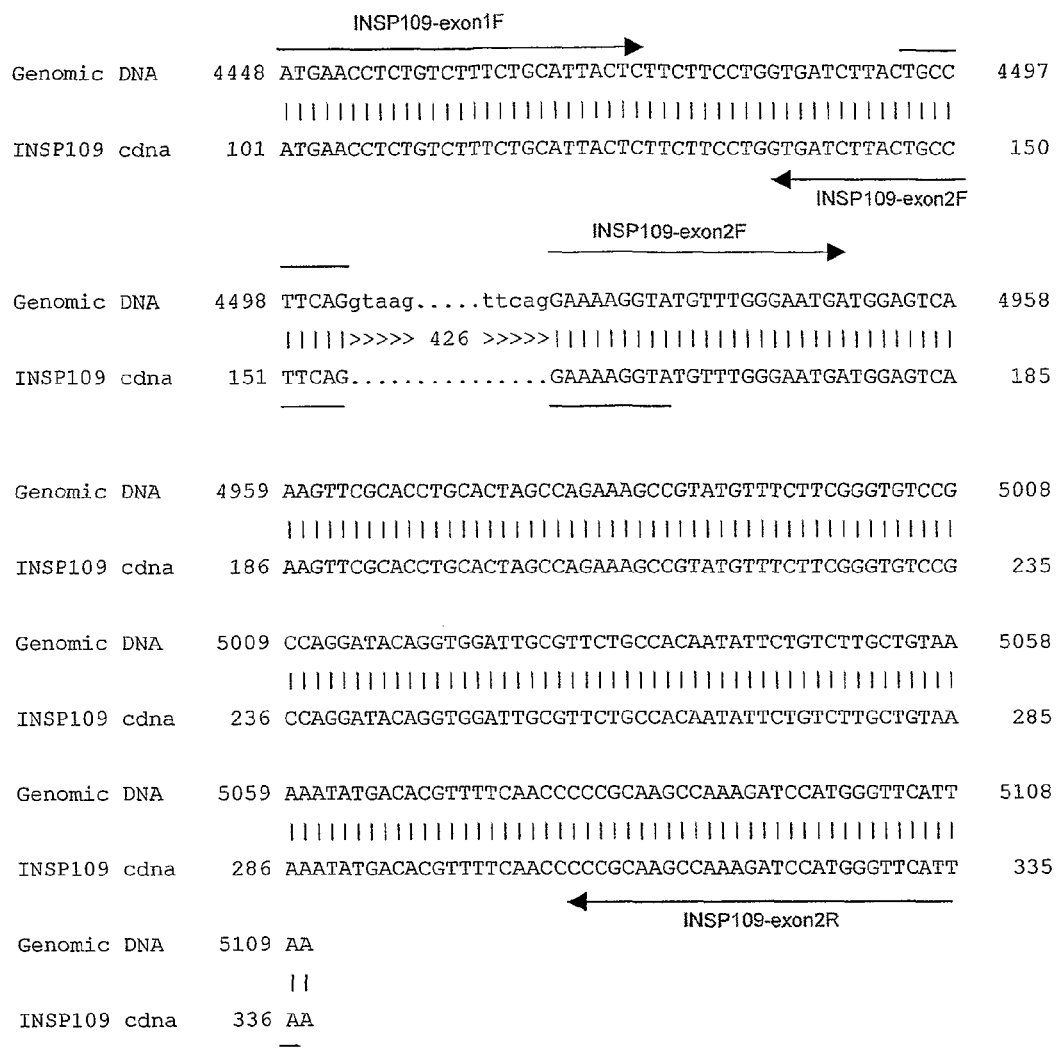

Figure 18: Nucleotide sequence and translation of cloned INSP109 ORF

```
  1   atgaacctct gtctttctgc attactcttc ttcctggtga tcttactgcc ttcaggaaaa
       m  n  l   c  l  s   a  l  l  f  f  l  v   i  l  l   p  s  g  k 61   ggtatgtttg ggaatgatgg agtcaaagtt cgcacctgca ctagccagaa agccgtatgt
       g  m  f   g  n  d   g  v  k  v  r  t  c   t  s  q   k  a  v  c 121   ttcttcgggt gtccgccagg atacaggtgg attgcgttct gccacaatat tctgtcttgc
       f  f  g   c  p  p   g  y  r  w  i  a  f   c  h  n   i  l  s  c 181   tgtaaaaata tgacacgttt tcaacccccg caagccaaag atccatgggt tcatta
       c  k  n   m  t  r   f  q  p  p  q  a  k   d  p  w   v  h
```

Figure 19: Map of pCR4-TOPO-INSP109

```
25 Nov 2003                 Molecule Features

Molecule:    pCR4-TOPO INSP109,  4193 bps DNA Circular
File Name:   13984[1].cm5

Description: Ligation of inverted INSP109 assembled insert into pCR4-
TOPO linear vector*

Type      Start    End    Name         Description

MARKER    205             M13R         M13 rev priming site
MARKER    243             T3           T3 priming site
REGION    530      295 C  Insert       INSP109 assembled insert
GENE      530      297 C  cds          INSP109 cds
MARKER    583          C  T7           T7 priming site
MARKER    591          C  M13F         M13 for priming site
GENE      1395     2189   Kan          Kanamycin resistance gene ORF
GENE      2393     3253   Amp          Ampicillin resistance gene ORF
MARKER    3398            pUC ori      pUC origin
```

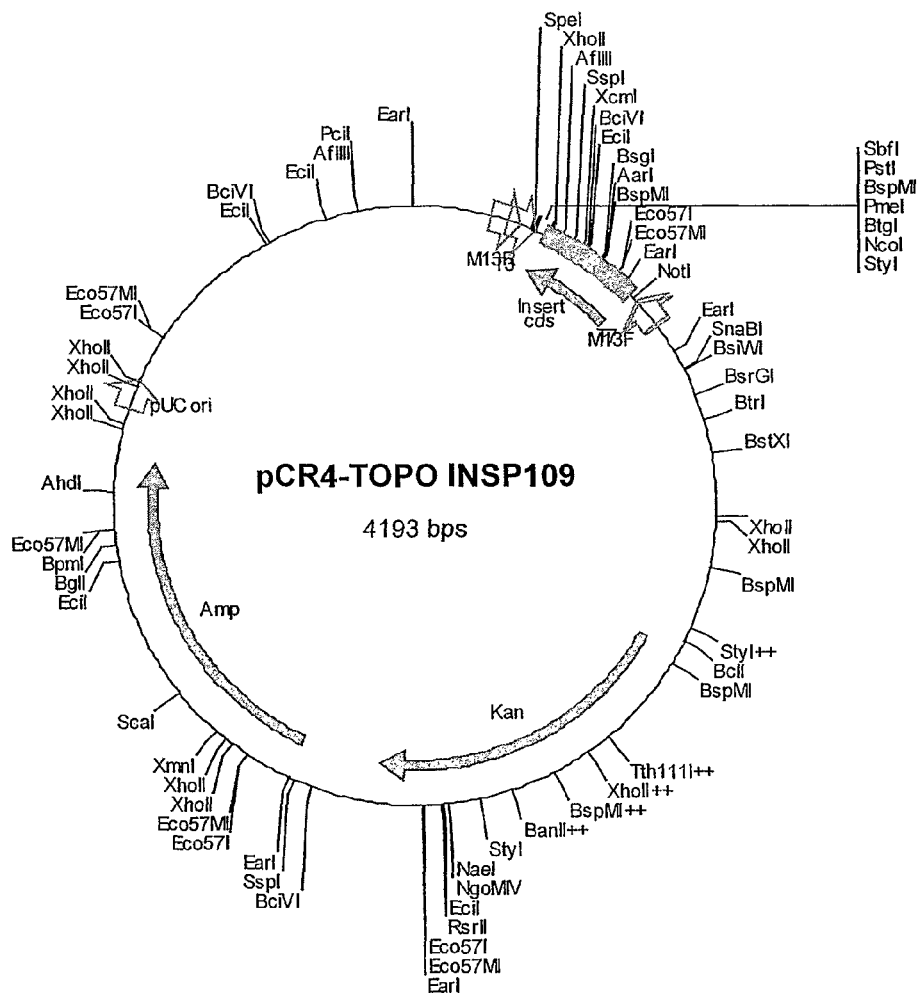

Figure 20: Map of pDONR-INSP109-6HIS
```
Molecule:     pDONR221-INSP109-6HIS,  2808 bps DNA Circular
Type     Start    End      Name           Description
REGION   295      268  C   rrnB T2        transcription termination sequence
REGION   470      427  C   rrnB T1        transcription termination sequence
REGION   536      553      21M13          21M13 primer
REGION   570      651      attL1
GENE     677      928      INSP109-6HIS
REGION   943      1031     attL2
REGION   1089     1073 C   M13 R          M13R primer
GENE     1202     2011     Kan r
GENE     2132     2805     pUC ori
```
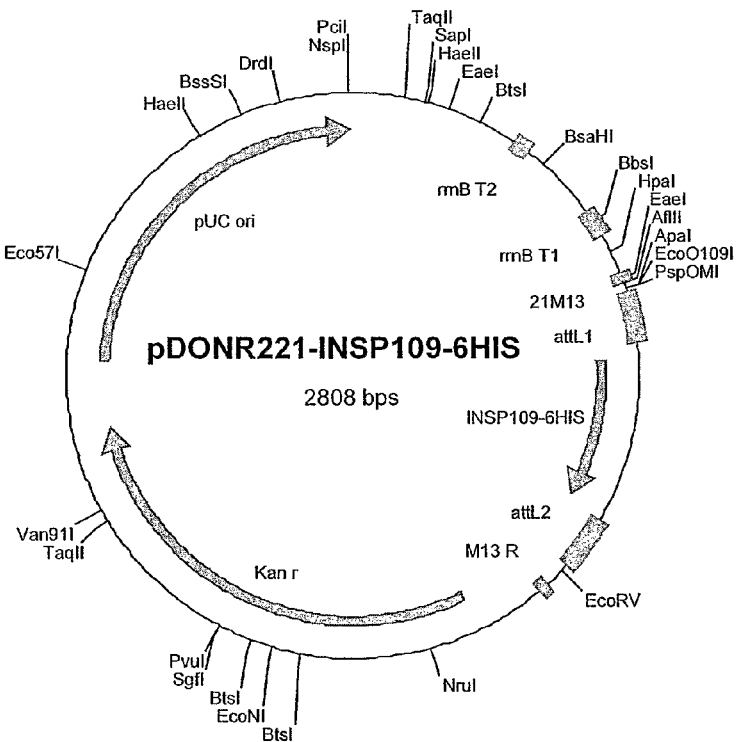

Figure 21: Map of pEAK12d-INSP109-6HIS
```
Molecule:      pEAK12d-INSP109-6HIS,   7201 bps DNA Circular
Type       Start     End     Name            Description
REGION        2       595    pmb-ori
GENE        596      1519    Amp
REGION     1690      2795    EF-1alpha
REGION     2796      2845    MCS''
REGION     2855      2874    attB1
GENE       2888      3142    INSP109-6HIS
REGION     3147      3168    attB2
REGION     3174      3174    'MCS
REGION     3175      3603    'A              poly A/splice
GENE       4222      3604  C PUR             PUROMYCIN
REGION     4446      4223  C tK              tK promoter
REGION     4941      4447  C Ori P
GENE       6993      4941  C EBNA-1
REGION     6994      7193    sv40
```
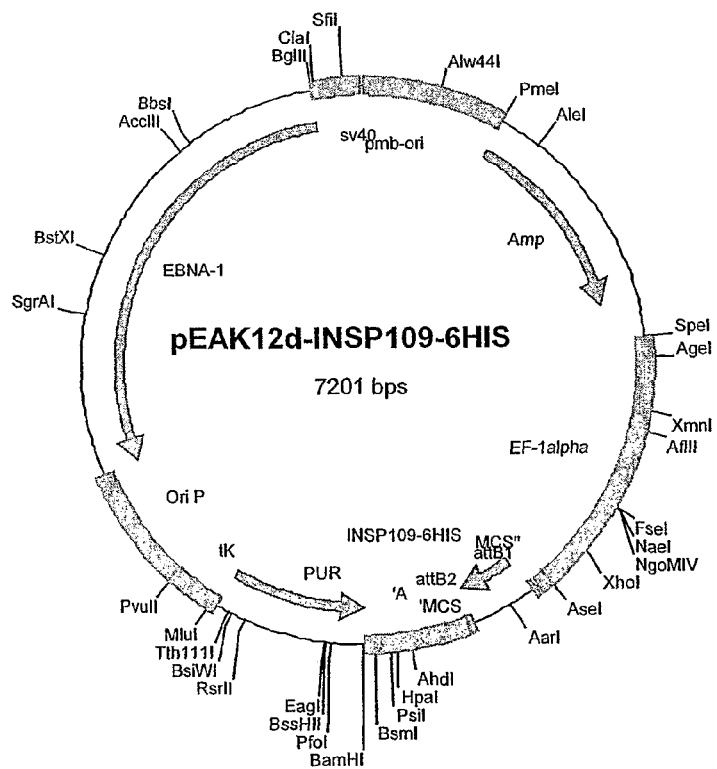

Figure 22: Map of pDEST12.2-INSP109-6HIS

```
Molecule:      pDEST12.2-INSP109-6HIS,  5887 bps DNA Circular

Type       Start      End    Name          Description

GENE         15       537    CMV promoter
REGION      648       665    M13rev        M13R primer
REGION      687       704    SP6           SP6 primer
REGION      730       762    attB1
GENE        763      1014    INSP109-6HIS
REGION     1018      1043    attB2
REGION     1093      1073 C  T7            T7 promoter
REGION     1122      1104 C  21M13         21M13 primer
GENE       1228      1590    pA            SV40 polyadenylation signal
GENE       1784      2240    f1            f1 intergenic region
GENE       2304      2722    P SV40        SV40 ori & early promoter
GENE       2767      3561    Neo
GENE       3625      3673    pA            poly adenylation signal
GENE       4084      4944    Amp
GENE       5093      5732    ori           pUC ori
```

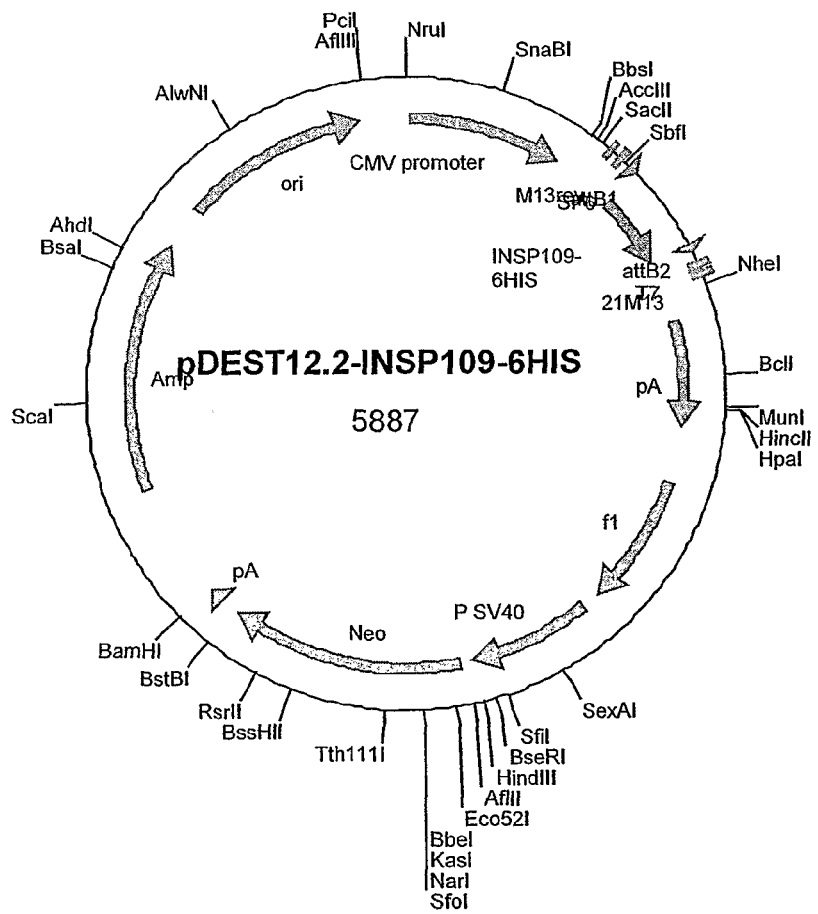

BETA DEFENSIN PROTEINS

CROSS-REFERENCE TO RELATED APPLICATION

This application is the National Stage of International Application Number PCT/GB2004/000101, filed Jan. 13, 2004, which is hereby incorporated by reference herein in its entirety, including any figures, tables, nucleic acid sequences, amino acid sequences, or drawings.

The Sequence Listing for this application is on duplicate compact discs labeled "Copy 1" and "Copy 2." Copy 1 and Copy 2 each contain only one file named "Mar07.ST25.txt" which was created on Mar. 8, 2007, and is 14 KB. The entire contents of each of the computer discs are incorporated herein by reference in their entireties.

This invention relates to the novel proteins, termed INSP108 and INSP109, herein identified as secreted proteins, in particular, as members of the defensin family of proteins and to the use of these proteins and nucleic acid sequences from the encoding genes in the diagnosis, prevention and treatment of disease.

All publications, patents and patent applications cited herein are incorporated in full by reference.

BACKGROUND

The process of drug discovery is presently undergoing a fundamental revolution as the era of functional genomics comes of age. The term "functional genomics" applies to an approach utilising bioinformatics tools to ascribe function to protein sequences of interest. Such tools are becoming increasingly necessary as the speed of generation of sequence data is rapidly outpacing the ability of research laboratories to assign functions to these protein sequences.

As bioinformatics tools increase in potency and in accuracy, these tools are rapidly replacing the conventional techniques of biochemical characterisation. Indeed, the advanced bioinformatics tools used in identifying the present invention are now capable of outputting results in which a high degree of confidence can be placed.

Various institutions and commercial organisations are examining sequence data as they become available and significant discoveries are being made on an on-going basis. However, there remains a continuing need to identify and characterise further genes and the polypeptides that they encode, as targets for research and for drug discovery.

Introduction

Secreted Proteins

The ability for cells to make and secrete extracellular proteins is central to many biological processes. Enzymes, growth factors, extracellular matrix proteins and signalling molecules are all secreted by cells. This is through fusion of a secretory vesicle with the plasma membrane. In most cases, but not all, proteins are directed to the endoplasmic reticulum and into secretory vesicles by a signal peptide. Signal peptides are cis-acting sequences that affect the transport of polypeptide chains from the cytoplasm to a membrane bound compartment such as a secretory vesicle. Polypeptides that are targeted to the secretory vesicles are either secreted into the extracellular matrix or are retained in the plasma membrane. The polypeptides that are retained in the plasma membrane will have one or more transmembrane domains. Examples of secreted proteins that play a central role in the functioning of a cell are cytokines, hormones, extracellular matrix proteins (adhesion molecules), proteases, and growth and differentiation factors. Description of some of the properties of these proteins follows.

Defensins

Defensins form part of the body's innate immune system that acts against invasion by foreign pathogens. Mammalian defensins are split into three categories; alpha, beta and theta, based upon the pattern of disulphide bonds. INSP108 and INSP109 fall into the beta category. These proteins are cationic and arginine-rich and share a typical tertiary structure despite differences in primary structure. They consist of three antiparallel beta sheets connected by loops, and a beta hairpin with hydrophobic properties protrudes orthagonally.

These proteins have been shown to have a broad spectrum of activity ranging from Gram-positive and Gram-negative bacteria to mycobacteria, fungi and even enveloped viruses. They bind to the phospholipid-rich negatively charged cell membranes of microbes and cause disruption, though the exact mode of action is yet to be determined. High concentrations are cytotoxic for mammalian cells, though it has been shown that lower concentrations promote growth in epithelial cells and fibroblasts, thus suggesting a role in wound healing. Defensins have also been shown to be chemotactic for monocytes, polymorphonuclear leucocytes and T-cells. In vitro defensins have been shown to be active against *E. coli*, *Listeria monocytogenes*, *Salmonella typhimurium* and *Candida albicans*.

Increasing knowledge of these proteins is therefore of extreme importance in increasing the understanding of the underlying pathways that lead to the disease states and associated disease states mentioned above, and in developing more effective gene and/or drug therapies to treat these disorders.

THE INVENTION

The invention is based on the discovery that the INSP108 and INSP109 polypeptides are defensins.

In one embodiment of the first aspect of the invention, there is provided a polypeptide which:
(i) comprises the amino acid sequence as recited in SEQ ID NO:2, SEQ ID NO:4, SEQ ID NO:6 and/or SEQ ID NO:8;
(ii) is a fragment thereof which functions as a member of the defensin family of proteins, or has an antigenic determinant in common with the polypeptides of (i); or
(iii) is a functional equivalent of (i) or (ii).

Preferably, the polypeptide according to this first aspect of the invention:
(i) comprises the amino acid sequence as recited in SEQ ID NO:6 and/or SEQ ID NO:8;
(ii) is a fragment thereof which functions as a member of the defensin family of proteins, or has an antigenic determinant in common with the polypeptides of (i); or
(iii) is a functional equivalent of (i) or (ii).

According to a second embodiment of this first aspect of the invention, there is provided a polypeptide which:
(i) consists of the amino acid sequence as recited in SEQ ID NO:2, SEQ ID NO:4, SEQ ID NO:6 and/or SEQ ID NO:8;
(ii) is a fragment thereof which functions as a member of the defensin family of proteins, or having an antigenic determinant in common with the polypeptides of (i); or
(iii) is a functional equivalent of (i) or (ii).

The polypeptide having the sequence recited in SEQ ID NO:2 is referred to hereafter as "INSP108 exon 1 polypeptide". The polypeptide having the sequence recited in SEQ ID NO:4 is referred to hereafter as "INSP108 exon 2 polypeptide". The polypeptide having the sequence recited in SEQ ID NO:6 is referred to hereafter as the "INSP108 polypeptide".

Although the Applicant does not wish to be bound by this theory, it is postulated that the first 24 amino acids of the INSP108 polypeptide form a signal peptide.

The full length INSP108 polypeptide sequences without this postulated signal sequence is recited in SEQ ID NO:8.

The polypeptide having the sequence recited in SEQ ID NO:8 is referred to hereafter as "the INSP108 mature polypeptide".

The term "INSP108 polypeptides" as used herein includes polypeptides comprising the INSP108 exon 1 polypeptide, the INSP108 exon 2 polypeptide, the INSP108 polypeptide and the INSP108 mature polypeptide.

In a third embodiment of the first aspect of the invention, there is provided a polypeptide which:
(i) comprises the amino acid sequence as recited in SEQ ID NO:10, SEQ ID NO:12, SEQ ID NO:14 and/or SEQ ID NO:16;
(ii) is a fragment thereof which functions as a member of the defensin family of proteins, or has an antigenic determinant in common with the polypeptides of (i); or
(iii) is a functional equivalent of (i) or (ii).

Preferably, the polypeptide according to this first aspect of the invention:
(i) comprises the amino acid sequence as recited in SEQ ID NO:14 and/or SEQ ID NO:16;
(ii) is a fragment thereof which functions as a member of the defensin family of proteins, or has an antigenic determinant in common with the polypeptides of (i); or
(iii) is a functional equivalent of (i) or (ii).

According to a fourth embodiment of this first aspect of the invention, there is provided a polypeptide which:
(i) consists of the amino acid sequence as recited in SEQ ID NO:10, SEQ ID NO:12, SEQ ID NO:14 and/or SEQ ID NO:16;
(ii) is a fragment thereof which functions as a member of the defensin family of proteins, or having an antigenic determinant in common with the polypeptides of (i); or
(iii) is a functional equivalent of (i) or (ii).

The polypeptide having the sequence recited in SEQ ID NO:10 is referred to hereafter as "INSP109 exon 1 polypeptide". The polypeptide having the sequence recited in SEQ ID NO:12 is referred to hereafter as "INSP109 exon 2 polypeptide". The polypeptide having the sequence recited in SEQ ID NO:14 is referred to hereafter as the "INSP109 polypeptide".

Although the Applicant does not wish to be bound by this theory, it is postulated that the first 21 amino acids of the INSP109 polypeptide form a signal peptide.

The full length INSP109 polypeptide sequences without this postulated signal sequence is recited in SEQ ID NO:16.

The polypeptide having the sequence recited in SEQ ID NO:16 is referred to hereafter as "the INSP109 mature polypeptide".

The term "INSP109 polypeptides" as used herein includes polypeptides comprising the INSP109 exon 1 polypeptide, the INSP109 exon 2 polypeptide, the INSP109 polypeptide and the INSP109 mature polypeptide.

By "functions as a member of the defensin family" we refer to polypeptides that comprise amino acid sequence or structural features that can be identified as conserved features within the polypeptides of the defensin family, such that the polypeptide's interaction with receptor or ligand is not substantially affected detrimentally in comparison to the function of the full length wild type polypeptide. In particular, we refer to the presence of cysteine residues in specific positions within the polypeptide that allow the formation of intra-domain disulphide bonds. Ability to function as a defensin may be measured using the assays described by Nizet et al. (Nature 2001, 414:454-457) and Cole et al. (Proc. Natl. Acad. Sci. 2002, 99(4):1813-1818).

In a second aspect, the invention provides a purified nucleic acid molecule which encodes a polypeptide of the first aspect of the invention.

Preferably, the purified nucleic acid molecule comprises the nucleic acid sequence as recited in SEQ ID NO:1 (encoding the INSP108 exon 1 polypeptide), SEQ ID NO:3 (encoding the INSP108 exon 2 polypeptide), SEQ ID NO:5 (encoding the INSP108 polypeptide), SEQ ID NO:7 (encoding the INSP108 mature polypeptide), SEQ ID NO:9 (encoding the INSP109 exon 1 polypeptide), SEQ ID NO:11 (encoding the INSP109 exon 2 polypeptide), SEQ ID NO:13 (encoding the INSP109 polypeptide) and/or SEQ ID NO:15 (encoding the INSP109 mature polypeptide) or is a redundant equivalent or fragment of any one of these sequences.

The invention further provides that the purified nucleic acid molecule consists of the nucleic acid sequence as recited in SEQ ID NO:1 (encoding the INSP108 exon 1 polypeptide), SEQ ID NO:3 (encoding the INSP108 exon 2 polypeptide), SEQ ID NO:5 (encoding the INSP108 polypeptide), SEQ ID NO:7 (encoding the INSP108 mature polypeptide), SEQ ID NO:9 (encoding the INSP109 exon 1 polypeptide), SEQ ID NO:11 (encoding the INSP109 exon 2 polypeptide), SEQ ID NO:13 (encoding the INSP109 polypeptide) and/or SEQ ID NO:15 (encoding the INSP109 mature polypeptide) or is a redundant equivalent or fragment of any one of these sequences.

In a third aspect, the invention provides a purified nucleic acid molecule which hybridizes under high stringency conditions with a nucleic acid molecule of the second aspect of the invention.

In a fourth aspect, the invention provides a vector, such as an expression vector, that contains a nucleic acid molecule of the second or third aspect of the invention.

In a fifth aspect, the invention provides a host cell transformed with a vector of the fourth aspect of the invention.

In a sixth aspect, the invention provides a ligand which binds specifically to protein members of the defensin family of the first aspect of the invention. Preferably, the ligand inhibits the function of a polypeptide of the first aspect of the invention which is a member of the defensin family of proteins. Ligands to a polypeptide according to the invention may come in various forms, including natural or modified substrates, enzymes, receptors, small organic molecules such as small natural or synthetic organic molecules of up to 2000 Da, preferably 800 Da or less, peptidomimetics, inorganic molecules, peptides, polypeptides, antibodies, structural or functional mimetics of the aforementioned.

In a seventh aspect, the invention provides a compound that is effective to alter the expression of a natural gene which encodes a polypeptide of the first aspect of the invention or to regulate the activity of a polypeptide of the first aspect of the invention.

A compound of the seventh aspect of the invention may either increase (agonise) or decrease (antagonise) the level of expression of the gene or the activity of the polypeptide.

Importantly, the identification of the functions of the INSP108 and INSP109 polypeptides allows for the design of screening methods capable of identifying compounds that are effective in the treatment and/or diagnosis of disease. Ligands and compounds according to the sixth and seventh aspects of the invention may be identified using such methods. These methods are included as aspects of the present invention.

In an eighth aspect, the invention provides a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, for use in therapy or diagnosis of diseases in which members of the defensin family are implicated. Such diseases may include cell proliferative disorders, including neoplasm, melanoma, lung, colorectal, breast, pancreas, head and neck and other solid tumours; myeloproliferative disorders, such as leukemia, non-Hodgkin lymphoma, leukopenia, thrombocytopenia, angiogenesis disorder, Kaposi' sarcoma; autoimmune/inflammatory disorders, including allergy, inflammatory bowel disease, arthritis, psoriasis and respiratory tract inflammation, asthma, and organ transplant rejection; cardiovascular disorders, including hypertension, oedema, angina, atherosclerosis, thrombosis, sepsis, shock, reperfusion injury, and ischemia; neurological disorders including central nervous system disease, Alzheimer's disease, brain injury, amyotrophic lateral sclerosis, and pain; developmental disorders; metabolic disorders including diabetes mellitus, osteoporosis, and obesity, AIDS and renal disease; infections including viral infection, bacterial infection, fungal infection and parasitic infection and other pathological conditions. Preferably, the disease is one in which the defensin family of proteins is implicated, such as sublethal endotoxaemia, septic shock, microbial infection of the amniotic cavity, Jarish-Herxheimer reaction of relapsing fever, infectious diseases of the central nervous system, acute pancreatitis, ulcerative colitis, empyaema, haemolytic uraemic syndrome, meningococcal disease, gastric infection, pertussis, peritonitis, psoriasis, rheumatoid arthritis, sepsis, asthma, HIV, AIDS and glomerulonephritis. These molecules may also be used in the manufacture of a medicament for the treatment of such diseases.

In a ninth aspect, the invention provides a method of diagnosing a disease in a patient, comprising assessing the level of expression of a natural gene encoding a polypeptide of the first aspect of the invention or the activity of a polypeptide of the first aspect of the invention in tissue from said patient and comparing said level of expression or activity to a control level, wherein a level that is different to said control level is indicative of disease. Such a method will preferably be carried out in vitro. Similar methods may be used for monitoring the therapeutic treatment of disease in a patient, wherein altering the level of expression or activity of a polypeptide or nucleic acid molecule over the period of time towards a control level is indicative of regression of disease.

A preferred method for detecting polypeptides of the first aspect of the invention comprises the steps of: (a) contacting a ligand, such as an antibody, of the sixth aspect of the invention with a biological sample under conditions suitable for the formation of a ligand-polypeptide complex; and (b) detecting said complex.

A number of different such methods according to the ninth aspect of the invention exist, as the skilled reader will be aware, such as methods of nucleic acid hybridization with short probes, point mutation analysis, polymerase chain reaction (PCR) amplification and methods using antibodies to detect aberrant protein levels. Similar methods may be used on a short or long term basis to allow therapeutic treatment of a disease to be monitored in a patient. The invention also provides kits that are useful in these methods for diagnosing disease.

In a tenth aspect, the invention provides for the use of a polypeptide of the first aspect of the invention as a defensin protein. Suitable uses of the polypeptides of the invention as defensin proteins include use as a regulator of cellular growth, metabolism or differentiation, use as part of a receptor/ligand pair and use as a diagnostic marker for a physiological or pathological condition selected from the list given above.

In an eleventh aspect, the invention provides a pharmaceutical composition comprising a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, in conjunction with a pharmaceutically-acceptable carrier.

In a twelfth aspect, the present invention provides a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, for use in the manufacture of a medicament for the diagnosis or treatment of a disease.

In a thirteenth aspect, the invention provides a method of treating a disease in a patient comprising administering to the patient a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention.

For diseases in which the expression of a natural gene encoding a polypeptide of the first aspect of the invention, or in which the activity of a polypeptide of the first aspect of the invention, is lower in a diseased patient when compared to the level of expression or activity in a healthy patient, the polypeptide, nucleic acid molecule, ligand or compound administered to the patient should be an agonist. Conversely, for diseases in which the expression of the natural gene or activity of the polypeptide is higher in a diseased patient when compared to the level of expression or activity in a healthy patient, the polypeptide, nucleic acid molecule, ligand or compound administered to the patient should be an antagonist. Examples of such antagonists include antisense nucleic acid molecules, ribozymes and ligands, such as antibodies.

In a fourteenth aspect, the invention provides transgenic or knockout non-human animals that have been transformed to express higher, lower or absent levels of a polypeptide of the first aspect of the invention. Such transgenic animals are very useful models for the study of disease and may also be used in screening regimes for the identification of compounds that are effective in the treatment or diagnosis of such a disease.

A summary of standard techniques and procedures which may be employed in order to utilise the invention is given below. It will be understood that this invention is not limited to the particular methodology, protocols, cell lines, vectors and reagents described. It is also to be understood that the terminology used herein is for the purpose of describing particular embodiments only and it is not intended that this terminology should limit the scope of the present invention. The extent of the invention is limited only by the terms of the appended claims.

Standard abbreviations for nucleotides and amino acids are used in this specification.

The practice of the present invention will employ, unless otherwise indicated, conventional techniques of molecular biology, microbiology, recombinant DNA technology and immunology, which are within the skill of those working in the art.

Such techniques are explained fully in the literature. Examples of particularly suitable texts for consultation include the following: Sambrook Molecular Cloning; A Laboratory Manual, Second Edition (1989); DNA Cloning, Volumes I and II (D. N Glover ed. 1985); Oligonucleotide Synthesis (M. J. Gait ed. 1984); Nucleic Acid Hybridization (B. D. Hames & S. J. Higgins eds. 1984); Transcription and Translation (B. D. Hames & S. J. Higgins eds. 1984); Animal Cell Culture (R. I. Freshney ed. 1986); Immobilized Cells and Enzymes (IRL Press, 1986); B. Perbal, A Practical Guide to Molecular Cloning (1984); the Methods in Enzymology series (Academic Press, Inc.), especially volumes 154 & 155; Gene Transfer Vectors for Mammalian Cells (J. H. Miller and M. P. Calos eds. 1987, Cold Spring Harbor Laboratory); Immunochemical Methods in Cell and Molecular Biology (Mayer and Walker, eds. 1987, Academic Press, London); Scopes, (1987) Protein Purification: Principles and Practice, Second Edition (Springer Verlag, N.Y.); and Handbook of Experimental Immunology, Volumes I-IV (D. M. Weir and C. C. Blackwell eds. 1986).

As used herein, the term "polypeptide" includes any peptide or protein comprising two or more amino acids joined to each other by peptide bonds or modified peptide bonds, i.e. peptide isosteres. This term refers both to short chains (peptides and oligopeptides) and to longer chains (proteins).

The polypeptide of the present invention may be in the form of a mature protein or may be a pre-, pro- or preproprotein that can be activated by cleavage of the pre-, pro- or prepro-portion to produce an active mature polypeptide. In such polypeptides, the pre-, pro- or prepro-sequence may be a leader or secretory sequence or may be a sequence that is employed for purification of the mature polypeptide sequence.

The polypeptide of the first aspect of the invention may form part of a fusion protein. For example, it is often advantageous to include one or more additional amino acid sequences which may contain secretory or leader sequences, pro-sequences, sequences which aid in purification, or sequences that confer higher protein stability, for example during recombinant production. Alternatively or additionally, the mature polypeptide may be fused with another compound, such as a compound to increase the half-life of the polypeptide (for example, polyethylene glycol).

Polypeptides may contain amino acids other than the 20 gene-encoded amino acids, modified either by natural processes, such as by post-translational processing or by chemical modification techniques which are well known in the art. Among the known modifications which may commonly be present in polypeptides of the present invention are glycosylation, lipid attachment, sulphation, gamma-carboxylation, for instance of glutamic acid residues, hydroxylation and ADP-ribosylation. Other potential modifications include acetylation, acylation, amidation, covalent attachment of flavin, covalent attachment of a haeme moiety, covalent attachment of a nucleotide or nucleotide derivative, covalent attachment of a lipid derivative, covalent attachment of phosphatidylinositol, cross-linking, cyclization, disulphide bond formation, demethylation, formation of covalent cross-links, formation of cysteine, formation of pyroglutamate, formylation, GPI anchor formation, iodination, methylation, myristoylation, oxidation, proteolytic processing, phosphorylation, prenylation, racemization, selenoylation, transfer-RNA mediated addition of amino acids to proteins such as arginylation, and ubiquitination.

Modifications can occur anywhere in a polypeptide, including the peptide backbone, the amino acid side-chains and the amino or carboxyl termini. In fact, blockage of the amino or carboxyl terminus in a polypeptide, or both, by a covalent modification is common in naturally-occurring and synthetic polypeptides and such modifications may be present in polypeptides of the present invention.

The modifications that occur in a polypeptide often will be a function of how the polypeptide is made. For polypeptides that are made recombinantly, the nature and extent of the modifications in large part will be determined by the post-translational modification capacity of the particular host cell and the modification signals that are present in the amino acid sequence of the polypeptide in question. For instance, glycosylation patterns vary between different types of host cell.

The polypeptides of the present invention can be prepared in any suitable manner. Such polypeptides include isolated naturally-occurring polypeptides (for example purified from cell culture), recombinantly-produced polypeptides (including fusion proteins), synthetically-produced polypeptides or polypeptides that are produced by a combination of these methods.

The functionally-equivalent polypeptides of the first aspect of the invention may be polypeptides that are homologous to the INSP108 or INSP109 polypeptides. Two polypeptides are said to be "homologous", as the term is used herein, if the sequence of one of the polypeptides has a high enough degree of identity or similarity to the sequence of the other polypeptide. "Identity" indicates that at any particular position in the aligned sequences, the amino acid residue is identical between the sequences. "Similarity" indicates that, at any particular position in the aligned sequences, the amino acid residue is of a similar type between the sequences. Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

Homologous polypeptides therefore include natural biological variants (for example, allelic variants or geographical variations within the species from which the polypeptides are derived) and mutants (such as mutants containing amino acid substitutions, insertions or deletions) of the INSP108 and INSP109 polypeptides. Such mutants may include polypeptides in which one or more of the amino acid residues are substituted with a conserved or non-conserved amino acid residue (preferably a conserved amino acid residue) and such substituted amino acid residue may or may not be one encoded by the genetic code. Typical such substitutions are among Ala, Val, Leu and Ile; among Ser and Thr; among the acidic residues Asp and Glu; among Asn and Gln; among the basic residues Lys and Arg; or among the aromatic residues Phe and Tyr. Particularly preferred are variants in which several, i.e. between 5 and 10, 1 and 5, 1 and 3, 1 and 2 or just 1 amino acids are substituted, deleted or added in any combination. Especially preferred are silent substitutions, additions and deletions, which do not alter the properties and activities of the protein. Also especially preferred in this regard are conservative substitutions. Such mutants also include polypeptides in which one or more of the amino acid residues includes a substituent group.

Typically, greater than 30% identity between two polypeptides is considered to be an indication of functional equivalence. Preferably, functionally equivalent polypeptides of the first aspect of the invention have a degree of sequence identity with the INSP108 and INSP109 polypeptides, or with active fragments thereof, of greater than 80%. More preferred polypeptides have degrees of identity of greater than 85%, 90%, 95%, 98% or 99%, respectively.

The functionally-equivalent polypeptides of the first aspect of the invention may also be polypeptides which have been identified using one or more techniques of structural alignment. For example, the Inpharmatica Genome Threader technology that forms one aspect of the search tools used to generate the Biopendium™ search database may be used (see PCT application WO 01/69507) to identify polypeptides of presently-unknown function which, while having low sequence identity as compared to the INSP108 and INSP109 polypeptides, are predicted to be members of the defensin family, by virtue of sharing significant structural homology with the INSP108 and INSP109 polypeptide sequences. By "significant structural homology" is meant that the Inpharmatica Genome Threader predicts two proteins to share structural homology with a certainty of 10% and above.

The polypeptides of the first aspect of the invention also include fragments of the INSP108 or INSP109 polypeptides and fragments of the functional equivalents of the INSP108 or INSP109 polypeptides, provided that those fragments are members of the defensin family or have an antigenic determinant in common with the INSP108 or INSP109 polypeptides.

As used herein, the term "fragment" refers to a polypeptide having an amino acid sequence that is the same as part, but not all, of the amino acid sequence of the INSP108 or INSP109 polypeptides or one of their functional equivalents. The fragments should comprise at least n consecutive amino acids from the sequence and, depending on the particular sequence, n preferably is 7 or more (for example, 8, 10, 12, 14, 16, 18, 20 or more). Small fragments may form an antigenic determinant.

Fragments of the full length INSP108 and INSP109 polypeptides may consist of combinations of 1 or 2 of neighbouring exon sequences in the INSP108 or INSP109 polypeptide sequences, respectively. For example, such combinations include exons 1 and 2 of the INSP108 polypeptide. Such fragments are included in the present invention.

Such fragments may be "free-standing", i.e. not part of or fused to other amino acids or polypeptides, or they may be comprised within a larger polypeptide of which they form a part or region. When comprised within a larger polypeptide, the fragment of the invention most preferably forms a single continuous region. For instance, certain preferred embodiments relate to a fragment having a pre- and/or pro-polypeptide region fused to the amino terminus of the fragment and/or an additional region fused to the carboxyl terminus of the fragment. However, several fragments may be comprised within a single larger polypeptide.

The polypeptides of the present invention or their immunogenic fragments (comprising at least one antigenic determinant) can be used to generate ligands, such as polyclonal or monoclonal antibodies, that are immunospecific for the polypeptides. Such antibodies may be employed to isolate or to identify clones expressing the polypeptides of the invention or to purify the polypeptides by affinity chromatography. The antibodies may also be employed as diagnostic or therapeutic aids, amongst other applications, as will be apparent to the skilled reader.

The term "immunospecific" means that the antibodies have substantially greater affinity for the polypeptides of the invention than their affinity for other related polypeptides in the prior art. As used herein, the term "antibody" refers to intact molecules as well as to fragments thereof, such as Fab, F(ab')2 and Fv, which are capable of binding to the antigenic determinant in question. Such antibodies thus bind to the polypeptides of the first aspect of the invention.

By "substantially greater affinity" we mean that there is a measurable increase in the affinity for a polypeptide of the invention as compared with the affinity for known secreted proteins.

Preferably, the affinity is at least 1.5-fold, 2-fold, 5-fold 10-fold, 100-fold, $10^3$-fold, $10^4$-fold, $10^5$-fold, $10^6$-fold or greater for a polypeptide of the invention than for known secreted proteins such as members of the defensin family of proteins.

If polyclonal antibodies are desired, a selected mammal, such as a mouse, rabbit, goat or horse, may be immunised with a polypeptide of the first aspect of the invention. The polypeptide used to immunise the animal can be derived by recombinant DNA technology or can be synthesized chemically. If desired, the polypeptide can be conjugated to a carrier protein. Commonly used carriers to which the polypeptides may be chemically coupled include bovine serum albumin, thyroglobulin and keyhole limpet haemocyanin. The coupled polypeptide is then used to immunise the animal. Serum from the immunised animal is collected and treated according to known procedures, for example by immunoaffinity chromatography.

Monoclonal antibodies to the polypeptides of the first aspect of the invention can also be readily produced by one skilled in the art. The general methodology for making monoclonal antibodies using hybridoma technology is well known (see, for example, Kohler, G. and Milstein, C., Nature 256: 495-497 (1975); Kozbor et al., Immunology Today 4: 72 (1983); Cole et al., 77-96 in Monoclonal Antibodies and Cancer Therapy, Alan R. Liss, Inc. (1985).

Panels of monoclonal antibodies produced against the polypeptides of the first aspect of the invention can be screened for various properties, i.e., for isotype, epitope, affinity, etc. Monoclonal antibodies are particularly useful in purification of the individual polypeptides against which they are directed. Alternatively, genes encoding the monoclonal antibodies of interest may be isolated from hybridomas, for instance by PCR techniques known in the art, and cloned and expressed in appropriate vectors.

Chimeric antibodies, in which non-human variable regions are joined or fused to human constant regions (see, for example, Liu et al., Proc. Natl. Acad. Sci. USA, 84, 3439 (1987)), may also be of use.

The antibody may be modified to make it less immunogenic in an individual, for example by humanisation (see Jones et al., Nature, 321, 522 (1986); Verhoeyen et al., Science, 239, 1534 (1988); Kabat et al., J. Immunol., 147, 1709 (1991); Queen et al., Proc. Natl. Acad. Sci. USA, 86, 10029 (1989); Gorman et al., Proc. Natl. Acad. Sci. USA, 88, 34181 (1991); and Hodgson et al., Bio/Technology, 9, 421 (1991)). The term "humanised antibody", as used herein, refers to antibody molecules in which the CDR amino acids and selected other amino acids in the variable domains of the heavy and/or light chains of a non-human donor antibody have been substituted in place of the equivalent amino acids in a human antibody. The humanised antibody thus closely resembles a human antibody but has the binding ability of the donor antibody.

In a further alternative, the antibody may be a "bispecific" antibody, that is an antibody having two different antigen binding domains, each domain being directed against a different epitope.

Phage display technology may be utilised to select genes which encode antibodies with binding activities towards the polypeptides of the invention either from repertoires of PCR amplified V-genes of lymphocytes from humans screened for possessing the relevant antibodies, or from naive libraries (McCafferty, J. et al., (1990), Nature 348, 552-554; Marks, J. et al., (1992) Biotechnology 10, 779-783). The affinity of these antibodies can also be improved by chain shuffling (Clackson, T. et al., (1991) Nature 352, 624-628).

Antibodies generated by the above techniques, whether polyclonal or monoclonal, have additional utility in that they may be employed as reagents in immunoassays, radioimmunoassays (RIA) or enzyme-linked immunosorbent assays (ELISA). In these applications, the antibodies can be labelled with an analytically-detectable reagent such as a radioisotope, a fluorescent molecule or an enzyme.

Preferred nucleic acid molecules of the second and third aspects of the invention are those which encode a polypeptide sequence as recited in SEQ ID NO:2, SEQ ID NO:4, SEQ ID NO:6, SEQ ID NO:8, SEQ ID NO:10, SEQ ID NO:12, SEQ ID NO:14 and SEQ ID NO:16 and functionally equivalent polypeptides. These nucleic acid molecules may be used in the methods and applications described herein. The nucleic acid molecules of the invention preferably comprise at least n consecutive nucleotides from the sequences disclosed herein where, depending on the particular sequence, n is 10 or more (for example, 12, 14, 15, 18, 20, 25, 30, 35, 40 or more).

The nucleic acid molecules of the invention also include sequences that are complementary to nucleic acid molecules described above (for example, for antisense or probing purposes).

Nucleic acid molecules of the present invention may be in the form of RNA, such as mRNA, or in the form of DNA, including, for instance cDNA, synthetic DNA or genomic DNA. Such nucleic acid molecules may be obtained by cloning, by chemical synthetic techniques or by a combination thereof. The nucleic acid molecules can be prepared, for example, by chemical synthesis using techniques such as solid phase phosphoramidite chemical synthesis, from genomic or cDNA libraries or by separation from an organism. RNA molecules may generally be generated by the in vitro or in vivo transcription of DNA sequences.

The nucleic acid molecules may be double-stranded or single-stranded. Single-stranded DNA may be the coding strand, also known as the sense strand, or it may be the non-coding strand, also referred to as the anti-sense strand.

The term "nucleic acid molecule" also includes analogues of DNA and RNA, such as those containing modified backbones, and peptide nucleic acids (PNA). The term "PNA", as used herein, refers to an antisense molecule or an anti-gene agent which comprises an oligonucleotide of at least five nucleotides in length linked to a peptide backbone of amino acid residues, which preferably ends in lysine. The terminal lysine confers solubility to the composition. PNAs may be pegylated to extend their lifespan in a cell, where they preferentially bind complementary single stranded DNA and RNA and stop transcript elongation (Nielsen, P. E. et al. (1993) Anticancer Drug Des. 8:53-63).

A nucleic acid molecule which encodes a polypeptide of this invention may be identical to the coding sequence of one or more of the nucleic acid molecules disclosed herein.

These molecules also may have a different sequence which, as a result of the degeneracy of the genetic code, encodes a polypeptide as recited in SEQ ID NO:2, SEQ ID NO:4, SEQ ID NO:6, SEQ ID NO:8, SEQ ID NO:10, SEQ ID NO:12, SEQ ID NO:14 or SEQ ID NO:16. Such nucleic acid molecules may include, but are not limited to, the coding sequence for the mature polypeptide by itself; the coding sequence for the mature polypeptide and additional coding sequences, such as those encoding a leader or secretory sequence, such as a pro-, pre- or prepro-polypeptide sequence; the coding sequence of the mature polypeptide, with or without the aforementioned additional coding sequences, together with further additional, non-coding sequences, including non-coding 5' and 3' sequences, such as the transcribed, non-translated sequences that play a role in transcription (including termination signals), ribosome binding and mRNA stability. The nucleic acid molecules may also include additional sequences which encode additional amino acids, such as those which provide additional functionalities.

The nucleic acid molecules of the second and third aspects of the invention may also encode the fragments or the functional equivalents of the polypeptides and fragments of the first aspect of the invention. Such a nucleic acid molecule may be a naturally-occurring variant such as a naturally-occurring allelic variant, or the molecule may be a variant that is not known to occur naturally. Such non-naturally occurring variants of the nucleic acid molecule may be made by mutagenesis techniques, including those applied to nucleic acid molecules, cells or organisms.

Among variants in this regard are variants that differ from the aforementioned nucleic acid molecules by nucleotide substitutions, deletions or insertions. The substitutions, deletions or insertions may involve one or more nucleotides. The variants may be altered in coding or non-coding regions or both. Alterations in the coding regions may produce conservative or non-conservative amino acid substitutions, deletions or insertions.

The nucleic acid molecules of the invention can also be engineered, using methods generally known in the art, for a variety of reasons, including modifying the cloning, processing, and/or expression of the gene product (the polypeptide). DNA shuffling by random fragmentation and PCR reassembly of gene fragments and synthetic oligonucleotides are included as techniques which may be used to engineer the nucleotide sequences. Site-directed mutagenesis may be used to insert new restriction sites, alter glycosylation patterns, change codon preference, produce splice variants, introduce mutations and so forth.

Nucleic acid molecules which encode a polypeptide of the first aspect of the invention may be ligated to a heterologous sequence so that the combined nucleic acid molecule encodes a fusion protein. Such combined nucleic acid molecules are included within the second or third aspects of the invention. For example, to screen peptide libraries for inhibitors of the activity of the polypeptide, it may be useful to express, using such a combined nucleic acid molecule, a fusion protein that can be recognised by a commercially-available antibody. A fusion protein may also be engineered to contain a cleavage site located between the sequence of the polypeptide of the invention and the sequence of a heterologous protein so that the polypeptide may be cleaved and purified away from the heterologous protein.

The nucleic acid molecules of the invention also include antisense molecules that are partially complementary to nucleic acid molecules encoding polypeptides of the present invention and that therefore hybridize to the encoding nucleic acid molecules (hybridization). Such antisense molecules, such as oligonucleotides, can be designed to recognise, specifically bind to and prevent transcription of a target nucleic acid encoding a polypeptide of the invention, as will be known by those of ordinary skill in the art (see, for example, Cohen, J. S., Trends in Pharm. Sci., 10, 435 (1989), Okano, J. Neurochem. 56, 560 (1991); O'Connor, J. Neurochem 56, 560 (1991); Lee et al., Nucleic Acids Res 6, 3073 (1979); Cooney et al., Science 241, 456 (1988); Dervan et al., Science 251, 1360 (1991).

The term "hybridization" as used here refers to the association of two nucleic acid molecules with one another by hydrogen bonding. Typically, one molecule will be fixed to a solid support and the other will be free in solution. Then, the two molecules may be placed in contact with one another under conditions that favour hydrogen bonding. Factors that affect this bonding include: the type and volume of solvent; reaction temperature; time of hybridization; agitation; agents to block the non-specific attachment of the liquid phase molecule to the solid support (Denhardt's reagent or BLOTTO); the concentration of the molecules; use of compounds to increase the rate of association of molecules (dextran sulphate or polyethylene glycol); and the stringency of the washing conditions following hybridization (see Sambrook et al. [supra]).

The inhibition of hybridization of a completely complementary molecule to a target molecule may be examined using a hybridization assay, as known in the art (see, for example, Sambrook et al. [supra]). A substantially homologous molecule will then compete for and inhibit the binding of a completely homologous molecule to the target molecule under various conditions of stringency, as taught in Wahl, G. M. and S. L. Berger (1987; Methods Enzymol. 152:399-407) and Kimmel, A. R. (1987; Methods Enzymol. 152:507-511).

"Stringency" refers to conditions in a hybridization reaction that favour the association of very similar molecules over association of molecules that differ. High stringency hybridisation conditions are defined as overnight incubation at 42° C. in a solution comprising 50% formamide, 5×SSC (150 mM NaCl, 15 mM trisodium citrate), 50 mM sodium phosphate (pH7.6), 5×Denhardts solution, 10% dextran sulphate, and 20 microgram/ml denatured, sheared salmon sperm DNA, followed by washing the filters in 0.1×SSC at approximately 65° C. Low stringency conditions involve the hybridisation reaction being carried out at 35° C. (see Sambrook et al. [supra]). Preferably, the conditions used for hybridization are those of high stringency.

Preferred embodiments of this aspect of the invention are nucleic acid molecules that are at least 70% identical over their entire length to a nucleic acid molecule encoding the INSP108 or INSP109 polypeptides and nucleic acid molecules that are substantially complementary to such nucleic acid molecules. Preferably, a nucleic acid molecule according to this aspect of the invention comprises a region that is at least 80% identical over its entire length to such coding sequences, or is a nucleic acid molecule that is complementary thereto. In this regard, nucleic acid molecules at least 90%, preferably at least 95%, more preferably at least 98%, 99% or more identical over their entire length to the same are particularly preferred. Preferred embodiments in this respect are nucleic acid molecules that encode polypeptides which retain substantially the same biological function or activity as the INSP108 or INSP109 polypeptides.

The invention also provides a process for detecting a nucleic acid molecule of the invention, comprising the steps of: (a) contacting a nucleic probe according to the invention with a biological sample under hybridizing conditions to form duplexes; and (b) detecting any such duplexes that are formed.

As discussed additionally below in connection with assays that may be utilised according to the invention, a nucleic acid molecule as described above may be used as a hybridization probe for RNA, cDNA or genomic DNA, in order to isolate full-length cDNAs and genomic clones encoding the INSP108 or INSP109 polypeptides and to isolate cDNA and genomic clones of homologous or orthologous genes that have a high sequence similarity to the gene encoding this polypeptide.

In this regard, the following techniques, among others known in the art, may be utilised and are discussed below for purposes of illustration. Methods for DNA sequencing and analysis are well known and are generally available in the art and may, indeed, be used to practice many of the embodiments of the invention discussed herein. Such methods may employ such enzymes as the Klenow fragment of DNA polymerase I, Sequenase (US Biochemical Corp, Cleveland, Ohio), Taq polymerase (Perkin Elmer), thermostable T7 polymerase (Amersham, Chicago, Ill.), or combinations of polymerases and proof-reading exonucleases such as those found in the ELONGASE Amplification System marketed by Gibco/BRL (Gaithersburg, Md.). Preferably, the sequencing process may be automated using machines such as the Hamilton Micro Lab 2200 (Hamilton, Reno, Nev.), the Peltier Thermal Cycler (PTC200; MJ Research, Watertown, Mass.) and the ABI Catalyst and 373 and 377 DNA Sequencers (Perkin Elmer).

One method for isolating a nucleic acid molecule encoding a polypeptide with an equivalent function to that of the INSP108 polypeptide is to probe a genomic or cDNA library with a natural or artificially-designed probe using standard procedures that are recognised in the art (see, for example, "Current Protocols in Molecular Biology", Ausubel et al. (eds). Greene Publishing Association and John Wiley Interscience, New York, 1989, 1992). Probes comprising at least 15, preferably at least 30, and more preferably at least 50, contiguous bases that correspond to, or are complementary to, nucleic acid sequences from the appropriate encoding gene (SEQ ID NO:1, SEQ ID NO:3, SEQ ID NO:5, SEQ ID NO:7, SEQ ID NO:9, SEQ ID NO:11, SEQ ID NO:13 and SEQ ID NO:15), are particularly useful probes. Such probes may be labelled with an analytically-detectable reagent to facilitate their identification. Useful reagents include, but are not limited to, radioisotopes, fluorescent dyes and enzymes that are capable of catalysing the formation of a detectable product. Using these probes, the ordinarily skilled artisan will be capable of isolating complementary copies of genomic DNA, cDNA or RNA polynucleotides encoding proteins of interest from human, mammalian or other animal sources and screening such sources for related sequences, for example, for additional members of the family, type and/or subtype.

In many cases, isolated cDNA sequences will be incomplete, in that the region encoding the polypeptide will be cut short, normally at the 5' end. Several methods are available to obtain full length cDNAs, or to extend short cDNAs. Such sequences may be extended utilising a partial nucleotide sequence and employing various methods known in the art to detect upstream sequences such as promoters and regulatory elements. For example, one method which may be employed is based on the method of Rapid Amplification of cDNA Ends (RACE; see, for example, Frohman et al., PNAS USA 85, 8998-9002, 1988). Recent modifications of this technique, exemplified by the Marathon™ technology (Clontech Laboratories Inc.), for example, have significantly simplified the search for longer cDNAs. A slightly different technique, termed "restriction-site" PCR, uses universal primers to retrieve unknown nucleic acid sequence adjacent a known locus (Sarkar, G. (1993) PCR Methods Applic. 2:318-322). Inverse PCR may also be used to amplify or to extend sequences using divergent primers based on a known region (Triglia, T. et al. (1988) Nucleic Acids Res. 16:8186). Another method which may be used is capture PCR which involves PCR amplification of DNA fragments adjacent a known sequence in human and yeast artificial chromosome DNA (Lagerstrom, M. et al. (1991) PCR Methods Applic., 1, 111-119). Another method which may be used to retrieve unknown sequences is that of Parker, J. D. et al. (1991); Nucleic Acids Res. 19:3055-3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences that contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

In one embodiment of the invention, the nucleic acid molecules of the present invention may be used for chromosome localisation. In this technique, a nucleic acid molecule is specifically targeted to, and can hybridize with, a particular location on an individual human chromosome. The mapping of relevant sequences to chromosomes according to the present invention is an important step in the confirmatory correlation of those sequences with the gene-associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationships between genes and diseases that have been mapped to the same chromosomal region are then identified through linkage analysis (coinheritance of physically adjacent genes). This provides valuable information to investigators searching for disease genes using positional cloning or other gene discovery techniques. Once the disease or syndrome has been crudely localised by genetic linkage to a particular genomic region, any sequences mapping to that area may represent associated or regulatory genes for further investigation. The nucleic acid molecule may also be used to detect differences in the chromosomal location due to translocation, inversion, etc. among normal, carrier, or affected individuals.

The nucleic acid molecules of the present invention are also valuable for tissue localisation. Such techniques allow the determination of expression patterns of the polypeptide in tissues by detection of the mRNAs that encode them. These techniques include in situ hybridization techniques and nucleotide amplification techniques, such as PCR. Results from these studies provide an indication of the normal functions of the polypeptide in the organism. In addition, comparative studies of the normal expression pattern of mRNAs with that of mRNAs encoded by a mutant gene provide valuable insights into the role of mutant polypeptides in disease. Such inappropriate expression may be of a temporal, spatial or quantitative nature.

Gene silencing approaches may also be undertaken to down-regulate endogenous expression of a gene encoding a polypeptide of the invention. RNA interference (RNAi) (Elbashir, S M et al., Nature 2001, 411, 494-498) is one method of sequence specific post-transcriptional gene silencing that may be employed. Short dsRNA oligonucleotides are synthesised in vitro and introduced into a cell. The sequence specific binding of these dsRNA oligonucleotides triggers the degradation of target mRNA, reducing or ablating target protein expression.

Efficacy of the gene silencing approaches assessed above may be assessed through the measurement of polypeptide expression (for example, by Western blotting), and at the RNA level using TaqMan-based methodologies.

The vectors of the present invention comprise nucleic acid molecules of the invention and may be cloning or expression vectors. The host cells of the invention, which may be transformed, transfected or transduced with the vectors of the invention may be prokaryotic or eukaryotic.

The polypeptides of the invention may be prepared in recombinant form by expression of their encoding nucleic acid molecules in vectors contained within a host cell. Such expression methods are well known to those of skill in the art and many are described in detail by Sambrook et al. (supra) and Fernandez & Hoeffler (1998, eds. "Gene expression systems. Using nature for the art of expression". Academic Press, San Diego, London, Boston, New York, Sydney, Tokyo, Toronto).

Generally, any system or vector that is suitable to maintain, propagate or express nucleic acid molecules to produce a polypeptide in the required host may be used. The appropriate nucleotide sequence may be inserted into an expression system by any of a variety of well-known and routine techniques, such as, for example, those described in Sambrook et al., (supra). Generally, the encoding gene can be placed under the control of a control element such as a promoter, ribosome binding site (for bacterial expression) and, optionally, an operator, so that the DNA sequence encoding the desired polypeptide is transcribed into RNA in the transformed host cell.

Examples of suitable expression systems include, for example, chromosomal, episomal and virus-derived systems, including, for example, vectors derived from: bacterial plasmids, bacteriophage, transposons, yeast episomes, insertion elements, yeast chromosomal elements, viruses such as baculoviruses, papova viruses such as SV40, vaccinia viruses, adenoviruses, fowl pox viruses, pseudorabies viruses and retroviruses, or combinations thereof, such as those derived from plasmid and bacteriophage genetic elements, including cosmids and phagemids. Human artificial chromosomes (HACs) may also be employed to deliver larger fragments of DNA than can be contained and expressed in a plasmid. The vectors pCR4-TOPO-INSP108 (FIG. 9), pDONR-INSP108-6HIS (FIG. 13), pEAK12d-INSP108-6HIS (FIG. 14), pDEST12.2-INSP108-6HIS (FIG. 15), pCR4-TOPO-INSP109 (FIG. 19), pDONR-INSP109-6HIS (FIG. 20), pEAK12d-INSP109-6HIS (FIG. 21) and pDEST12.2-INSP109-6HIS (FIG. 22), are preferred examples of suitable vectors for use in accordance with the aspects of this invention relating to INSP108 and INSP109.

Particularly suitable expression systems include microorganisms such as bacteria transformed with recombinant bacteriophage, plasmid or cosmid DNA expression vectors; yeast transformed with yeast expression vectors; insect cell systems infected with virus expression vectors (for example, baculovirus); plant cell systems transformed with virus expression vectors (for example, cauliflower mosaic virus, CaMV; tobacco mosaic virus, TMV) or with bacterial expression vectors (for example, Ti or pBR322 plasmids); or animal cell systems. Cell-free translation systems can also be employed to produce the polypeptides of the invention.

Introduction of nucleic acid molecules encoding a polypeptide of the present invention into host cells can be effected by methods described in many standard laboratory manuals, such as Davis et al., Basic Methods in Molecular Biology (1986) and Sambrook et al., (supra). Particularly suitable methods include calcium phosphate transfection, DEAE-dextran mediated transfection, transfection, microinjection, cationic lipid-mediated transfection, electroporation, transduction, scrape loading, ballistic introduction or infection (see Sambrook et al., 1989 [supra]; Ausubel et al, 1991 [supra]; Spector, Goldman & Leinwald, 1998). In eukaryotic cells, expression systems may either be transient (for example, episomal) or permanent (chromosomal integration) according to the needs of the system.

The encoding nucleic acid molecule may or may not include a sequence encoding a control sequence, such as a signal peptide or leader sequence, as desired, for example, for secretion of the translated polypeptide into the lumen of the endoplasmic reticulum, into the periplasmic space or into the extracellular environment. These signals may be endogenous to the polypeptide or they may be heterologous signals. Leader sequences can be removed by the bacterial host in post-translational processing.

In addition to control sequences, it may be desirable to add regulatory sequences that allow for regulation of the expression of the polypeptide relative to the growth of the host cell. Examples of regulatory sequences are those which cause the expression of a gene to be increased or decreased in response to a chemical or physical stimulus, including the presence of a regulatory compound or to various temperature or metabolic conditions. Regulatory sequences are those non-translated regions of the vector, such as enhancers, promoters and 5' and 3' untranslated regions. These interact with host cellular proteins to carry out transcription and translation. Such regulatory sequences may vary in their strength and specificity. Depending on the vector system and host utilised, any number of suitable transcription and translation elements, including constitutive and inducible promoters, may be used. For example, when cloning in bacterial systems, inducible promoters such as the hybrid lacZ promoter of the Bluescript phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (for example, heat shock, RUBISCO and storage protein genes) or from plant viruses (for example, viral promoters or leader sequences) may be cloned into the vector. In mammalian cell systems, promoters from mammalian genes or from mammalian viruses are preferable. If it is necessary to generate a cell line that contains multiple copies of the sequence, vectors based on SV40 or EBV may be used with an appropriate selectable marker.

An expression vector is constructed so that the particular nucleic acid coding sequence is located in the vector with the appropriate regulatory sequences, the positioning and orientation of the coding sequence with respect to the regulatory sequences being such that the coding sequence is transcribed under the "control" of the regulatory sequences, i.e., RNA polymerase which binds to the DNA molecule at the control sequences transcribes the coding sequence. In some cases it may be necessary to modify the sequence so that it may be attached to the control sequences with the appropriate orientation; i.e., to maintain the reading frame.

The control sequences and other regulatory sequences may be ligated to the nucleic acid coding sequence prior to insertion into a vector. Alternatively, the coding sequence can be cloned directly into an expression vector that already contains the control sequences and an appropriate restriction site.

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Bowes melanoma and human hepatocellular carcinoma (for example Hep G2) cells and a number of other cell lines.

In the baculovirus system, the materials for baculovirus/insect cell expression systems are commercially available in kit form from, inter alia, Invitrogen, San Diego Calif. (the "MaxBac" kit). These techniques are generally known to those skilled in the art and are described fully in Summers and Smith, Texas Agricultural Experiment Station Bulletin No. 1555 (1987). Particularly suitable host cells for use in this system include insect cells such as *Drosophila* S2 and *Spodoptera* Sf9 cells.

There are many plant cell culture and whole plant genetic expression systems known in the art. Examples of suitable plant cellular genetic expression systems include those described in U.S. Pat. No. 5,693,506; U.S. Pat. No. 5,659,122; and U.S. Pat. No. 5,608,143. Additional examples of genetic expression in plant cell culture has been described by Zenk, Phytochemistry 30, 3861-3863 (1991).

In particular, all plants from which protoplasts can be isolated and cultured to give whole regenerated plants can be utilised, so that whole plants are recovered which contain the transferred gene. Practically all plants can be regenerated from cultured cells or tissues, including but not limited to all major species of sugar cane, sugar beet, cotton, fruit and other trees, legumes and vegetables.

Examples of particularly preferred bacterial host cells include streptococci, staphylococci, *E. coli, Streptomyces* and *Bacillus subtilis* cells.

Examples of particularly suitable host cells for fungal expression include yeast cells (for example, *S. cerevisiae*) and *Aspergillus* cells.

Any number of selection systems are known in the art that may be used to recover transformed cell lines. Examples include the herpes simplex virus thymidine kinase (Wigler, M. et al. (1977) Cell 11:223-32) and adenine phosphoribosyltransferase (Lowy, I. et al. (1980) Cell 22:817-23) genes that can be employed in tk⁻ or aprt⁺ cells, respectively.

Also, antimetabolite, antibiotic or herbicide resistance can be used as the basis for selection; for example, dihydrofolate reductase (DHFR) that confers resistance to methotrexate (Wigler, M. et al. (1980) Proc. Natl. Acad. Sci. 77:3567-70); npt, which confers resistance to the aminoglycosides neomycin and G-418 (Colbere-Garapin, F. et al. (1981) J. Mol. Biol. 150:1-14) and als or pat, which confer resistance to chlorsulfuron and phosphinotricin acetyltransferase, respectively. Additional selectable genes have been described, examples of which will be clear to those of skill in the art.

Although the presence or absence of marker gene expression suggests that the gene of interest is also present, its presence and expression may need to be confirmed. For example, if the relevant sequence is inserted within a marker gene sequence, transformed cells containing the appropriate sequences can be identified by the absence of marker gene function. Alternatively, a marker gene can be placed in tandem with a sequence encoding a polypeptide of the invention under the control of a single promoter. Expression of the marker gene in response to induction or selection usually indicates expression of the tandem gene as well.

Alternatively, host cells that contain a nucleic acid sequence encoding a polypeptide of the invention and which express said polypeptide may be identified by a variety of procedures known to those of skill in the art. These procedures include, but are not limited to, DNA-DNA or DNA-RNA hybridizations and protein bioassays, for example, fluorescence activated cell sorting (FACS) or immunoassay techniques (such as the enzyme-linked immunosorbent assay [ELISA] and radioimmunoassay [RIA]), that include membrane, solution, or chip based technologies for the detection and/or quantification of nucleic acid or protein (see Hampton, R. et al. (1990) Serological Methods, a Laboratory Manual, APS Press, St Paul, Minn.) and Maddox, D. E. et al. (1983) J. Exp. Med, 158, 1211-1216).

A wide variety of labels and conjugation techniques are known by those skilled in the art and may be used in various nucleic acid and amino acid assays. Means for producing labelled hybridization or PCR probes for detecting sequences related to nucleic acid molecules encoding polypeptides of the present invention include oligolabelling, nick translation, end-labelling or PCR amplification using a labelled polynucleotide.

Alternatively, the sequences encoding the polypeptide of the invention may be cloned into a vector for the production of an mRNA probe. Such vectors are known in the art, are commercially available, and may be used to synthesise RNA probes in vitro by addition of an appropriate RNA polymerase such as T7, T3 or SP6 and labelled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio)).

Suitable reporter molecules or labels, which may be used for ease of detection, include radionuclides, enzymes and fluorescent, chemiluminescent or chromogenic agents as well as substrates, cofactors, inhibitors, magnetic particles, and the like.

Nucleic acid molecules according to the present invention may also be used to create transgenic animals, particularly rodent animals. Such transgenic animals form a further aspect of the present invention. This may be done locally by modification of somatic cells, or by germ line therapy to incorporate heritable modifications. Such transgenic animals may be particularly useful in the generation of animal models for drug molecules effective as modulators of the polypeptides of the present invention.

The polypeptide can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography is particularly useful for purification. Well known techniques for refolding proteins may be employed to regenerate an active conformation when the polypeptide is denatured during isolation and or purification.

Specialised vector constructions may also be used to facilitate purification of proteins, as desired, by joining sequences encoding the polypeptides of the invention to a nucleotide sequence encoding a polypeptide domain that will facilitate purification of soluble proteins. Examples of such purification-facilitating domains include metal chelating peptides such as histidine-tryptophan modules that allow purification on immobilised metals, protein A domains that allow purification on immobilised immunoglobulin, and the domain utilised in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and the polypeptide of the invention may be used to facilitate purification. One such expression vector provides for expression of a fusion protein containing the polypeptide of the invention fused to several histidine residues preceding a thioredoxin or an enterokinase cleavage site. The histidine residues facilitate purification by IMAC (immobilised metal ion affinity chromatography as described in Porath, J. et al. (1992), Prot. Exp. Purif. 3: 263-281) while the thioredoxin or enterokinase cleavage site provides a means for purifying the polypeptide from the fusion protein. A discussion of vectors which contain fusion proteins is provided in Kroll, D. J. et al. (1993; DNA Cell Biol. 12:441-453).

If the polypeptide is to be expressed for use in screening assays, generally it is preferred that it be produced at the surface of the host cell in which it is expressed. In this event, the host cells may be harvested prior to use in the screening assay, for example using techniques such as fluorescence activated cell sorting (FACS) or immunoaffinity techniques. If the polypeptide is secreted into the medium, the medium can be recovered in order to recover and purify the expressed polypeptide. If polypeptide is produced intracellularly, the cells must first be lysed before the polypeptide is recovered.

The polypeptide of the invention can be used to screen libraries of compounds in any of a variety of drug screening techniques. Such compounds may activate (agonise) or inhibit (antagonise) the level of expression of the gene or the activity of the polypeptide of the invention and form a further aspect of the present invention. Preferred compounds are effective to alter the expression of a natural gene which encodes a polypeptide of the first aspect of the invention or to regulate the activity of a polypeptide of the first aspect of the invention.

Agonist or antagonist compounds may be isolated from, for example, cells, cell-free preparations, chemical libraries or natural product mixtures. These agonists or antagonists may be natural or modified substrates, ligands, enzymes, receptors or structural or functional mimetics. For a suitable review of such screening techniques, see Coligan et al., Current Protocols in Immunology 1(2):Chapter 5 (1991).

Compounds that are most likely to be good antagonists are molecules that bind to the polypeptide of the invention without inducing the biological effects of the polypeptide upon binding to it. Potential antagonists include small organic molecules, peptides, polypeptides and antibodies that bind to the polypeptide of the invention and thereby inhibit or extinguish its activity. In this fashion, binding of the polypeptide to normal cellular binding molecules may be inhibited, such that the normal biological activity of the polypeptide is prevented.

The polypeptide of the invention that is employed in such a screening technique may be free in solution, affixed to a solid support, borne on a cell surface or located intracellularly. In general, such screening procedures may involve using appropriate cells or cell membranes that express the polypeptide that are contacted with a test compound to observe binding, or stimulation or inhibition of a functional response. The functional response of the cells contacted with the test compound is then compared with control cells that were not contacted with the test compound. Such an assay may assess whether the test compound results in a signal generated by activation of the polypeptide, using an appropriate detection system. Inhibitors of activation are generally assayed in the presence of a known agonist and the effect on activation by the agonist in the presence of the test compound is observed.

A preferred method for identifying an agonist or antagonist compound of a polypeptide of the present invention comprises:

(a) contacting a cell expressing on the surface thereof the polypeptide according to the first aspect of the invention, the polypeptide being associated with a second component capable of providing a detectable signal in response to the binding of a compound to the polypeptide, with a compound to be screened under conditions to permit binding to the polypeptide; and (b) determining whether the compound binds to and activates or inhibits the polypeptide by measuring the level of a signal generated from the interaction of the compound with the polypeptide.

A further preferred method for identifying an agonist or antagonist of a polypeptide of the invention comprises:

(a) contacting a cell expressing on the surface thereof the polypeptide, the polypeptide being associated with a second component capable of providing a detectable signal in response to the binding of a compound to the polypeptide, with a compound to be screened under conditions to permit binding to the polypeptide; and (b) determining whether the compound binds to and activates or inhibits the polypeptide by comparing the level of a signal generated from the interaction of the compound with the polypeptide with the level of a signal in the absence of the compound.

In further preferred embodiments, the general methods that are described above may further comprise conducting the identification of agonist or antagonist in the presence of labelled or unlabelled ligand or receptor for the polypeptide.

In another embodiment of the method for identifying an agonist or antagonist of a polypeptide of the present invention comprises:

determining the inhibition of binding of a ligand or receptor to cells which have a polypeptide of the invention on the surface thereof, or to cell membranes containing such a polypeptide, in the presence of a candidate compound under conditions to permit binding to the polypeptide, and determining the amount of ligand or receptor bound to the polypeptide. A compound capable of causing reduction of binding of a ligand or receptor is considered to be an agonist or antagonist. Preferably the ligand is labelled.

More particularly, a method of screening for a polypeptide antagonist or agonist compound comprises the steps of:

(a) incubating a labelled ligand or receptor with a whole cell expressing a polypeptide according to the invention on the cell surface, or a cell membrane containing a polypeptide of the invention, (b) measuring the amount of labelled ligand or receptor bound to the whole cell or the cell membrane;

(c) adding a candidate compound to a mixture of labelled ligand or receptor and the whole cell or the cell membrane of step (a) and allowing the mixture to attain equilibrium;

(d) measuring the amount of labelled ligand or receptor bound to the whole cell or the cell membrane after step (c); and (e) comparing the difference in the labelled ligand or receptor bound in step (b) and (d), such that the compound which causes the reduction in binding in step (d) is considered to be an agonist or antagonist.

The INSP108 and INSP109 polypeptides may also be found to modulate immune system cell proliferation and differentiation in a dose-dependent manner in the above-described assays. Thus, the "functional equivalents" of the INSP108 and INSP109 polypeptides include polypeptides that exhibit any of the same growth and differentiation regulating activities in the above-described assays in a dose-dependent manner. Although the degree of dose-dependent activity need not be identical to that of the INSP108 or INSP109 polypeptides, preferably the "functional equivalents" will exhibit substantially similar dose-dependence in a given activity assay compared to the INSP108 and INSP109 polypeptides.

In certain of the embodiments described above, simple binding assays may be used, in which the adherence of a test compound to a surface bearing the polypeptide is detected by means of a label directly or indirectly associated with the test compound or in an assay involving competition with a labelled competitor. In another embodiment, competitive drug screening assays may be used, in which neutralising antibodies that are capable of binding the polypeptide specifically compete with a test compound for binding. In this manner, the antibodies can be used to detect the presence of any test compound that possesses specific binding affinity for the polypeptide.

Assays may also be designed to detect the effect of added test compounds on the production of mRNA encoding the polypeptide in cells. For example, an ELISA may be constructed that measures secreted or cell-associated levels of polypeptide using monoclonal or polyclonal antibodies by standard methods known in the art, and this can be used to search for compounds that may inhibit or enhance the production of the polypeptide from suitably manipulated cells or tissues. The formation of binding complexes between the polypeptide and the compound being tested may then be measured. A beta defensin antimicrobial assay is described by Nizet et al. (Nature 2001, 414:454-457). A theta defensin antimicrobial and antiviral assay is described by Cole et al. (Proc. Natl. Acad. Sci. 2002, 99(4):1813-1818).

Another technique for drug screening which may be used provides for high throughput screening of compounds having suitable binding affinity to the polypeptide of interest (see International patent application WO84/03564). In this method, large numbers of different small test compounds are synthesised on a solid substrate, which may then be reacted with the polypeptide of the invention and washed. One way of immobilising the polypeptide is to use non-neutralising antibodies. Bound polypeptide may then be detected using methods that are well known in the art. Purified polypeptide can also be coated directly onto plates for use in the aforementioned drug screening techniques.

The polypeptide of the invention may be used to identify membrane-bound or soluble receptors, through standard receptor binding techniques that are known in the art, such as ligand binding and crosslinking assays in which the polypeptide is labelled with a radioactive isotope, is chemically modified, or is fused to a peptide sequence that facilitates its detection or purification, and incubated with a source of the putative receptor (for example, a composition of cells, cell membranes, cell supernatants, tissue extracts, or bodily fluids). The efficacy of binding may be measured using biophysical techniques such as surface plasmon resonance and spectroscopy. Binding assays may be used for the purification and cloning of the receptor, but may also identify agonists and antagonists of the polypeptide, that compete with the binding of the polypeptide to its receptor. Standard methods for conducting screening assays are well understood in the art.

The invention also includes a screening kit useful in the methods for identifying agonists, antagonists, ligands, receptors, substrates, enzymes, that are described above.

The invention includes the agonists, antagonists, ligands, receptors, substrates and enzymes, and other compounds which modulate the activity or antigenicity of the polypeptide of the invention discovered by the methods that are described above.

The invention also provides pharmaceutical compositions comprising a polypeptide, nucleic acid, ligand or compound of the invention in combination with a suitable pharmaceutical carrier. These compositions may be suitable as therapeutic or diagnostic reagents, as vaccines, or as other immunogenic compositions, as outlined in detail below.

According to the terminology used herein, a composition containing a polypeptide, nucleic acid, ligand or compound [X] is "substantially free of" impurities [herein, Y] when at least 85% by weight of the total X+Y in the composition is X. Preferably, X comprises at least about 90% by weight of the total of X+Y in the composition, more preferably at least about 95%, 98% or even 99% by weight.

The pharmaceutical compositions should preferably comprise a therapeutically effective amount of the polypeptide, nucleic acid molecule, ligand, or compound of the invention. The term "therapeutically effective amount" as used herein refers to an amount of a therapeutic agent needed to treat, ameliorate, or prevent a targeted disease or condition, or to exhibit a detectable therapeutic or preventative effect. For any compound, the therapeutically effective dose can be estimated initially either in cell culture assays, for example, of neoplastic cells, or in animal models, usually mice, rabbits, dogs, or pigs. The animal model may also be used to determine the appropriate concentration range and route of administration. Such information can then be used to determine useful doses and routes for administration in humans.

The precise effective amount for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician. Generally, an effective dose will be from 0.01 mg/kg to 50 mg/kg, preferably 0.05 mg/kg to 10 mg/kg. Compositions may be administered individually to a patient or may be administered in combination with other agents, drugs or hormones.

A pharmaceutical composition may also contain a pharmaceutically acceptable carrier, for administration of a therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity. Suitable carriers may be large, slowly metabolised macromolecules such as proteins, polysaccharides, polylactic acids, polyglycolic acids, polymeric amino acids, amino acid copolymers and inactive virus particles.

Pharmaceutically acceptable salts can be used therein, for example, mineral acid salts such as hydrochlorides, hydrobromides, phosphates, sulphates, and the like; and the salts of organic acids such as acetates, propionates, malonates, benzoates, and the like. A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The pharmaceutical compositions utilised in this invention may be administered by any number of routes including, but not limited to, oral, intravenous, intramuscular, intra-arterial, intramedullary, intrathecal, intraventricular, transdermal or transcutaneous applications (for example, see WO98/20734), subcutaneous, intraperitoneal, intranasal, enteral, topical, sublingual, intravaginal or rectal means. Gene guns or hyposprays may also be used to administer the pharmaceutical compositions of the invention. Typically, the therapeutic compositions may be prepared as injectables, either as liquid solutions or suspensions; solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

If the activity of the polypeptide of the invention is in excess in a particular disease state, several approaches are available. One approach comprises administering to a subject an inhibitor compound (antagonist) as described above, along with a pharmaceutically acceptable carrier in an amount effective to inhibit the function of the polypeptide, such as by blocking the binding of ligands, substrates, enzymes, receptors, or by inhibiting a second signal, and thereby alleviating the abnormal condition. Preferably, such antagonists are antibodies. Most preferably, such antibodies are chimeric and/or humanised to minimise their immunogenicity, as described previously.

In another approach, soluble forms of the polypeptide that retain binding affinity for the ligand, substrate, enzyme, receptor, in question, may be administered. Typically, the polypeptide may be administered in the form of fragments that retain the relevant portions.

In an alternative approach, expression of the gene encoding the polypeptide can be inhibited using expression blocking techniques, such as the use of antisense nucleic acid molecules (as described above), either internally generated or separately administered. Modifications of gene expression can be obtained by designing complementary sequences or antisense molecules (DNA, RNA, or PNA) to the control, 5' or regulatory regions (signal sequence, promoters, enhancers and introns) of the gene encoding the polypeptide. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al.

(1994) In: Huber, B. E. and B. I. Carr, Molecular and Immunologic Approaches, Futura Publishing Co., Mt. Kisco, N.Y.). The complementary sequence or antisense molecule may also be designed to block translation of mRNA by preventing the transcript from binding to ribosomes. Such oligonucleotides may be administered or may be generated in situ from expression in vivo.

In addition, expression of the polypeptide of the invention may be prevented by using ribozymes specific to its encoding mRNA sequence. Ribozymes are catalytically active RNAs that can be natural or synthetic (see for example Usman, N, et al., Curr. Opin. Struct. Biol (1996) 6(4), 527-33). Synthetic ribozymes can be designed to specifically cleave mRNAs at selected positions thereby preventing translation of the mRNAs into functional polypeptide. Ribozymes may be synthesised with a natural ribose phosphate backbone and natural bases, as normally found in RNA molecules. Alternatively the ribozymes may be synthesised with non-natural backbones, for example, 2'-O-methyl RNA, to provide protection from ribonuclease degradation and may contain modified bases.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of non-traditional bases such as inosine, queosine and butosine, as well as acetyl-, methyl-, thio- and similarly modified forms of adenine, cytidine, guanine, thymine and uridine which are not as easily recognised by endogenous endonucleases.

For treating abnormal conditions related to an under-expression of the polypeptide of the invention and its activity, several approaches are also available. One approach comprises administering to a subject a therapeutically effective amount of a compound that activates the polypeptide, i.e., an agonist as described above, to alleviate the abnormal condition. Alternatively, a therapeutic amount of the polypeptide in combination with a suitable pharmaceutical carrier may be administered to restore the relevant physiological balance of polypeptide.

Gene therapy may be employed to effect the endogenous production of the polypeptide by the relevant cells in the subject. Gene therapy is used to treat permanently the inappropriate production of the polypeptide by replacing a defective gene with a corrected therapeutic gene.

Gene therapy of the present invention can occur in vivo or ex vivo. Ex vivo gene therapy requires the isolation and purification of patient cells, the introduction of a therapeutic gene and introduction of the genetically altered cells back into the patient. In contrast, in vivo gene therapy does not require isolation and purification of a patient's cells.

The therapeutic gene is typically "packaged" for administration to a patient. Gene delivery vehicles may be non-viral, such as liposomes, or replication-deficient viruses, such as adenovirus as described by Berkner, K. L., in Curr. Top. Microbiol. Immunol., 158, 39-66 (1992) or adeno-associated virus (AAV) vectors as described by Muzyczka, N., in Curr. Top. Microbiol. Immunol., 158, 97-129 (1992) and U.S. Pat. No. 5,252,479. For example, a nucleic acid molecule encoding a polypeptide of the invention may be engineered for expression in a replication-defective retroviral vector. This expression construct may then be isolated and introduced into a packaging cell transduced with a retroviral plasmid vector containing RNA encoding the polypeptide, such that the packaging cell now produces infectious viral particles containing the gene of interest. These producer cells may be administered to a subject for engineering cells in vivo and expression of the polypeptide in vivo (see Chapter 20, Gene Therapy and other Molecular Genetic-based Therapeutic Approaches, (and references cited therein) in Human Molecular Genetics (1996), T Strachan and A P Read, BIOS Scientific Publishers Ltd).

Another approach is the administration of "naked DNA" in which the therapeutic gene is directly injected into the bloodstream or muscle tissue.

In situations in which the polypeptides or nucleic acid molecules of the invention are disease-causing agents, the invention provides that they can be used in vaccines to raise antibodies against the disease causing agent.

Vaccines according to the invention may either be prophylactic (i.e. to prevent infection) or therapeutic (i.e. to treat disease after infection). Such vaccines comprise immunising antigen(s), immunogen(s), polypeptide(s), protein(s) or nucleic acid, usually in combination with pharmaceutically-acceptable carriers as described above, which include any carrier that does not itself induce the production of antibodies harmful to the individual receiving the composition. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, and other pathogens.

Since polypeptides may be broken down in the stomach, vaccines comprising polypeptides are preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation isotonic with the blood of the recipient, and aqueous and non-aqueous sterile suspensions which may include suspending agents or thickening agents.

The vaccine formulations of the invention may be presented in unit-dose or multi-dose containers. For example, sealed ampoules and vials and may be stored in a freeze-dried condition requiring only the addition of the sterile liquid carrier immediately prior to use. The dosage will depend on the specific activity of the vaccine and can be readily determined by routine experimentation.

Genetic delivery of antibodies that bind to polypeptides according to the invention may also be effected, for example, as described in International patent application WO98/55607.

The technology referred to as jet injection (see, for example, www.powderject.com) may also be useful in the formulation of vaccine compositions.

A number of suitable methods for vaccination and vaccine delivery systems are described in International patent application WO00/29428.

This invention also relates to the use of nucleic acid molecules according to the present invention as diagnostic reagents. Detection of a mutated form of the gene characterised by the nucleic acid molecules of the invention which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques.

Nucleic acid molecules for diagnosis may be obtained from a subject's cells, such as from blood, urine, saliva, tissue biopsy or autopsy material. The genomic DNA may be used directly for detection or may be amplified enzymatically by using PCR, ligase chain reaction (LCR), strand displacement amplification (SDA), or other amplification techniques (see Saiki et al., Nature, 324, 163-166 (1986); Bej, et al., Crit. Rev. Biochem. Molec. Biol., 26, 301-334 (1991); Birkenmeyer et al., J. Virol. Meth., 35, 117-126 (1991); Van Brunt, J., Bio/Technology, 8, 291-294 (1990)) prior to analysis.

In one embodiment, this aspect of the invention provides a method of diagnosing a disease in a patient, comprising assessing the level of expression of a natural gene encoding a polypeptide according to the invention and comparing said level of expression to a control level, wherein a level that is different to said control level is indicative of disease. The method may comprise the steps of:
a) contacting a sample of tissue from the patient with a nucleic acid probe under stringent conditions that allow the formation of a hybrid complex between a nucleic acid molecule of the invention and the probe;
b) contacting a control sample with said probe under the same conditions used in step a);
c) and detecting the presence of hybrid complexes in said samples;

wherein detection of levels of the hybrid complex in the patient sample that differ from levels of the hybrid complex in the control sample is indicative of disease.

A further aspect of the invention comprises a diagnostic method comprising the steps of:
a) obtaining a tissue sample from a patient being tested for disease;
b) isolating a nucleic acid molecule according to the invention from said tissue sample; and
c) diagnosing the patient for disease by detecting the presence of a mutation in the nucleic acid molecule which is associated with disease.

To aid the detection of nucleic acid molecules in the above-described methods, an amplification step, for example using PCR, may be included.

Deletions and insertions can be detected by a change in the size of the amplified product in comparison to the normal genotype. Point mutations can be identified by hybridizing amplified DNA to labelled RNA of the invention or alternatively, labelled antisense DNA sequences of the invention. Perfectly-matched sequences can be distinguished from mismatched duplexes by RNase digestion or by assessing differences in melting temperatures. The presence or absence of the mutation in the patient may be detected by contacting DNA with a nucleic acid probe that hybridises to the DNA under stringent conditions to form a hybrid double-stranded molecule, the hybrid double-stranded molecule having an unhybridised portion of the nucleic acid probe strand at any portion corresponding to a mutation associated with disease; and detecting the presence or absence of an unhybridised portion of the probe strand as an indication of the presence or absence of a disease-associated mutation in the corresponding portion of the DNA strand.

Such diagnostics are particularly useful for prenatal and even neonatal testing.

Point mutations and other sequence differences between the reference gene and "mutant" genes can be identified by other well-known techniques, such as direct DNA sequencing or single-strand conformational polymorphism, (see Orita et al., Genomics, 5, 874-879 (1989)). For example, a sequencing primer may be used with double-stranded PCR product or a single-stranded template molecule generated by a modified PCR. The sequence determination is performed by conventional procedures with radiolabelled nucleotides or by automatic sequencing procedures with fluorescent-tags. Cloned DNA segments may also be used as probes to detect specific DNA segments. The sensitivity of this method is greatly enhanced when combined with PCR. Further, point mutations and other sequence variations, such as polymorphisms, can be detected as described above, for example, through the use of allele-specific oligonucleotides for PCR amplification of sequences that differ by single nucleotides.

DNA sequence differences may also be detected by alterations in the electrophoretic mobility of DNA fragments in gels, with or without denaturing agents, or by direct DNA sequencing (for example, Myers et al., Science (1985) 230: 1242). Sequence changes at specific locations may also be revealed by nuclease protection assays, such as RNase and S1 protection or the chemical cleavage method (see Cotton et al., Proc. Natl. Acad. Sci. USA (1985) 85: 4397-4401).

In addition to conventional gel electrophoresis and DNA sequencing, mutations such as microdeletions, aneuploidies, translocations, inversions, can also be detected by in situ analysis (see, for example, Keller et al., DNA Probes, 2nd Ed., Stockton Press, New York, N.Y., USA (1993)), that is, DNA or RNA sequences in cells can be analysed for mutations without need for their isolation and/or immobilisation onto a membrane. Fluorescence in situ hybridization (FISH) is presently the most commonly applied method and numerous reviews of FISH have appeared (see, for example, Trachuck et al., Science, 250, 559-562 (1990), and Trask et al., Trends, Genet., 7, 149-154 (1991)).

In another embodiment of the invention, an array of oligonucleotide probes comprising a nucleic acid molecule according to the invention can be constructed to conduct efficient screening of genetic variants, mutations and polymorphisms. Array technology methods are well known and have general applicability and can be used to address a variety of questions in molecular genetics including gene expression, genetic linkage, and genetic variability (see for example: M. Chee et al., Science (1996), Vol 274, pp 610-613).

In one embodiment, the array is prepared and used according to the methods described in PCT application WO95/11995 (Chee et al); Lockhart, D. J. et al. (1996) Nat. Biotech. 14: 1675-1680); and Schena, M. et al. (1996) Proc. Natl. Acad. Sci. 93: 10614-10619). Oligonucleotide pairs may range from two to over one million. The oligomers are synthesized at designated areas on a substrate using a light-directed chemical process. The substrate may be paper, nylon or other type of membrane, filter, chip, glass slide or any other suitable solid support. In another aspect, an oligonucleotide may be synthesized on the surface of the substrate by using a chemical coupling procedure and an ink jet application apparatus, as described in PCT application WO95/25116 (Baldeschweiler et al.). In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and over one million which lends itself to the efficient use of commercially-available instrumentation.

In addition to the methods discussed above, diseases may be diagnosed by methods comprising determining, from a sample derived from a subject, an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods.

Assay techniques that can be used to determine levels of a polypeptide of the present invention in a sample derived from a host are well-known to those of skill in the art and are discussed in some detail above (including radioimmunoassays, competitive-binding assays, Western Blot analysis and ELISA assays). This aspect of the invention provides a diagnostic method which comprises the steps of: (a) contacting a ligand as described above with a biological sample under conditions suitable for the formation of a ligand-polypeptide complex; and (b) detecting said complex.

Protocols such as ELISA (as previously described), RIA and FACS for measuring polypeptide levels may additionally provide a basis for diagnosing altered or abnormal levels of polypeptide expression. Normal or standard values for polypeptide expression are established by combining body fluids or cell extracts taken from normal mammalian subjects, preferably humans, with antibody to the polypeptide under conditions suitable for complex formation The amount of standard complex formation may be quantified by various methods, such as by photometric means.

Antibodies which specifically bind to a polypeptide of the invention may be used for the diagnosis of conditions or diseases characterised by expression of the polypeptide, or in assays to monitor patients being treated with the polypeptides, nucleic acid molecules, ligands and other compounds of the invention. Antibodies useful for diagnostic purposes may be prepared in the same manner as those described above for therapeutics. Diagnostic assays for the polypeptide include methods that utilise the antibody and a label to detect the polypeptide in human body fluids or extracts of cells or tissues. The antibodies may be used with or without modification, and may be labelled by joining them, either covalently or non-covalently, with a reporter molecule. A wide variety of reporter molecules known in the art may be used, several of which are described above.

Quantities of polypeptide expressed in subject, control and disease samples from biopsied tissues are compared with the standard values. Deviation between standard and subject values establishes the parameters for diagnosing disease. Diagnostic assays may be used to distinguish between absence, presence, and excess expression of polypeptide and to monitor regulation of polypeptide levels during therapeutic intervention. Such assays may also be used to evaluate the efficacy of a particular therapeutic treatment regimen in animal studies, in clinical trials or in monitoring the treatment of an individual patient.

A diagnostic kit of the present invention may comprise:

(a) a nucleic acid molecule of the present invention;

(b) a polypeptide of the present invention; or (c) a ligand of the present invention.

In one aspect of the invention, a diagnostic kit may comprise a first container containing a nucleic acid probe that hybridises under stringent conditions with a nucleic acid molecule according to the invention; a second container containing primers useful for amplifying the nucleic acid molecule; and instructions for using the probe and primers for facilitating the diagnosis of disease. The kit may further comprise a third container holding an agent for digesting unhybridised RNA.

In an alternative aspect of the invention, a diagnostic kit may comprise an array of nucleic acid molecules, at least one of which may be a nucleic acid molecule according to the invention.

To detect polypeptide according to the invention, a diagnostic kit may comprise one or more antibodies that bind to a polypeptide according to the invention; and a reagent useful for the detection of a binding reaction between the antibody and the polypeptide.

Such kits will be of use in diagnosing a disease or susceptibility to disease in which members of the defensin family are implicated. Such diseases may include cell proliferative disorders, including neoplasm, melanoma, lung, colorectal, breast, pancreas, head and neck and other solid tumours; myeloproliferative disorders, such as leukemia, non-Hodgkin lymphoma, leukopenia, thrombocytopenia, angiogenesis disorder, Kaposi' sarcoma; autoimmune/inflammatory disorders, including allergy, inflammatory bowel disease, arthritis, psoriasis and respiratory tract inflammation, asthma, and organ transplant rejection; cardiovascular disorders, including hypertension, oedema, angina, atherosclerosis, thrombosis, sepsis, shock, reperfusion injury, and ischemia; neurological disorders including central nervous system disease, Alzheimer's disease, brain injury, amyotrophic lateral sclerosis, and pain; developmental disorders; metabolic disorders including diabetes mellitus, osteoporosis, and obesity, AIDS and renal disease; infections including viral infection, bacterial infection, fungal infection and parasitic infection and other pathological conditions. Preferably, the diseases are those in which members of the defensin family are implicated, such as sublethal endotoxaemia, septic shock, microbial infection of the amniotic cavity, Jarish-Herxheimer reaction of relapsing fever, infectious diseases of the central nervous system, acute pancreatitis, ulcerative colitis, empyaema, haemolytic uraemic syndrome, meningococcal disease, gastric infection, pertussis, peritonitis, psoriasis, rheumatoid arthritis, sepsis, asthma, HIV, AIDS and glomerulonephritis.

Various aspects and embodiments of the present invention will now be described in more detail by way of example, with particular reference to the INSP108 and INSP109 polypeptides.

It will be appreciated that modification of detail may be made without departing from the scope of the invention.

BRIEF DESCRIPTION OF THE FIGURES

FIG. 1: BLAST result against NCBI non-redundant database using SEQ ID NO: 6 (the INSP108 polypeptide)

FIG. 2: Alignment between INSP108 polypeptide sequence (SEQ ID NO:6) and defensin beta 123 (*Homo sapiens*)

FIG. 3: Sig P cleavage site prediction for INSP108

FIG. 4: BLAST result against NCBI non-redundant database using SEQ ID NO: 14 (the INSP109 polypeptide)

FIG. 5: Alignment between INSP109 polypeptide sequence (SEQ ID NO:14) and defensin beta 4 (*Mus musculus*)

FIG. 6: Sig P cleavage site prediction for INSP109

FIG. 7: Predicted nucleotide sequence of INSP108 with translation (SEQ ID NOs:37 and 38).

FIG. 8: Nucleotide sequence with translation of INSP108 PCR product cloned using primers INSP108-CP1 and INSP108-CP2 (SEQ ID NOs:39 and 38).

FIG. 9: Map of pCR4-TOPO-INSP108

FIG. 10: Map of pDONR 221

FIG. 11: Map of expression vector pEAK12d

FIG. 12: Map of expression vector pDEST12.2
FIG. 13: Map of pDONR221-INSP108-6HIS
FIG. 14: Map of pEAK12d-INSP108-6HIS
FIG. 15: Map of pDEST12.2-INSP108-6HIS
FIG. 16: Predicted nucleotide sequence of INSP109 with translation (SEQ ID NOs:40 and 14).
FIG. 17: INSP109 coding exon organization in genomic DNA and position of PCR primers (SEQ ID NOs:13 and 41).
FIG. 18: Nucleotide sequence and translation of cloned INSP109 ORF (SEQ ID NOs:42 and 14).
FIG. 19: Map of pCR4-TOPO-INSP109
FIG. 20: Map of pDONR-INSP109-6HIS
FIG. 21: Map of pEAK12d-INSP109-6HIS
FIG. 22: Map of pDEST12.2-INSP109-6HIS

EXAMPLES

Example 1

INSP108

The INSP108 polypeptide sequence, shown in SEQ ID NO:6, was used as a BLAST query against the NCBI non-redundant sequence database. The top hit is to a *Homo sapiens* gene annotated as a defensin (FIG. 1). INSP108 aligns to this sequence with a significant E-value ($4e^{-6}$) (FIG. 2), thus indicating a high degree of confidence in the prediction.

Example 2

INSP108 Signal Sequence

FIG. 3 show that INSP108 is predicted to possess a signal peptide at the start of the protein. As the SigP data in FIG. 3 clearly shows, the signal peptide cleavage site is thought to be between residues 24 and 25 of the INSP108 polypeptide sequence (Nielsen, H. et al. 1997, Protein Engineering, 10, 1-6; Nielsen, H., and Krogh, A.: Prediction of signal peptides and signal anchors by a hidden Markov model. In Proceedings of the Sixth International Conference on Intelligent Systems for Molecular Biology (ISMB 6), AAAI Press, Menlo Park, Calif., pp. 122-130 (1998)).

Example 3

INSP109

The INSP109 polypeptide sequence, shown in SEQ ID NO:14, was used as a BLAST query against the NCBI non-redundant sequence database. The top hit is to a *Mus musculus* gene prediction that is unannotated, and the second hit was *Mus musculus* defensin beta 4 (NP_062702.1) (FIG. 4). FIG. 5 shows the INSP109 polypeptide aligned with the *Mus musculus* defensin beta 4.

Example 4

INSP109 Signal Sequence

FIG. 6 shows that INSP109 is predicted to possess a signal peptide at the start of the protein. As the SigP data in FIG. 6 clearly shows, the signal peptide cleavage site is thought to be between residues 21 and 22 of the INSP109 polypeptide sequence (Nielsen, 10H. et al. 1997, Protein Engineering, 10, 1-6; Nielsen, H., and Krogh, A.: Prediction of signal peptides and signal anchors by a hidden Markov model. In Proceedings of the Sixth International Conference on Intelligent Systems for Molecular Biology (ISMB 6), AAAI Press, Menlo Park, Calif., pp. 122-130 (1998)).

Example 5

Cloning of INSP108

1.1 Preparation of Human cDNA Templates

First strand cDNA was prepared from a variety of normal human tissue total RNA samples (Clontech, Stratagene, Ambion, Biochain Institute and in-house preparations) using Superscript II RNase H—Reverse Transcriptase (Invitrogen) according to the manufacturer's protocol. Oligo $(dT)_{15}$ primer (1 µl at 500 µg/ml) (Promega), 2 µg human total RNA, 1 µl 10 mM dNTP mix (10 mM each of dATP, dGTP, dCTP and dTTP at neutral pH) and sterile distilled water to a final volume of 12 µl were combined in a 1.5 ml Eppendorf tube, heated to 65° C. for 5 min and then chilled on ice. The contents were collected by brief centrifugation and 4 µl of 5× First-Strand Buffer, 2 µl 0.1 M DTT, and 1 µl RnaseOUT Recombinant Ribonuclease Inhibitor (40 units/µl, Invitrogen) were added. The contents of the tube were mixed gently and incubated at 42° C. for 2 min; then 1 µl (200 units) of SuperScript II enzyme was added and mixed gently by pipetting. The mixture was incubated at 42° C. for 50 min and then inactivated by heating at 70° C. for 15 min. To remove RNA complementary to the cDNA, 1 µl (2 units) of *E. coli* RNase H (Invitrogen) was added and the reaction mixture incubated at 37° C. for 20 min. The final 21 µl reaction mix was diluted by adding 179 µl sterile water to give a total volume of 200 µl. Human cDNA samples used as templates for the amplification of INSP108 were derived from brain, kidney, liver, lung, placenta, skeletal muscle, small intestine, spleen, thyroid, colon, testis, skin, pancreas, pituitary gland, salivary gland, adrenal gland, eye, and a mixture of cancer cell line samples (Universal Reference RNA sample, Stratagene).

1.2 Gene Specific Cloning Primers for PCR

A pair of PCR primers having a length of between 18 and 25 bases were designed for amplifying the complete coding sequence of the virtual cDNA using Primer Designer Software (Scientific & Educational Software, PO Box 72045, Durham, N.C. 27722-2045, USA). PCR primers were optimized to have a Tm close to 55±10° C. and a GC content of 40-60%. Primers were selected which had high selectivity for the target sequence (INSP108) with little or no none specific priming.

1.3 PCR Amplification of INSP108 from a Variety of Human cDNA Templates

Gene-specific cloning primers (INSP108-CP1 and INSP108-CP2, FIG. 7, FIG. 8 and Table 1) were designed to amplify a cDNA fragment of 245 bp covering the entire 231 bp coding predicted sequence of the INSP108. Analysis of the scientific literature suggested that beta-defensin proteins should be expressed on mucosal surfaces and by secretory organs. The gene-specific cloning primers INSP108-CP1 and INSP108-CP2 were therefore used with human cDNA samples listed in Section 1.1 as the PCR templates. The PCR reactions were performed in a final volume of 50 µl containing 1× Platinum® Taq High Fidelity PCR buffer, 2 mM $MgSO_4$, 200 µM dNTPs, 0.2 µM of each cloning primer, 2.5 units of Platinum® Taq DNA High Fidelity (Invitrogen) DNA polymerase and 100 ng of human cDNA template using an MJ Research DNA Engine, programmed as follows: 94° C., 2 min; 40 cycles of 94° C., 30 sec, 55° C., 30 sec, 68° C., 30 sec, followed by 1 cycle at 68° C. for 7 min and a holding cycle at 4° C.

A 5 µl aliquot of each amplification product was visualized on a 0.8% agarose gel in 1×TAE buffer (Invitrogen) and a single PCR product was seen migrating at approximately the predicted molecular mass in the sample corresponding to the testis cDNA. The remaining PCR product from the testis amplification was electrophoresed on a second 0.8% agarose gel and purified using the Qiagen MinElute DNA Purification System (Qiagen). The PCR product was eluted in 10 µl of EB buffer (10 mM Tris.Cl, pH 8.5) and subcloned directly.

1.4 Subcloning of PCR Products

The PCR product was subcloned into the topoisomerase I modified cloning vector (pCR4-TOPO) using the TA cloning kit purchased from the Invitrogen Corporation using the conditions specified by the manufacturer. Briefly, 4 µl of gel purified PCR product from the human testis cDNA amplification was incubated for 15 min at room temperature with 1 µl of TOPO vector and 1 µl salt solution. The reaction mixture was then transformed into *E. coli* strain TOP10 (Invitrogen) as follows: a 50 µl aliquot of One Shot TOP10 cells was thawed on ice and 2 µl of TOPO reaction was added. The mixture was incubated for 15 min on ice and then heat shocked by incubation at 42° C. for exactly 30 s. Samples were returned to ice and 250 µl of warm (room temperature) SOC media was added. Samples were incubated with shaking (220 rpm) for 1 h at 37° C. The transformation mixture was then plated on L-broth (LB) plates containing ampicillin (100 µg/ml) and incubated overnight at 37° C.

1.5 Colony PCR

Colonies were inoculated into 50 µl sterile water using a sterile toothpick. A 10 µl aliquot of the inoculum was then subjected to PCR in a total reaction volume of 20 µl containing 1× AmpliTaq™ buffer, 200 µM dNTPs, 20 pmoles T7 primer, 20 pmoles of T3 primer, 1 unit of AmpliTaq™ (Perkin Elmer) using an MJ Research DNA Engine. The cycling conditions were as follows: 94° C., 2 min; 30 cycles of 94° C., 30 sec, 48° C., 30 sec and 72° C. for 1 min. Samples were maintained at 4° C. (holding cycle) before further analysis.

PCR reaction products were analyzed on 1% agarose gels in 1×TAE buffer. Colonies which gave the expected PCR product size (245 bp cDNA+105 bp due to the multiple cloning site or MCS) were grown up overnight at 37° C. in 5 ml L-Broth (LB) containing ampicillin (100 µg/ml), with shaking at 220 rpm.

1.6 Plasmid DNA Preparation and Sequencing

Miniprep plasmid DNA was prepared from the 5 ml culture using a Qiaprep Turbo 9600 robotic system (Qiagen) or Wizard Plus SV Minipreps kit (Promega cat. no. 1460) according to the manufacturer's instructions. Plasmid DNA was eluted in 100 µl of sterile water. The DNA concentration was measured using an Eppendorf BO photometer. Plasmid DNA (200-500 ng) was subjected to DNA sequencing with the T7 primer and T3 primer using the BigDyeTerminator system (Applied Biosystems cat. no. 4390246) according to the manufacturer's instructions. The primer sequences are shown in Table 1. Sequencing reactions were purified using Dye-Ex columns (Qiagen) or Montage SEQ 96 cleanup plates (Millipore cat. no. LSKS09624) then analyzed on an Applied Biosystems 3700 sequencer.

Sequence analysis identified a clone containing a 100% match to the predicted INSP108 sequence. The sequence of the cloned cDNA fragment is shown in FIG. 8. The plasmid map of the cloned PCR product (pCR4-TOPO-INSP108) (plasmid ID. 13982) is shown in FIG. 9.

2. Construction of a Plasmid for the Expression of INSP108 in HEK293/EBNA Cells.

A pCR4-TOPO clone containing the full coding sequence (ORF) of INSP108 identified by DNA sequencing (pCR4-TOPO-INSP108, plasmid ID. 13982) (FIG. 9) was then used to subclone the insert into the mammalian cell expression vectors pEAK12d (FIG. 11) and pDEST12.2 (FIG. 12) using the Gateway™ cloning methodology (Invitrogen).

2.1 Generation of Gateway Compatible INSP108 ORF Fused to an in Frame 6HIS Tag Sequence.

The first stage of the Gateway cloning process involves a two step PCR reaction which generates the ORF of INSP108 flanked at the 5' end by an attB1 recombination site and Kozak sequence, and flanked at the 3' end by a sequence encoding an in frame 6 histidine (6HIS) tag, a stop codon and the attB2 recombination site (Gateway compatible cDNA). The first PCR reaction (in a final volume of 50 µl) contains: 1.5 µl of pCR4-TOPO-INSP108 (plasmid ID 13982), 1.5 µl dNTPs (10 mM), 5 µl of 10×Pfx polymerase buffer, 1 µl MgSO4 (50 mM), 0.5 µl each of gene specific primer (100 µM) (INSP108-EX1 and INSP0108-EX2), 2.5 µl 10× Enhancer™ solution (Invitrogen) and 1 µl Platinum Pfx DNA polymerase (Invitrogen). The PCR reaction was performed using an initial denaturing step of 95° C. for 2 min, followed by 15 cycles of 94° C. for 15 s; 55° C. for 30 s and 68° C. for 2 min 30 sec; and a holding cycle of 4° C. The amplification products were purified directly from the PCR mixture using the Wizard PCR Preps DNA Purification System (Promega) and recovered in 50 µl sterile water according to the manufacturer's instructions.

The second PCR reaction (in a final volume of 50 µl) contained 10 µl purified PCR 1 product, 1.5 µl dNTPs (10 mM), 5 µl of 10×Pfx polymerase buffer, 1 µl MgSO4 (50 mM), 0.5 µl of each Gateway conversion primer (100 µM) (GCP forward and GCP reverse) and 0.5 µl of Platinum Pfx DNA polymerase. The conditions for the 2nd PCR reaction were: 95° C. for 1 min; 4 cycles of 94° C., 15 sec; 50° C., 30 sec and 68° C. for 2 min 30 sec; 19 cycles of 94° C., 15 sec; 55° C., 30 sec and 68° C., 2 min 30 sec; followed by a holding cycle of 4° C. PCR products were gel purified using the Wizard PCR prep DNA purification system (Promega) according to the manufacturer's instructions.

2.2 Subcloning of Gateway Compatible INSP108 ORF into Gateway Entry Vector pDONR221 and Expression Vectors pEAK12d and pDEST12.2

The second stage of the Gateway cloning process involves subcloning of the Gateway modified PCR product into the Gateway entry vector pDONR221 (Invitrogen, FIG. 10) as follows: 5 µl of purified product from PCR2 were incubated with 1 µl pDONR221 vector (0.15 µg/µl), 2 µl BP buffer and 1.5 µl of BP clonase enzyme mix (Invitrogen) in a final volume of 10 µl at RT for 1 h. The reaction was stopped by addition of proteinase K (2 µg) and incubated at 37° C. for a further 10 min. An aliquot of this reaction (2 µl) was used to transform *E. coli* DH10B cells by electroporation as follows: a 30 µl aliquot of DH10B electrocompetent cells (Invitrogen) was thawed on ice and 2 µl of the BP reaction mix was added. The mixture was transferred to a chilled 0.1 cm electroporation cuvette and the cells electroporated using a BioRad Gene-Pulser™ according to the manufacturer's recommended protocol. SOC media (0.5 ml) which had been pre-warmed to room temperature was added immediately after electroporation. The mixture was transferred to a 15 ml snap-cap tube and incubated, with shaking (220 rpm) for 1 h at 37° C. Aliquots of the transformation mixture (10 µl and 50 µl) were then plated on L-broth (LB) plates containing kanamycin (40 µg/ml) and incubated overnight at 37° C.

Plasmid mini-prep DNA was prepared from 5 ml cultures from 6 of the resultant colonies using a Qiaprep Turbo 9600 robotic system (Qiagen). Plasmid DNA (200-500 ng) was subjected to DNA sequencing with 21M13 and M13Rev primers using the BigDyeTerminator system (Applied Biosystems cat. no. 4390246) according to the manufacturer's instructions. The primer sequences are shown in Table 1. Sequencing reactions were purified using Dye-Ex columns (Qiagen) or Montage SEQ 96 cleanup plates (Millipore cat. no. LSKS09624) then analyzed on an Applied Biosystems 3700 sequencer.

Plasmid eluate (2 μl) from one of the clones which contained the correct sequence (pDONR221-INSP108-6HIS, plasmid ID 14224, FIG. 13) was then used in a recombination reaction containing 1.5 μl of either pEAK12d vector or pDEST12.2 vector (FIGS. 11 & 12) (0.1 μg/μl), 2 μl LR buffer and 1.5 μl of LR clonase (Invitrogen) in a final volume of 10 μl. The mixture was incubated at RT for 1 h, stopped by addition of proteinase K (2 μg) and incubated at 37° C. for a further 10 min. An aliquot of this reaction (1 μl) was used to transform *E. coli* DH10B cells by electroporation as follows: a 30 μl aliquot of DH10B electrocompetent cells (Invitrogen) was thawed on ice and 1 μl of the LR reaction mix was added. The mixture was transferred to a chilled 0.1 cm electroporation cuvette and the cells electroporated using a BioRad Gene-Pulser™ according to the manufacturer's recommended protocol. SOC media (0.5 ml) which had been pre-warmed to room temperature was added immediately after electroporation. The mixture was transferred to a 15 ml snap-cap tube and incubated, with shaking (220 rpm) for 1 h at 37° C. Aliquots of the transformation mixture (10 μl and 50 μl) were then plated on L-broth (LB) plates containing ampicillin (100 μg/ml) and incubated overnight at 37° C.

Plasmid mini-prep DNA was prepared from 5 ml cultures from 6 of the resultant colonies subcloned in each vector using a Qiaprep Turbo 9600 robotic system (Qiagen). Plasmid DNA (200-500 ng) in the pEAK12d vector was subjected to DNA sequencing with pEAK12F and pEAK12R primers as described above. Plasmid DNA (200-500 ng) in the pDEST12.2 vector was subjected to DNA sequencing with 21M13 and M13Rev primers as described above. Primers sequences are shown in Table 1.

CsCl gradient purified maxi-prep DNA was prepared from a 500 ml culture of one of each of the sequence verified clones (pEAK12d-INSP108-6HIS, plasmid ID number 14228, FIG. 14, and pDEST12.2-INSP108-6HIS, plasmid ID 14229, FIG. 15) using the method described by Sambrook J. et al., 1989 (in Molecular Cloning, a Laboratory Manual, 2$^{nd}$ edition, Cold Spring Harbor Laboratory Press). Plasmid DNA was resuspended at a concentration of 1 μg/μl in sterile water and stored at −20° C.

TABLE 1

INSP108 cloning and sequencing primers

| Primer | Sequence (5'-3') |
|---|---|
| INSP108-CP1 | ATT GGT ATG GCC ACA AGG AG |
| INSP108-CP2 | CAC AAC TAT TTC CCA GTC AGT A |
| INSP108-EX1 | AA GCA GGC TTC <u>GCC ACC</u> ATG GCC ACA AGG AGC GTC CT |
| INSP108-EX2 | *GTG ATG GTG ATG GTG* TTC TGC CTC CTG CGT CTT GT |
| GCP Forward | G GGG ACA AGT TTG TAC AAA AAA GCA GGC TTC <u>GCC ACC</u> |
| GCP Reverse | GGG GAC CAC TTT GTA CAA GAA AGC TGG GTT TCA *ATG GTG ATG GTG ATG GTG* |

TABLE 1-continued

INSP108 cloning and sequencing primers

| Primer | Sequence (5'-3') |
|---|---|
| pEAK12F | GCC AGC TTG GCA CTT GAT GT |
| pEAK12R | GAT GGA GGT GGA CGT GTC AG |
| 21M13 | TGT AAA ACG ACG GCC AGT |
| M13REV | CAG GAA ACA GCT ATG ACC |
| T7 | TAA TAC GAC TCA CTA TAG G |
| T3 | ATT AAC CCT CAC TAA AGG |

<u>Underlined</u> sequence = Kozak sequence
Bold = Stop codon
*Italic* sequence = His tag Example 6

Cloning of INSP109 by Exon Assembly 1.1 PCR Amplification of Exons Encoding INSP109 from Genomic DNA.

PCR primers were designed to amplify exons 1 and 2 of INSP109 (table 2). The reverse primer for exon 1 (INSP109-exon1R) has an overlap of 9 bp with exon 2 of INSP109 at its 5' end. The forward primer for exon 2 (INSP109-exon2F) has a 9 bp overlap with exon 1 of INSP109 at its 5' end.

To generate exon 1 of INSP109, the PCR reaction was performed in a final volume of 50 μl and contained 1 μl of genomic DNA (0.1 μg/μl (Novagen Inc.), 1.5 μl of 10 mM dNTPs (Amersham Pharmacia Biotech), 1 μl of MgSO$_4$ (Invitrogen), 1.5 μl of INSP109-exon1F (10 μM), 1.5 μl of INSP109-exon1R (101M), 10 μl of 10×Pfx buffer and 0.5 μl of Pfx polymerase (2.5 U/μl) (Invitrogen). The PCR conditions were 94° C. for 5 min; 30 cycles of 94° C. for 15 s, 57° C. for 30 s and 68° C. for 30 sec; an additional elongation cycle of 68° C. for 7 min; and a holding cycle of 4° C. Reaction products were loaded onto a 2% agarose gel (1×TAE) and PCR products of the correct size (64 bp) were gel-purified using a Qiaquick Gel Extraction Kit (Qiagen cat. no. 28704) and eluted in 30 μl of elution buffer (Qiagen). Exon 2 of INSP109 was produced and purified using the same except that the PCR primers were INSP109-exon2F and INSP109-exon2R, and the annealing temperature used was 63° C. The INSP109 exon 2 PCR product was 190 bp.

1.2 Assembly of Exons 1 and 2 to Generate the INSP109 ORF

Exons 1 and 2 were assembled in a 50 μl PCR reaction containing 5 μl of gel purified exon 1, 5 μl of gel purified exon 2, 1 μl of 10 mM dNTPs, 2 μl of MgSO$_4$, 1 μl of INSP109-exon1F (10 μM), 1 μl of INSP109-exon2R (10 μM), 5 μl of 10× Platinum Taq HiFi buffer, and 0.5 μl of Platinum Taq HiFi DNA polymerase (5 U/μl) (Invitrogen). The reaction conditions were: 94° C., 2 min; 35 cycles of 94° C. for 30 s, 60° C. for 30 s and 68° C. for 1 min; an additional elongation cycle of 68° C. for 7 min; and a holding cycle of 4° C. Reaction products were analysed on a 2% agarose gel (1×TAE). PCR products of the correct size (236 bp) were gel purified using the Qiagen MinElute DNA purification system (Qiagen) according to the manufacturer's instructions, eluted in 10 μl of EB buffer (10 mM Tris.Cl, pH 8.5) and subcloned directly.

1.3 Subcloning of PCR Products

The PCR product was subcloned into the topoisomerase I modified cloning vector (pCR4-TOPO) purchased from the Invitrogen Corporation using the conditions specified by the manufacturer. Briefly, 4 µl of gel purified PCR product was incubated for 15 min at room temperature with 1 µl of TOPO vector and 1 µl salt solution. The reaction mixture was then transformed into *E. coli* strain TOP10 (Invitrogen) as follows: a 50 µl aliquot of One Shot TOP10 cells was thawed on ice and 2 µl of TOPO reaction was added. The mixture was incubated for 15 min on ice and then heat shocked by incubation at 42° C. for exactly 30 s. Samples were returned to ice and 250 µl of warm (room temperature) SOC media was added. Samples were incubated with shaking (220 rpm) for 1 h at 37° C. The transformation mixture was then plated on L-broth (LB) plates containing ampicillin (100 µg/ml) and incubated overnight at 37° C.

1.4 Colony PCR

Ampicillin resistant colonies were inoculated into 50 µl sterile water using a sterile toothpick. A 10 µl aliquot of the inoculum was then subjected to PCR in a total reaction volume of 20 µl containing 1× AmpliTaq™ buffer, 200 µM dNTPs, 20 pmoles T7 primer, 20 pmoles of T3 primer, 1 unit of AmpliTaq™ (Perkin Elmer) using an MJ Research DNA Engine. The cycling conditions were as follows: 94° C., 2 min; 30 cycles of 94° C., 30 sec, 48° C., 30 sec and 72° C. for 1 min. Samples were maintained at 4° C. (holding cycle) before further analysis.

PCR reaction products were analyzed on 1% agarose gels in 1×TAE buffer. Colonies which gave the expected PCR product size (236 bp cDNA+103 bp due to the multiple cloning site or MCS) were grown up overnight at 37° C. in 5 ml L-Broth (LB) containing ampicillin (100 µg/ml), with shaking at 220 rpm.

1.5 Plasmid DNA Preparation and Sequencing

Miniprep plasmid DNA was prepared from 5 ml cultures using a Qiaprep Turbo 9600 robotic system (Qiagen) or Wizard Plus SV Minipreps kit (Promega cat. no. 1460) according to the manufacturer's instructions. Plasmid DNA was eluted in 100 µl of sterile water. The DNA concentration was measured using an Eppendorf BO photometer. Plasmid DNA (200-500 ng) was subjected to DNA sequencing with the T7 primer using the BigDyeTerminator system (Applied Biosystems cat. no. 4390246) according to the manufacturer's instructions. The primer sequences are shown in Table 2. Sequencing reactions were purified using Dye-Ex columns (Qiagen) or Montage SEQ 96 cleanup plates (Millipore cat. no. LSKS09624) then analyzed on an Applied Biosystems 3700 sequencer.

Sequence analysis identified a clone containing 100% match to the predicted INSP109 sequence. The sequence of the cloned cDNA fragment is shown in FIG. 18. The plasmid map of the cloned PCR product (pCR4-TOPO-INSP109) (plasmid ID. 13984) is shown in FIG. 19.

3. Construction of a Plasmid for the Expression of INSP109 in HEK293/EBNA Cells.

A pCR4-TOPO clone containing the full coding sequence (ORF) of INSP109 identified by DNA sequencing (pCR4-TOPO-INSP109, plasmid ID. 13984) (FIG. 19) was then used to subclone the insert into the mammalian cell expression vectors pEAK12d (FIG. 11) and pDEST12.2 (FIG. 12) using the Gateway™ cloning methodology (Invitrogen).

2.1 Generation of Gateway Compatible INSP109 ORF Fused to an in Frame 6HIS Tag Sequence.

The first stage of the Gateway cloning process involves a two step PCR reaction which generates the ORF of INSP109 flanked at the 5' end by an attB1 recombination site and Kozak sequence, and flanked at the 3' end by a sequence encoding an in frame 6 histidine (6HIS) tag, a stop codon and the attB2 recombination site (Gateway compatible cDNA). The first PCR reaction (in a final volume of 50 µl) contains: 1.5 µl of pCR4-TOPO-INSP109 (plasmid ID 13984), 1.5 µl dNTPs (10 mM), 5 µl of 10×Pfx polymerase buffer, 1 µl MgSO$_4$ (50 mM), 0.5 µl each of gene specific primer (100 µM) (INSP109-EX1 and INSP109-EX2), 2.5 µl 10× Enhancer™ solution (Invitrogen) and 1 µl Platinum Pfx DNA polymerase (Invitrogen). The PCR reaction was performed using an initial denaturing step of 95° C. for 2 min, followed by 15 cycles of 94° C. for 15 s; 55° C. for 30 s and 68° C. for 2 min 30 sec; and a holding cycle of 4° C. The amplification products were purified directly from the PCR mixture using the Wizard PCR Preps DNA Purification System (Promega) and recovered in 50 µl sterile water according to the manufacturer's instructions.

The second PCR reaction (in a final volume of 50 µl) contained 10 µl purified PCR 1 product, 1.5 µl dNTPs (10 mM), 5 µl of 10×Pfx polymerase buffer, 1 µl MgSO$_4$ (50 mM), 0.5 µl of each Gateway conversion primer (100 µM) (GCP forward and GCP reverse) and 0.5 µl of Platinum Pfx DNA polymerase. The conditions for the 2nd PCR reaction were: 95° C. for 1 min; 4 cycles of 94° C., 15 sec; 50° C., 30 sec and 68° C. for 2 min 30 sec; 19 cycles of 94° C., 15 sec; 55° C., 30 sec and 68° C., 2 min 30 sec; followed by a holding cycle of 4° C. PCR products were gel purified using the Wizard PCR prep DNA purification system (Promega) according to the manufacturer's instructions.

2.2 Subcloning of Gateway Compatible INSP109 ORF into Gateway Entry Vector pDONR221 and Expression Vectors pEAK12d and pDEST12.2

The second stage of the Gateway cloning process involves subcloning of the Gateway modified PCR product into the Gateway entry vector pDONR221 (Invitrogen, FIG. 10) as follows: 5 µL of purified product from PCR2 were incubated with 1 µl pDONR221 vector (0.15 µg/µl), 2 µl BP buffer and 1.5 µl of BP clonase enzyme mix (Invitrogen) in a final volume of 10 µl at RT for 1 h. The reaction was stopped by addition of proteinase K (2 µg) and incubated at 37° C. for a further 10 min. An aliquot of this reaction (2 µl) was used to transform *E. coli* DH10B cells by electroporation as follows: a 30 µl aliquot of DH10B electrocompetent cells (Invitrogen) was thawed on ice and 2 µl of the BP reaction mix was added. The mixture was transferred to a chilled 0.1 cm electroporation cuvette and the cells electroporated using a BioRad Gene-Pulser™ according to the manufacturer's recommended protocol. SOC media (0.5 ml) which had been pre-warmed to room temperature was added immediately after electroporation. The mixture was transferred to a 15 ml snap-cap tube and incubated, with shaking (220 rpm) for 1 h at 37° C. Aliquots of the transformation mixture (10 µl and 50 µl) were then plated on L-broth (LB) plates containing kanamycin (40 µg/ml) and incubated overnight at 37° C.

Plasmid mini-prep DNA was prepared from 5 ml cultures from 6 of the resultant colonies using a Qiaprep Turbo 9600 robotic system (Qiagen). Plasmid DNA (200-500 ng) was subjected to DNA sequencing with 21M13 and M13Rev primers using the BigDyeTerminator system (Applied Biosystems cat. no. 4390246) according to the manufacturer's instructions. The primer sequences are shown in Table 2. Sequencing reactions were purified using Dye-Ex columns (Qiagen) or Montage SEQ 96 cleanup plates (Millipore cat. no. LSKS09624) then analyzed on an Applied Biosystems 3700 sequencer.

Plasmid eluate (2 µl) from one of the clones which contained the correct sequence (pDONR221-INSP109-6HIS, plasmid ID 14230, FIG. 20) was then used in a recombination reaction containing 1.5 μl of either pEAK12d vector or pDEST12.2 vector (FIGS. 11 & 12) (0.1 μg/μl), 2 μl LR buffer and 1.5 μl of LR clonase (Invitrogen) in a final volume of 10 μl. The mixture was incubated at RT for 1 h, stopped by addition of proteinase K (2 μg) and incubated at 37° C. for a further 10 min. An aliquot of this reaction (1 μl) was used to transform *E. coli* DH10B cells by electroporation as follows: a 30 μl aliquot of DH10B electrocompetent cells (Invitrogen) was thawed on ice and 1 μl of the LR reaction mix was added. The mixture was transferred to a chilled 0.1 cm electroporation cuvette and the cells electroporated using a BioRad Gene-Pulser™ according to the manufacturer's recommended protocol. SOC media (0.5 ml) which had been pre-warmed to room temperature was added immediately after electroporation. The mixture was transferred to a 15 ml snap-cap tube and incubated, with shaking (220 rpm) for 1 h at 37° C. Aliquots of the transformation mixture (10 μl and 50 μl) were then plated on L-broth (LB) plates containing ampicillin (100 μg/ml) and incubated overnight at 37° C.

Plasmid mini-prep DNA was prepared from 5 ml cultures from 6 of the resultant colonies subcloned in each vector using a Qiaprep Turbo 9600 robotic system (Qiagen). Plasmid DNA (200-500 ng) in the pEAK12d vector was subjected to DNA sequencing with pEAK12F and pEAK12R primers as described above. Plasmid DNA (200-500 ng) in the pDEST12.2 vector was subjected to DNA sequencing with 21M13 and M13Rev primers as described above. Primers sequences are shown in Table 2.

CsCl gradient purified maxi-prep DNA was prepared from a 500 ml culture of one of each of the sequence verified clones (pEAK12d-INSP109-6HIS, plasmid ID number 14231, FIG. 21, and pDEST12.2-INSP109-6HIS, plasmid ID 14350, FIG. 22) using the method described by Sambrook J. et al., 1989 (in Molecular Cloning, a Laboratory Manual, 2$^{nd}$ edition, Cold Spring Harbor Laboratory Press). Plasmid DNA was resuspended at a concentration of 1 μg/μl in sterile water and stored at −20° C.

TABLE 2

Primers for INSP109 cloning and sequencing

| Primer | Sequence (5'-3') |
|---|---|
| GCP Forward | G GGG ACA AGT TTG TAC AAA AAA GCA GGC TTC <u>GCC ACC</u> |
| GCP Reverse | GGG GAC CAC TTT GTA CAA GAA AGC TGG GTT TCA *ATG GTG ATG GTG ATG GTG* |
| INSP109-exon1F | ATG AAC CTC TGT CTT TCT GCA TTA CTC |
| INSP109-exon1R | TAC CTT TTC CTG AAG GCA GTA AGA TCA C |
| INSP109-exon2F | TGC CTT CAG GAA AAG GTA TGT TTG GGA ATG |
| INSP109-exon2R | TAA TGA ACC CAT GGA TCT TTG GCT TGC GG |
| INSP109-EX1 | GCA GGC TTC <u>GCC ACC</u> ATG AAC CTC TGT CTT TCT GC |
| INSP109-EX2 | *GTG ATG GTG ATG GTG ATG* AAC CCA TGG ATC TTT GG |
| pEAK12-F | GCC AGC TTG GCA CTT GAT GT |
| pEAK12-R | GAT GGA GGT GGA CGT GTC AG |

TABLE 2-continued

Primers for INSP109 cloning and sequencing

| Primer | Sequence (5'-3') |
|---|---|
| pENTR-F | TCG CGT TAA CGC TAG CAT GGA TCT C |
| pENTR-R | GTA ACA TCA GAG ATT TTG AGA CAC |
| T7 | TAA TAC GAC TCA CTA TAG GG |
| T3 | CTC CCT TTA GTG AGG GTA ATT |

<u>Underlined</u> sequence = Kozak sequence
Bold = Stop codon
*Italic* sequence = His tag
Highlighted Sequence = overlap with adjacent exon Example 7

Expression and Purification of INSP108 and INSP109

Further experiments may now be performed to determine the tissue distribution and expression levels of the INSP108 and INSP109 polypeptides in vivo, on the basis of the nucleotide and amino acid sequence disclosed herein.

The presence of the transcripts for INSP108 and INSP109 may be investigated by PCR of cDNA from different human tissues. The INSP108 and INSP109 transcripts may be present at very low levels in the samples tested. Therefore, extreme care is needed in the design of experiments to establish the presence of a transcript in various human tissues as a small amount of genomic contamination in the RNA preparation will provide a false positive result. Thus, all RNA should be treated with DNAse prior to use for reverse transcription. In addition, for each tissue a control reaction may be set up in which reverse transcription was not undertaken (a −ve RT control).

For example, 1 μg of total RNA from each tissue may be used to generate cDNA using Multiscript reverse transcriptase (ABI) and random hexamer primers. For each tissue, a control reaction is set up in which all the constituents are added except the reverse transcriptase (−ve RT control). PCR reactions are set up for each tissue on the reverse transcribed RNA samples and the minus RT controls. INSP085-specific primers may readily be designed on the basis of the sequence information provided herein. The presence of a product of the correct molecular weight in the reverse transcribed sample together with the absence of a product in the minus RT control may be taken as evidence for the presence of a transcript in that tissue. Any suitable cDNA libraries may be used to screen for the INSP108 and INSP109 transcripts, not only those generated as described above.

The tissue distribution pattern of the INSP108 and INSP109 polypeptides will provide further useful information in relation to the function of those polypeptides.

In addition, further experiments may now be performed using the pEAK12d-INSP108-6HIS, pEAK12d-INSP109-6HIS, pDEST12.2-INSP108-6HIS and pDEST12.2-INSP109-6HIS expression vectors. Transfection of mammalian cell lines with these vectors may enable the high level expression of the INSP108 and INSP109 proteins and thus enable the continued investigation of the functional characteristics of the INSP108 and INSP109 polypeptides. The following material and methods are an example of those suitable in such experiments:

Cell Culture

Human Embryonic Kidney 293 cells expressing the Epstein-Barr virus Nuclear Antigen (HEK293-EBNA, Invitrogen) are maintained in suspension in Ex-cell VPRO serum-free medium (seed stock, maintenance medium, JRH). Sixteen to 20 hours prior to transfection (Day-1), cells are seeded in 2×T225 flasks (50 ml per flask in DMEM/F12 (1:1) containing 2% FBS seeding medium (JRH) at a density of 2×10$^5$ cells/ml). The next day (transfection day 0) transfection takes place using the JetPEI™ reagent (2 µl/µg of plasmid DNA, PolyPlus-transfection). For each flask, plasmid DNA is co-transfected with GFP (fluorescent reporter gene) DNA. The transfection mix is then added to the 2×T225 flasks and incubated at 37° C. (5% CO$_2$) for 6 days. Confirmation of positive transfection may be carried out by qualitative fluorescence examination at day 1 and day 6 (Axiovert 10 Zeiss).

On day 6 (harvest day), supernatants from the two flasks are pooled and centrifuged (e.g. 4° C., 400 g) and placed into a pot bearing a unique identifier. One aliquot (500 µl) is kept for QC of the 6His-tagged protein (internal bioprocessing QC).

Scale-up batches may be produced by following the protocol called "PEI transfection of suspension cells", referenced BP/PEI/HH/02/04, with PolyEthylenelmine from Polysciences as transfection agent.

Purification Process

The culture medium sample containing the recombinant protein with a C-terminal 6His tag is diluted with cold buffer A (50 mM NaH$_2$PO$_4$; 600 mM NaCl; 8.7% (w/v) glycerol, pH 7.5). The sample is filtered then through a sterile filter (Millipore) and kept at 4° C. in a sterile square media bottle (Nalgene).

The purification is performed at 4° C. on the VISION workstation (Applied Biosystems) connected to an automatic sample loader (Labomatic). The purification procedure is composed of two sequential steps, metal affinity chromatography on a Poros 20 MC (Applied Biosystems) column charged with Ni ions (4.6×50 mm, 0.83 ml), followed by gel filtration on a Sephadex G-25 medium (Amersham Pharmacia) column (1.0×10 cm).

For the first chromatography step the metal affinity column is regenerated with 30 column volumes of EDTA solution (100 mM EDTA; 1M NaCl; pH 8.0), recharged with Ni ions through washing with 15 column volumes of a 100 mM NiSO$_4$ solution, washed with 10 column volumes of buffer A, followed by 7 column volumes of buffer B (50 mM NaH$_2$PO$_4$; 600 mM NaCl; 8.7% (w/v) glycerol, 400 mM; imidazole, pH 7.5), and finally equilibrated with 15 column volumes of buffer A containing 15 mM imidazole. The sample is transferred, by the Labomatic sample loader, into a 200 ml sample loop and subsequently charged onto the Ni metal affinity column at a flow rate of 10 ml/min. The column is washed with 12 column volumes of buffer A, followed by 28 column volumes of buffer A containing 20 mM imidazole. During the 20 mM imidazole wash loosely attached contaminating proteins are eluted from the column. The recombinant His-tagged protein is finally eluted with 10 column volumes of buffer B at a flow rate of 2 ml/min, and the eluted protein is collected.

For the second chromatography step, the Sephadex G-25 gel-filtration column is regenerated with 2 ml of buffer D (1.137M NaCl; 2.7 mM KCl; 1.5 mM KH$_2$PO$_4$; 8 mM Na$_2$HPO$_4$; pH 7.2), and subsequently equilibrated with 4 column volumes of buffer C (137 mM NaCl; 2.7 mM KCl; 1.5 mM KH$_2$PO$_4$; 8 mM Na$_2$HPO$_4$; 20% (w/v) glycerol; pH 7.4). The peak fraction eluted from the Ni-column is automatically loaded onto the Sephadex G-25 column through the integrated sample loader on the VISION and the protein is eluted with buffer C at a flow rate of 2 ml/min. The fraction was filtered through a sterile centrifugation filter (Millipore), frozen and stored at −80° C. An aliquot of the sample is analyzed on SDS-PAGE (4-12% NuPAGE gel; Novex) Western blot with anti-His antibodies. The NuPAGE gel may be stained in a 0.1% Coomassie blue R250 staining solution (30% methanol, 10% acetic acid) at room temperature for 1 h and subsequently destained in 20% methanol, 7.5% acetic acid until the background is clear and the protein bands clearly visible.

Following the electrophoresis the proteins are electrotransferred from the gel to a nitrocellulose membrane. The membrane is blocked with 5% milk powder in buffer E (137 mM NaCl; 2.7 mM KCl; 1.5 mM KH$_2$PO$_4$; 8 mM Na$_2$HPO$_4$; 0.1% Tween 20, pH 7.4) for 1 h at room temperature, and subsequently incubated with a mixture of 2 rabbit polyclonal anti-His antibodies (G-18 and H-15, 0.2 µg/ml each; Santa Cruz) in 2.5% milk powder in buffer E overnight at 4° C. After a further 1 hour incubation at room temperature, the membrane is washed with buffer E (3×10 min), and then incubated with a secondary HRP-conjugated anti-rabbit antibody (DAKO, HRP 0399) diluted 1/3000 in buffer E containing 2.5% milk powder for 2 hours at room temperature. After washing with buffer E (3×10 minutes), the membrane is developed with the ECL kit (Amersham Pharmacia) for 1 min. The membrane is subsequently exposed to a Hyperfilm (Amersham Pharmacia), the film developed and the western blot image visually analysed.

For samples that showed detectable protein bands by Coomassie staining, the protein concentration may be determined using the BCA protein assay kit (Pierce) with bovine serum albumin as standard.

Furthermore, overexpression or knock-down of the expression of the polypeptides in cell lines may be used to determine the effect on transcriptional activation of the host cell genome. Dimerisation partners, co-activators and co-repressors of the INSP108 and INSP109 polypeptide may be identified by immunoprecipitation combined with Western blotting and immunoprecipitation combined with mass spectroscopy.

Example 8

Assays for the Detection of Defensin Activity

Cell- and Animal-Based Assay for the Validation and Characterization of the Chemokine-Like Polypeptides.

Several assays have been developed for testing specificity, potency, and efficacy of chemokines using cell cultures or animal models, for example in vitro chemotaxis assays (Proudfoot A, et al. J Biol Chem 276: 10620-10626, 2001; Lusti-Narasimhan M et al., J Biol Chem, 270: 2716-21, 1995), or mouse ear swelling (Garrigue J L et al., Contact Dermatitis, 30: 231-7, 1994). Many other assays and technologies for generating useful tools and products (antibodies, transgenic animals, radiolabeled proteins, etc.) have been described in reviews and books dedicated to chemokines (Methods Mol. Biol vol. 138, "Chemokines Protocols", edited by Proudfoot A I et al., Humana Press Inc., 2000; Methods Enzymol, vol. 287 and 288, Academic Press, 1997), and can be used to verify, in a more precise manner, the biological activities of the chemokine-like polypeptides of the invention and related reagents in connection with possible therapeutic or diagnostic methods and uses.

Cytokine Expression Modulation Assays

The following in vitro cell-based tri-replicas assays measure the effects of the protein of the invention on cytokine secretion induced by Concanavalin A (Con A) acting on different human peripheral blood mononuclear cells (hPBMC) cells as measured by a cytokine bead array (CBA) assay for IL-2, IFN-γ, TNF-α, IL-5, IL-4 and IL-10 such as the Human Th1/Th2 Cytokine CBA kit (Becton-Dickinson).

The optimal conditions are 100 000 cells/well in 96-well plates and 100 µl final in 2% glycerol. The optimal concentration of mitogen (ConA) is 5 ng/ml. The optimal time for the assay is 48 h. The read-out choice is the CBA.

1 Purification of Human PBMC from a Buffy Coat

The buffy coat 1 to 2 is diluted with DMEM. 25 ml of diluted blood was thereafter slowly added onto a 15 ml layer of Ficoll in a 50 ml Falcon tube, and tubes are centrifuged (2000 rpm, 20 min, at RT without brake). The interphase (ring) is then collected and the cells are washed with 25 ml of DMEM followed by a centrifuge step (1200 rpm, 5 min). This procedure is repeated three times. A buffy coat gives approximately $600 \times 10^6$ total cells.

2 Screening

80 µl of $1.25 \times 10^6$ cells/ml are diluted in DMEM+2.5% Human Serum+1% L-Glutamine+1% Penicillin-Streptomycin and thereafter added to a 96 well microtiter plate.

10 µl are added per well (one condition per well): Proteins were diluted in PBS+20% Glycerol (the final dilution of the proteins is 1/10).

10 µl of the ConA Stimulant (50 µg/ml) are then added per well (one condition per well—the final concentration of ConA is 5 µg/ml)

After 48 h, cell supernatants are collected and human cytokines are measured by Human Th1/Th2 Cytokine CBA Kit Becton-Dickinson.

3 CBA Analysis (for more details, refer to the manufacturer's instructions in the CBA kit)

i) Preparation of mixed Human Th1/Th2 Capture Beads

The number of assay tubes that are required for the experiment are determined.

Each capture bead suspension is vigorously vortexed for a few seconds before mixing. For each assay to be analysed, 10 µl aliquot of each capture bead are added into a single tube labelled "mixed capture beads". The Bead mixture is thoroughly vortexed.

ii) Preparation of Test Samples

Supernatants are diluted (1:4) using the Assay Diluent (20 µl of supernatants+60 µl of Assay Diluent). The sample dilution is then mixed before transferring samples into a 96 well conical bottomed microtiter plate (Nunc).

iii) Human Th1/Th2 Cytokine CBA Assay Procedure

50 µl of the diluted supernatants are added into a 96 well conical bottomed microtiter plate (Nunc). 50 µl of the mixed capture beads are added followed by 50 µl addition of the Human Th1/Th2 PE Detection Reagent. The plate is then incubated for 3 hours at RT and protected from direct exposure to light followed by centrifugation at 1500 rpm for 5 minutes. The supernatant is then carefully discarded. In a subsequent step, 200 µl of wash buffer are twice added to each well, centrifuged at 1500 rpm for 5 minutes and supernatant carefully discarded. 130 µl of wash buffer are thereafter added to each well to resuspend the bead pellet. The samples are finally analysed on a flow cytometer. The data are then analysed using the CBA Application Software, Activity Base and Microsoft Excel software.

From the read-out of the assay it can be evaluated whether in vitro, the protein of the invention has a consistent inhibitory effect on all cytokines tested (IFN-γ, TNF-α, IL-2, IL-4, IL-5, IL-10).

Moreover, based on the EC50 value, it can be easily evaluated which cytokine is inhibited the most and then derive the specific auto-immune/inflammatory disease, which is known to be particularly linked to that cytokine.

Assays Targeting T Lymphocyte Responses

Fas-Ligand-induced T cell death. This assay will reveal new modulators of receptor mediated cell death.

In this assay, T cell apoptosis is induced by stimulating Jurkat cells (a human T cell line) with recombinant 6 Histidine-tagged Fas Ligand combined with a monoclonal anti 6-his antibody. Death is quantified by release of LDH, a cytoplasmic enzyme released in the culture medium when cells are dying. The read out is a colorimetric assay read at 490 nm. T cells have been shown to be pathogenic in many autoimmune diseases, being able to control antigen-specific T cell death is a therapeutic strategy (e.g. anti-TNFα treatment in patient with Crohn's disease).

Human-MLR: proliferation and cytokine secretion. This cell-based assay measures the effects of novel proteins on lymphocyte proliferation and cytokine secretion or inhibition upon stimulation by PBMC from another donor (alloreactivity). These assay address antigen-specific T cell and antigen presenting cell functions, which are crucial cellular responses in any autoimmune diseases. Secreted cytokine (IL-2, 4, 5, 10, TNF-α and IFN-γ) are quantified by CBA.

Note: proliferation and cytokine secretion are independent responses.

Mouse-MLR: proliferation. This cell-based assay measures the effects of novel proteins on lymphocyte proliferation or inhibition of mouse spleen cells following stimulation by spleen cells from another donor (mouse strain). This cell-based assay measures the effect of novel proteins on T lymphocyte and antigen presenting cell responses and will be used to confirm activity of positives and hits identify in the h-MLR assays. This assay will be use to select proteins that will be tested in murine model of human diseases.

Human PBMC Stimulated with the Superantigen, TSST.

Superantigens are strong modulators of the immune system affecting T cells. Superantigens influence immunologically mediated disorders such as IBD, inflammatory skin diseases like atopic dermatitis and psoriasis. In this cellular assay, we are specifically targeting T lymphocyte activation via the TCR but with different requirements than the T cell response to classical antigens, in particular in respect to co-stimulatory molecules.

Human PBMC stimulated with either ConA or PHA. These cell-based assays measure the effects of novel proteins on cytokine secretion induced by two different stimuli acting on different cells as measured by a cytokine bead array (CBA) assay (IL-2, IFN-γ, TNF-α, IL-5, IL-4 and IL-10).

Most of cytokines can have dual actions, pro or anti-inflammatory, depending of the injury, milieu and cellular target. Any protein with the capability to modulate cytokine secretion may have a therapeutic potential (e.g. decreasing IFN-γ and TNF-α would be beneficial in Th1-mediated autoimmune disease in contrast decreasing IL-4, IL-5 may be beneficial in Th2-mediated-diseases, inducing IL-10 would interesting in MS and SLE).

Assays Targeting Monocyte/Macrophages and Granulocyte Responses

Human PBMC stimulated with LPS. This cell-based assay measures the effects of novel proteins on cytokine secretion (IFN-γ, TNF-α) induced by LPS acting on monocytes/macrophages and granulocytes.

Any protein with the capability to modulate IFN-γ and TNF-α secretion would be beneficial in Th1-mediated autoimmune diseases.

Assays Targeting Neutrophil Responses

Neutrophils are important in inflammation and autoimmune diseases such as Rheumatoid Arthritis. Leukocyte chemo-attractants such as IL-8 initiate a sequence of adhesive interactions between cells and the micro-vascular endothelium, resulting in activation, adhesion and finally migration of neutrophils. The tissue infiltration of neutrophils depends on a reorganisation of cytoskeleton elements associated with specific changes in cell morphology of these cells.

This cell-based assay measures the effect of novel proteins on cytoskeleton reorganization of human neutrophils.

Assays Targeting B Lymphocyte Responses

Autoantibodies as well as infiltrating B cells are thought to be important in the pathogenesis of various autoimmune diseases, such as systemic lupus erithematosus (SLE), rheumatoid arthritis (RA), Sjogren's syndrome and myasthenia gravis. Compelling evidence indicates that a disregulation in B cell homeostasis could affect immune tolerance leading to the inappropriate survival of autoreactive B cells producing pathogenic antibodies and sustained inflammation. The identification of new factors that play critical roles in the regulation of B cell proliferation, survival and differentiation following B cell receptor triggering are of high relevance in the development of novel therapies.

B cell proliferation. This cell-based assay measures the effect of novel proteins on B cell survival.

B cell co-stimulation. This cell-based assay measures the effect of novel proteins on B cell co-stimulation.

Assays Targeting Monocytes and Microglial Responses

THP-1 calcium flux. The $Ca^+$-flux in THP 1-cell assay measures the effects of novel proteins on their ability to trigger an intracellular calcium release (a generic second messenger events) from the endoplasmic reticulum.

Microglia Cell Proliferation (will be Presented to the Next IAC).

During proliferation of microglial progenitors, a number of colony-stimulating factors, including some cytokines, are known to play key roles. Among them, M-CSF is crucial for the final step of maturation of macrophages/microglia and is not replaceable by any other factor. The evaluation of this biological response may represent a way to influence the microglial activity and therefore an opportunity to identify molecules with therapeutic potential from MS.

A cell-based assay was developed to measure the proliferative response of a microglia cell line to M-CSF. The feasibility and the robustness phases showed optimal results. This assay is in 96 well plates; non-radioactive substrate is required, easily automated.

We claim:

1. An isolated polypeptide comprising SEQ ID NO: 14, SEQ ID NO: 16, or a polypeptide having beta defensin activity and at least 95% sequence identity to SEQ ID NO: 14 or SEQ ID NO: 16.

2. The isolated polypeptide according to claim 1, wherein said polypeptide comprises SEQ ID NO: 14.

3. The isolated polypeptide according to claim 1, wherein said polypeptide comprises SEQ ID NO: 16.

4. The isolated polypeptide according to claim 1, wherein said polypeptide comprises a polypeptide having at least 95% sequence identity to SEQ ID NO: 14 and having beta defensin activity.

5. The isolated polypeptide according to claim 1, wherein said polypeptide comprises a polypeptide having at least 95% sequence identity to SEQ ID NO: 16 and having beta defensin activity.

6. A composition comprising a pharmaceutically acceptable excipient and a polypeptide comprising SEQ ID NO: 14, SEQ ID NO: 16, or a polypeptide having beta defensin activity and at least 95% sequence identity to SEQ ID NO: 14 or SEQ ID NO: 16.

7. The composition according to claim 6, wherein said polypeptide comprises SEQ ID NO: 14.

8. The composition according to claim 6, wherein said polypeptide comprises SEQ ID NO: 16.

9. The composition according to claim 6, wherein said polypeptide comprises a polypeptide having at least 95% sequence identity to SEQ ID NO: 14 and having beta defensin activity.

10. The composition according to claim 6, wherein said polypeptide comprises a polypeptide having at least 95% sequence identity to SEQ ID NO: 16 and having beta defensin activity.

* * * * *

SEQUENCE LISTING

```
<160> NUMBER OF SEQ ID NOS: 42

<210> SEQ ID NO 1
<211> LENGTH: 64
<212> TYPE: DNA
<213> ORGANISM: Homo sapiens

<400> SEQUENCE: 1
atggccacaa ggagcgtcct cttggccctc gtggtcctta acttactctt ctatgttcca      60
ccag                                                                   64

<210> SEQ ID NO 2
<211> LENGTH: 22
<212> TYPE: PRT
<213> ORGANISM: Homo sapiens

<400> SEQUENCE: 2

Met Ala Thr Arg Ser Val Leu Leu Ala Leu Val Val Leu Asn Leu Leu
1               5                   10                  15

Phe Tyr Val Pro Pro Gly
            20

<210> SEQ ID NO 3
<211> LENGTH: 170
<212> TYPE: DNA
<213> ORGANISM: Homo sapiens

<400> SEQUENCE: 3
gtagaagtgg acccaatgtc tacatacaaa aaatctttgc ttcatgttgg cgactgcaag      60
gtacttgccg gccaaaatgt ctaaaaaacg aacaatatcg tattttgtgt gatactatac     120
atttgtgctg tgtaaaccca aaatatttac ctatactgac tgggaaatag                170
```

```
<210> SEQ ID NO 4
<211> LENGTH: 55
<212> TYPE: PRT
<213> ORGANISM: Homo sapiens

<400> SEQUENCE: 4

Arg Ser Gly Pro Asn Val Tyr Ile Gln Lys Ile Phe Ala Ser Cys Trp
1               5                   10                  15

Arg Leu Gln Gly Thr Cys Arg Pro Lys Cys Leu Lys Asn Glu Gln Tyr
            20                  25                  30

Arg Ile Leu Cys Asp Thr Ile His Leu Cys Cys Val Asn Pro Lys Tyr
        35                  40                  45

Leu Pro Ile Leu Thr Gly Lys
    50                  55

<210> SEQ ID NO 5
<211> LENGTH: 234
<212> TYPE: DNA
<213> ORGANISM: Homo sapiens

<400> SEQUENCE: 5
atggccacaa ggagcgtcct cttggccctc gtggtcctta acttactctt ctatgttcca    60
ccaggtagaa gtggacccaa tgtctacata caaaaaatct ttgcttcatg ttggcgactg   120
caaggtactt gccggccaaa atgtctaaaa acgaacaata tcgtattttt gtgtgatact   180
atacatttgt gctgtgtaaa cccaaaatat ttacctatac tgactgggaa atag         234

<210> SEQ ID NO 6
<211> LENGTH: 77
<212> TYPE: PRT
<213> ORGANISM: Homo sapiens

<400> SEQUENCE: 6

Met Ala Thr Arg Ser Val Leu Leu Ala Leu Val Val Leu Asn Leu Leu
1               5                   10                  15

Phe Tyr Val Pro Pro Gly Arg Ser Gly Pro Asn Val Tyr Ile Gln Lys
            20                  25                  30

Ile Phe Ala Ser Cys Trp Arg Leu Gln Gly Thr Cys Arg Pro Lys Cys
        35                  40                  45

Leu Lys Asn Glu Gln Tyr Arg Ile Leu Cys Asp Thr Ile His Leu Cys
    50                  55                  60

Cys Val Asn Pro Lys Tyr Leu Pro Ile Leu Thr Gly Lys
65                  70                  75

<210> SEQ ID NO 7
<211> LENGTH: 162
<212> TYPE: DNA
<213> ORGANISM: Homo sapiens

<400> SEQUENCE: 7
ggacccaatg tctacataca aaaaatcttt gcttcatgtt ggcgactgca aggtacttgc    60
cggccaaaat gtctaaaaaa cgaacaatat cgtattttgt gtgatactat acatttgtgc   120
tgtgtaaacc caaatatttt acctatactg actgggaaat ag                      162

<210> SEQ ID NO 8
<211> LENGTH: 53
<212> TYPE: PRT
<213> ORGANISM: Homo sapiens
```

<400> SEQUENCE: 8

Gly Pro Asn Val Tyr Ile Gln Lys Ile Phe Ala Ser Cys Trp Arg Leu
1               5                   10                  15

Gln Gly Thr Cys Arg Pro Lys Cys Leu Lys Asn Glu Gln Tyr Arg Ile
            20                  25                  30

Leu Cys Asp Thr Ile His Leu Cys Cys Val Asn Pro Lys Tyr Leu Pro
        35                  40                  45

Ile Leu Thr Gly Lys
    50

<210> SEQ ID NO 9
<211> LENGTH: 55
<212> TYPE: DNA
<213> ORGANISM: Homo sapiens

<400> SEQUENCE: 9
atgaacctct gtctttctgc attactcttc ttcctggtga tcttactgcc ttcag        55

<210> SEQ ID NO 10
<211> LENGTH: 19
<212> TYPE: PRT
<213> ORGANISM: Homo sapiens

<400> SEQUENCE: 10

Met Asn Leu Cys Leu Ser Ala Leu Leu Phe Phe Leu Val Ile Leu Leu
1               5                   10                  15

Pro Ser Gly

<210> SEQ ID NO 11
<211> LENGTH: 182
<212> TYPE: DNA
<213> ORGANISM: Homo sapiens

<400> SEQUENCE: 11
gaaaaggtat gtttgggaat gatggagtca agttcgcac ctgcactagc cagaaagccg        60
tatgtttctt cgggtgtccg ccaggataca ggtggattgc gttctgccac aatattctgt      120
cttgctgtaa aaatatgaca cgttttcaac ccccgcaagc caaagatcca tgggttcatt      180
aa                                                                      182

<210> SEQ ID NO 12
<211> LENGTH: 59
<212> TYPE: PRT
<213> ORGANISM: Homo sapiens

<400> SEQUENCE: 12

Lys Gly Met Phe Gly Asn Asp Gly Val Lys Val Arg Thr Cys Thr Ser
1               5                   10                  15

Gln Lys Ala Val Cys Phe Phe Gly Cys Pro Pro Gly Tyr Arg Trp Ile
            20                  25                  30

Ala Phe Cys His Asn Ile Leu Ser Cys Cys Lys Asn Met Thr Arg Phe
        35                  40                  45

Gln Pro Pro Gln Ala Lys Asp Pro Trp Val His
    50                  55

<210> SEQ ID NO 13
<211> LENGTH: 237
<212> TYPE: DNA
<213> ORGANISM: Homo sapiens

<400> SEQUENCE: 13

```
atgaacctct gtctttctgc attactcttc ttcctggtga tcttactgcc ttcaggaaaa      60
ggtatgtttg ggaatgatgg agtcaaagtt cgcacctgca ctagccagaa agccgtatgt     120
ttcttcgggt gtccgccagg atacaggtgg attgcgttct gccacaatat tctgtcttgc     180
tgtaaaaata tgacacgttt tcaaccccccg caagccaaag atccatgggt tcattaa      237
```

<210> SEQ ID NO 14
<211> LENGTH: 78
<212> TYPE: PRT
<213> ORGANISM: Homo sapiens

<400> SEQUENCE: 14

```
Met Asn Leu Cys Leu Ser Ala Leu Leu Phe Phe Leu Val Ile Leu Leu
1               5                   10                  15

Pro Ser Gly Lys Gly Met Phe Gly Asn Asp Gly Val Lys Val Arg Thr
            20                  25                  30

Cys Thr Ser Gln Lys Ala Val Cys Phe Phe Gly Cys Pro Pro Gly Tyr
        35                  40                  45

Arg Trp Ile Ala Phe Cys His Asn Ile Leu Ser Cys Cys Lys Asn Met
    50                  55                  60

Thr Arg Phe Gln Pro Pro Gln Ala Lys Asp Pro Trp Val His
65                  70                  75
```

<210> SEQ ID NO 15
<211> LENGTH: 174
<212> TYPE: DNA
<213> ORGANISM: Homo sapiens

<400> SEQUENCE: 15

```
atgtttggga atgatggagt caaagttcgc acctgcacta gccagaaagc cgtatgtttc      60
ttcgggtgtc cgccaggata caggtggatt gcgttctgcc acaatattct gtcttgctgt    120
aaaaatatga cacgttttca accccccgcaa gccaaagatc catgggttca ttaa          174
```

<210> SEQ ID NO 16
<211> LENGTH: 57
<212> TYPE: PRT
<213> ORGANISM: Homo sapiens

<400> SEQUENCE: 16

```
Met Phe Gly Asn Asp Gly Val Lys Val Arg Thr Cys Thr Ser Gln Lys
1               5                   10                  15

Ala Val Cys Phe Phe Gly Cys Pro Pro Gly Tyr Arg Trp Ile Ala Phe
            20                  25                  30

Cys His Asn Ile Leu Ser Cys Cys Lys Asn Met Thr Arg Phe Gln Pro
        35                  40                  45

Pro Gln Ala Lys Asp Pro Trp Val His
    50                  55
```

<210> SEQ ID NO 17
<211> LENGTH: 20
<212> TYPE: DNA
<213> ORGANISM: Artificial Sequence
<220> FEATURE:
<223> OTHER INFORMATION: INSP108-CP1 Primer

<400> SEQUENCE: 17

```
attggtatgg ccacaaggag                                                  20
```

```
<210> SEQ ID NO 18
<211> LENGTH: 22
<212> TYPE: DNA
<213> ORGANISM: Artificial Sequence
<220> FEATURE:
<223> OTHER INFORMATION: INSP108-CP2 Primer

<400> SEQUENCE: 18
cacaactatt tcccagtcag ta                                              22

<210> SEQ ID NO 19
<211> LENGTH: 37
<212> TYPE: DNA
<213> ORGANISM: Artificial Sequence
<220> FEATURE:
<223> OTHER INFORMATION: INSP108-EX1 Primer

<400> SEQUENCE: 19
aagcaggctt cgccaccatg gccacaagga gcgtcct                              37

<210> SEQ ID NO 20
<211> LENGTH: 35
<212> TYPE: DNA
<213> ORGANISM: Artificial Sequence
<220> FEATURE:
<223> OTHER INFORMATION: INSP108-EX2 Primer

<400> SEQUENCE: 20
gtgatggtga tggtgttctg cctcctgcgt cttgt                                35

<210> SEQ ID NO 21
<211> LENGTH: 37
<212> TYPE: DNA
<213> ORGANISM: Artificial Sequence
<220> FEATURE:
<223> OTHER INFORMATION: GCP Forward Primer

<400> SEQUENCE: 21
ggggacaagt ttgtacaaaa aagcaggctt cgccacc                              37

<210> SEQ ID NO 22
<211> LENGTH: 51
<212> TYPE: DNA
<213> ORGANISM: Artificial Sequence
<220> FEATURE:
<223> OTHER INFORMATION: GCP Reverse Primer

<400> SEQUENCE: 22
ggggaccact ttgtacaaga aagctgggtt tcaatggtga tggtgatggt g              51

<210> SEQ ID NO 23
<211> LENGTH: 20
<212> TYPE: DNA
<213> ORGANISM: Artificial Sequence
<220> FEATURE:
<223> OTHER INFORMATION: pEAK12F Primer

<400> SEQUENCE: 23
gccagcttgg cacttgatgt                                                 20

<210> SEQ ID NO 24
<211> LENGTH: 20
<212> TYPE: DNA
<213> ORGANISM: Artificial Sequence
<220> FEATURE:
<223> OTHER INFORMATION: pEAK12R Primer
```

<400> SEQUENCE: 24
gatggaggtg gacgtgtcag                                           20

<210> SEQ ID NO 25
<211> LENGTH: 18
<212> TYPE: DNA
<213> ORGANISM: Artificial Sequence
<220> FEATURE:
<223> OTHER INFORMATION: 21M13 Primer

<400> SEQUENCE: 25
tgtaaaacga cggccagt                                             18

<210> SEQ ID NO 26
<211> LENGTH: 18
<212> TYPE: DNA
<213> ORGANISM: Artificial Sequence
<220> FEATURE:
<223> OTHER INFORMATION: M13REV Primer

<400> SEQUENCE: 26
caggaaacag ctatgacc                                             18

<210> SEQ ID NO 27
<211> LENGTH: 19
<212> TYPE: DNA
<213> ORGANISM: T7 Primer

<400> SEQUENCE: 27
taatacgact cactatagg                                            19

<210> SEQ ID NO 28
<211> LENGTH: 18
<212> TYPE: DNA
<213> ORGANISM: T3 Primer

<400> SEQUENCE: 28
attaaccctc actaaagg                                             18

<210> SEQ ID NO 29
<211> LENGTH: 27
<212> TYPE: DNA
<213> ORGANISM: Artificial Sequence
<220> FEATURE:
<223> OTHER INFORMATION: INSP109-exon1F Primer

<400> SEQUENCE: 29
atgaacctct gtctttctgc attactc                                   27

<210> SEQ ID NO 30
<211> LENGTH: 28
<212> TYPE: DNA
<213> ORGANISM: Artificial Sequence
<220> FEATURE:
<223> OTHER INFORMATION: INSP109-exon1R Primer

<400> SEQUENCE: 30
tacctttccc tgaaggcagt aagatcac                                  28

<210> SEQ ID NO 31
<211> LENGTH: 30
<212> TYPE: DNA
<213> ORGANISM: Artificial Sequence
<220> FEATURE:
<223> OTHER INFORMATION: INSP109-exon2F Primer
<210> SEQ ID NO 31
<211> LENGTH: 30
<212> TYPE: DNA
<213> ORGANISM: Artificial Sequence
<220> FEATURE:
<223> OTHER INFORMATION: INSP109-exon2R Primer

<400> SEQUENCE: 31
tgccttcagg aaaaggtatg tttgggaatg                              30

<210> SEQ ID NO 32
<211> LENGTH: 29
<212> TYPE: DNA
<213> ORGANISM: Artificial Sequence
<220> FEATURE:
<223> OTHER INFORMATION: INSP109-exon2R Primer

<400> SEQUENCE: 32
taatgaaccc atggatcttt ggcttgcgg                               29

<210> SEQ ID NO 33
<211> LENGTH: 35
<212> TYPE: DNA
<213> ORGANISM: Artificial Sequence
<220> FEATURE:
<223> OTHER INFORMATION: INSP109-EX1 Primer

<400> SEQUENCE: 33
gcaggcttcg ccaccatgaa cctctgtctt tctgc                        35

<210> SEQ ID NO 34
<211> LENGTH: 35
<212> TYPE: DNA
<213> ORGANISM: Artificial Sequence
<220> FEATURE:
<223> OTHER INFORMATION: INSP109-EX2 Primer

<400> SEQUENCE: 34
gtgatggtga tggtgatgaa cccatggatc tttgg                        35

<210> SEQ ID NO 35
<211> LENGTH: 25
<212> TYPE: DNA
<213> ORGANISM: Artificial Sequence
<220> FEATURE:
<223> OTHER INFORMATION: pENTR-F Primer

<400> SEQUENCE: 35
tcgcgttaac gctagcatgg atctc                                   25

<210> SEQ ID NO 36
<211> LENGTH: 24
<212> TYPE: DNA
<213> ORGANISM: Artificial Sequence
<220> FEATURE:
<223> OTHER INFORMATION: pENTR-R Primer

<400> SEQUENCE: 36
gtaacatcag agattttgag acac                                    24

<210> SEQ ID NO 37
<211> LENGTH: 434
<212> TYPE: DNA
<213> ORGANISM: Artificial Sequence
<220> FEATURE:
<223> OTHER INFORMATION: predicted nucleotide sequence of INSP108

<400> SEQUENCE: 37
ttgttccaaa aggttcacta gccatgcagc tccccgtctc ttcaaagctg cggagagagt    60
gactctccga tgagtcacag ctgcttcttt gctgattggt atggccacaa ggagcgtcct   120
cttggccctc gtggtcctta acttactctt ctatgttcca ccaggtagaa gtggacccaa   180

```
tgtctacata caaaaaatct ttgcttcatg ttggcgactg caaggtactt gccggccaaa      240
atgtctaaaa aacgaacaat atcgtatttt gtgtgatact atacatttgt gctgtgtaaa      300
cccaaaatat ttacctatac tgactgggaa atagttgtga gtacctgaaa gctgttgctg      360
atttcctctg ggaacccaga tccctctcag ttgcaccatt cgattaaaac aatggcttta      420
gcctatcagt gttc                                                        434
```

<210> SEQ ID NO 38
<211> LENGTH: 77
<212> TYPE: PRT
<213> ORGANISM: Artificial Sequence
<220> FEATURE:
<223> OTHER INFORMATION: translation of INSP108 PCR product

<400> SEQUENCE: 38

```
Met Ala Thr Arg Ser Val Leu Leu Ala Leu Val Val Leu Asn Leu Leu
1               5                   10                  15

Phe Tyr Val Pro Pro Gly Arg Ser Gly Pro Asn Val Tyr Ile Gln Lys
            20                  25                  30

Ile Phe Ala Ser Cys Trp Arg Leu Gln Gly Thr Cys Arg Pro Lys Cys
        35                  40                  45

Leu Lys Asn Glu Gln Tyr Arg Ile Leu Cys Asp Thr Ile His Leu Cys
    50                  55                  60

Cys Val Asn Pro Lys Tyr Leu Pro Ile Leu Thr Gly Lys
65                  70                  75
```

<210> SEQ ID NO 39
<211> LENGTH: 245
<212> TYPE: DNA
<213> ORGANISM: Artificial Sequence
<220> FEATURE:
<223> OTHER INFORMATION: nucleotide sequence of INSP108 PCR product

<400> SEQUENCE: 39

```
attggtatgg ccacaaggag cgtcctcttg gccctcgtgg tccttaactt actcttctat      60
gttccaccag gtagaagtgg acccaatgtc tacatacaaa aaatctttgc ttcatgttgg     120
cgactgcaag gtacttgccg gccaaaatgt ctaaaaaacg aacaatatcg tattttgtgt     180
gatactatac atttgtgctg tgtaaaccca aaatatttac ctatactgac tgggaaatag     240
ttgtg                                                                 245
```

<210> SEQ ID NO 40
<211> LENGTH: 234
<212> TYPE: DNA
<213> ORGANISM: Artificial Sequence
<220> FEATURE:
<223> OTHER INFORMATION: predicted nucleotide sequence of INSP109

<400> SEQUENCE: 40

```
atgaacctct gtctttctgc attactcttc ttcctggtga tcttactgcc ttcaggaaaa      60
ggtatgtttg ggaatgatgg agtcaaagtt cgcacctgca ctagccagaa agccgtatgt     120
ttcttcgggt gtccgccagg atacaggtgg attgcgttct gccacaatat tctgtcttgc     180
tgtaaaaata tgacacgttt tcaaccccccg caagccaaag atccatgggt tcat           234
```

<210> SEQ ID NO 41
<211> LENGTH: 247
<212> TYPE: DNA
<213> ORGANISM: Artificial Sequence

```
<220> FEATURE:
<223> OTHER INFORMATION: INSP109 genomic DNA

<400> SEQUENCE: 41
atgaacctct gtctttctgc attactcttc ttcctggtga tcttactgcc ttcaggtaag      60
ttcaggaaaa ggtatgtttg ggaatgatgg agtcaaagtt cgcacctgca ctagccagaa     120
agccgtatgt ttcttcgggt gtccgccagg atacaggtgg attgcgttct gccacaatat    180
tctgtcttgc tgtaaaaata tgacacgttt tcaaccccg caagccaaag atccatgggt      240
tcattaa                                                               247

<210> SEQ ID NO 42
<211> LENGTH: 236
<212> TYPE: DNA
<213> ORGANISM: Artificial Sequence
<220> FEATURE:
<223> OTHER INFORMATION: nucleotide sequence of cloned INSP109 ORF

<400> SEQUENCE: 42
atgaacctct gtctttctgc attactcttc ttcctggtga tcttactgcc ttcaggaaaa     60
ggtatgtttg ggaatgatgg agtcaaagtt cgcacctgca ctagccagaa agccgtatgt    120
ttcttcgggt gtccgccagg atacaggtgg attgcgttct gccacaatat tctgtcttgc   180
tgtaaaaata tgacacgttt tcaaccccg caagccaaag atccatggt tcatta          236
```